(12) United States Patent
Hayes et al.

(10) Patent No.: US 12,414,863 B2
(45) Date of Patent: Sep. 16, 2025

(54) EXPANDABLE INTERBODY IMPLANT AND CORRESPONDING SURGICAL TOOL

(71) Applicant: Warsaw Orthopedic, Inc., Warsaw, IN (US)

(72) Inventors: Stanley Kyle Hayes, Mission Viejo, CA (US); Robert M. Loke, Memphis, TN (US); Charlie J. Barfield, East Hernando, MS (US); Dimitri K. Protopsaltis, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 534 days.

(21) Appl. No.: 17/736,523

(22) Filed: May 4, 2022

(65) Prior Publication Data

US 2022/0409398 A1    Dec. 29, 2022

Related U.S. Application Data

(63) Continuation-in-part of application No. 17/665,449, filed on Feb. 4, 2022, and a continuation-in-part of
(Continued)

(51) Int. Cl.
*A61F 2/44* (2006.01)
*A61F 2/46* (2006.01)
*A61F 2/30* (2006.01)

(52) U.S. Cl.
CPC .......... *A61F 2/4611* (2013.01); *A61F 2/442* (2013.01); *A61F 2/447* (2013.01);
(Continued)

(58) Field of Classification Search
CPC ........ A61F 2/4611; A61F 2/442; A61F 2/447; A61F 2002/30405; A61F 2002/30433;
(Continued)

(56) References Cited

U.S. PATENT DOCUMENTS 1,677,337 A    7/1928  Grove
3,847,154 A    11/1974 Nordin
(Continued)

FOREIGN PATENT DOCUMENTS

CN    107 137 166 A    9/2017
DE    44 16 605 C1     6/1995
(Continued)

OTHER PUBLICATIONS

Chinese Office Action in Application No. 201980010758.4 dated Sep. 16, 2023.
(Continued)

*Primary Examiner* — Jessica Weiss
(74) *Attorney, Agent, or Firm* — FOX ROTHSCHILD LLP

(57) ABSTRACT

An interbody system including an implant and a tool for inserting and expanding the medical implant and locking the implant in place is disclosed. The medical implant may include an expandable body defined by a superior endplate and an inferior endplate that are hingedly coupled and may be expanded and lordosed. The superior and inferior endplate may include radially disposed and opposed surfaces that mate and/or directly contact each other when a locking screw is threaded through a screw aperture. The implant may include a threaded breakoff screw disposed in the threaded screw aperture and movable between a locked position and an unlocked position, for example. In the locked position, the threaded locking screw may urge the distal engagement surface of the first core into direct contact with the proximal engagement surface of the second core. When broken, the breakoff screw may comprise a recessed fracture surface.

17 Claims, 56 Drawing Sheets

Related U.S. Application Data application No. 17/515,709, filed on Nov. 1, 2021, now Pat. No. 12,295,865, and a continuation-in-part of application No. 17/356,950, filed on Jun. 24, 2021, now Pat. No. 11,612,499.

(52) U.S. Cl.
CPC .............. *A61F 2002/30405* (2013.01); *A61F 2002/30433* (2013.01); *A61F 2002/30556* (2013.01); *A61F 2002/30579* (2013.01); *A61F 2002/4627* (2013.01)

(58) Field of Classification Search
CPC .. A61F 2002/30556; A61F 2002/30579; A61F 2002/4627
USPC ............................................ 623/17.11–17.16
See application file for complete search history.

(56) References Cited

U.S. PATENT DOCUMENTS

| | | | |
|---|---|---|---|
| 4,553,273 A | 11/1985 | Wu | |
| 4,636,217 A | 1/1987 | Ogilvie et al. | |
| 4,716,894 A | 1/1988 | Lazzeri et al. | |
| 4,759,769 A | 7/1988 | Hedman et al. | |
| 5,059,193 A | 10/1991 | Kuslich | |
| 5,171,278 A | 12/1992 | Pisharodi | |
| 5,228,811 A | 7/1993 | Potter | |
| 5,284,483 A | 2/1994 | Johnson et al. | |
| 5,336,223 A | 8/1994 | Rogers | |
| 5,390,683 A | 2/1995 | Pisharodi | |
| 5,522,899 A | 6/1996 | Michelson | |
| 5,554,191 A | 9/1996 | Lahille et al. | |
| 5,575,790 A | 11/1996 | Chen et al. | |
| 5,609,635 A | 3/1997 | Michelson | |
| 5,653,762 A | 8/1997 | Pisharodi | |
| 5,653,763 A | 8/1997 | Errico et al. | |
| 5,658,336 A | 8/1997 | Pisharodi | |
| 5,665,122 A | 9/1997 | Kambin | |
| 5,693,100 A | 12/1997 | Pisharodi | |
| 5,697,977 A | 12/1997 | Pisharodi | |
| 5,702,391 A | 12/1997 | Lin | |
| 5,702,453 A | 12/1997 | Rabbe et al. | |
| 5,702,455 A | 12/1997 | Saggar | |
| 5,797,918 A | 8/1998 | McGuire et al. | |
| 5,800,550 A | 9/1998 | Sertich | |
| 5,865,848 A | 2/1999 | Baker | |
| 5,893,890 A | 4/1999 | Pisharodi | |
| 5,931,777 A | 8/1999 | Sava | |
| 5,941,885 A | 8/1999 | Jackson | |
| 5,971,987 A | 10/1999 | Huxel et al. | |
| 5,980,522 A | 11/1999 | Koros et al. | |
| 6,045,579 A | 4/2000 | Hochshuler et al. | |
| 6,074,343 A | 6/2000 | Nathanson et al. | |
| 6,080,193 A | 6/2000 | Hochshuler et al. | |
| 6,099,531 A | 8/2000 | Bonutti | |
| 6,102,949 A | 8/2000 | Biedermann et al. | |
| 6,102,950 A | 8/2000 | Vaccaro | |
| 6,106,557 A | 8/2000 | Robioneck et al. | |
| 6,113,638 A | 9/2000 | Williams et al. | |
| 6,117,174 A | 9/2000 | Nolan | |
| 6,132,465 A | 10/2000 | Ray et al. | |
| 6,159,211 A | 12/2000 | Boriani et al. | |
| 6,159,244 A | 12/2000 | Suddaby | |
| 6,176,882 B1 | 1/2001 | Biedermann et al. | |
| 6,179,873 B1 | 1/2001 | Zientek | |
| 6,190,414 B1 | 2/2001 | Young et al. | |
| 6,193,757 B1 | 2/2001 | Foley et al. | |
| 6,217,579 B1 | 4/2001 | Koros | |
| 6,245,108 B1 | 6/2001 | Biscup | |
| 6,309,421 B1 | 10/2001 | Pisharodi | |
| 6,342,074 B1 | 1/2002 | Simpson | |
| 6,371,989 B1 | 4/2002 | Chauvin et al. | |
| 6,395,031 B1 | 5/2002 | Foley et al. | |
| 6,423,063 B1 | 7/2002 | Bonutti | |
| 6,432,106 B1 | 8/2002 | Fraser | |
| 6,436,140 B1 | 8/2002 | Liu et al. | |
| 6,443,989 B1 | 9/2002 | Jackson | |
| 6,443,990 B1 | 9/2002 | Aebi et al. | |
| 6,454,806 B1 | 9/2002 | Cohen et al. | |
| 6,454,807 B1 | 9/2002 | Jackson | |
| 6,461,359 B1 | 10/2002 | Tribus et al. | |
| 6,475,218 B2 | 11/2002 | Gournay et al. | |
| 6,491,724 B1 | 12/2002 | Ferree | |
| 6,520,991 B2 | 2/2003 | Huene | |
| 6,520,993 B2 | 2/2003 | James et al. | |
| 6,524,238 B2 | 2/2003 | Velikaris et al. | |
| 6,527,803 B1 | 3/2003 | Crozet et al. | |
| 6,562,074 B2 | 5/2003 | Gerbec et al. | |
| 6,576,016 B1 | 6/2003 | Hochshuler et al. | |
| 6,623,525 B2 | 9/2003 | Ralph et al. | |
| 6,629,998 B1 | 10/2003 | Lin | |
| 6,635,086 B2 | 10/2003 | Lin | |
| 6,648,917 B2 | 11/2003 | Gerbec et al. | |
| 6,676,703 B2 | 1/2004 | Biscup | |
| 6,685,742 B1 | 2/2004 | Jackson | |
| 6,723,126 B1 | 4/2004 | Berry | |
| 6,770,096 B2 | 8/2004 | Bolger et al. | |
| 6,773,460 B2 | 8/2004 | Jackson | |
| 6,821,298 B1 | 11/2004 | Jackson | |
| 6,835,206 B2 | 12/2004 | Jackson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,923,814 B1 | 8/2005 | Hildebrand et al. | |
| 6,926,737 B2 | 8/2005 | Jackson | |
| 6,953,477 B2 | 10/2005 | Berry | |
| 6,964,687 B1 | 11/2005 | Bernard et al. | |
| 6,974,480 B2 | 12/2005 | Messerli et al. | |
| 6,984,234 B2 | 1/2006 | Bray | |
| 7,112,222 B2 | 9/2006 | Fraser et al. | |
| 7,135,043 B2 | 11/2006 | Nakahara et al. | |
| 7,137,997 B2 | 11/2006 | Paul | |
| 7,172,627 B2 | 2/2007 | Fiere et al. | |
| 7,188,626 B2 | 3/2007 | Foley et al. | |
| 7,204,853 B2 | 4/2007 | Gordon et al. | |
| 7,232,464 B2 | 6/2007 | Mathieu et al. | |
| 7,238,203 B2 | 7/2007 | Bagga et al. | |
| 7,255,700 B2 | 8/2007 | Kaiser et al. | |
| 7,316,532 B2 | 1/2008 | Matthys-Mark | |
| 7,316,714 B2 | 1/2008 | Gordon et al. | |
| 7,407,483 B2 | 8/2008 | Perez-Cruet et al. | |
| 7,481,766 B2 | 1/2009 | Lee et al. | |
| 7,491,168 B2 | 2/2009 | Raymond et al. | |
| 7,537,565 B2 | 5/2009 | Bass | |
| 7,618,456 B2 | 11/2009 | Mathieu et al. | |
| 7,625,394 B2 | 12/2009 | Molz, IV et al. | |
| 7,635,366 B2 | 12/2009 | Abdou | |
| 7,637,909 B2 | 12/2009 | Lechot et al. | |
| 7,655,046 B2 | 2/2010 | Dryer et al. | |
| 7,678,148 B2 | 3/2010 | Peterman | |
| 7,703,727 B2 | 4/2010 | Selness | |
| 7,708,778 B2 | 5/2010 | Gordon et al. | |
| 7,708,779 B2 | 5/2010 | Edie et al. | |
| 7,727,280 B2 | 6/2010 | McLuen | |
| 7,753,958 B2 | 7/2010 | Gordon et al. | |
| 7,780,594 B2 | 8/2010 | Hutton | |
| 7,806,932 B2 | 10/2010 | Webb et al. | |
| 7,815,682 B1 | 10/2010 | Peterson et al. | |
| 7,819,801 B2 | 10/2010 | Miles et al. | |
| 7,824,428 B2 | 11/2010 | Mikkonen et al. | |
| 7,828,849 B2 | 11/2010 | Lim | |
| 7,846,167 B2 | 12/2010 | Garcia et al. | |
| 7,846,207 B2 | 12/2010 | Lechmann et al. | |
| 7,850,731 B2 | 12/2010 | Brittan et al. | |
| 7,850,733 B2 | 12/2010 | Baynham et al. | |
| 7,862,616 B2 | 1/2011 | Lechmann et al. | |
| 7,875,076 B2 | 1/2011 | Mathieu et al. | |
| 7,883,542 B2 | 2/2011 | Zipnick | |
| 7,892,173 B2 | 2/2011 | Miles et al. | |
| 7,909,869 B2 | 3/2011 | Gordon et al. | |
| 7,914,559 B2 | 3/2011 | Carls et al. | |
| 7,967,821 B2 | 6/2011 | Sicvol et al. | |
| 7,981,031 B2 | 7/2011 | Frasier et al. | |

(56) References Cited

U.S. PATENT DOCUMENTS

| | | |
|---|---|---|
| 8,016,836 B2 | 9/2011 | Corrao et al. |
| 8,062,375 B2 | 11/2011 | Glerum et al. |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,182,539 B2 | 5/2012 | Tyber et al. |
| 8,257,442 B2 | 9/2012 | Edie et al. |
| 8,262,570 B2 | 9/2012 | White et al. |
| 8,262,662 B2 | 9/2012 | Beardsley et al. |
| 8,262,710 B2 | 9/2012 | Freedman et al. |
| 8,287,597 B1 | 10/2012 | Pimenta et al. |
| 8,303,498 B2 | 11/2012 | Miles et al. |
| 8,303,658 B2 | 11/2012 | Peterman |
| 8,303,663 B2 | 11/2012 | Jimenez et al. |
| 8,317,866 B2 | 11/2012 | Palmatier et al. |
| 8,323,185 B2 | 12/2012 | Perez-Cruet et al. |
| 8,328,872 B2 | 12/2012 | Duffield et al. |
| 8,343,048 B2 | 1/2013 | Warren, Jr. |
| 8,353,826 B2 | 1/2013 | Weiman |
| 8,355,780 B2 | 1/2013 | Miles et al. |
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,500,749 B2 | 8/2013 | Lee et al. |
| 8,506,635 B2 | 8/2013 | Palmatier et al. |
| 8,517,935 B2 | 8/2013 | Marchek et al. |
| 8,518,120 B2 | 8/2013 | Glerum et al. |
| 8,535,380 B2 | 9/2013 | Greenhalgh et al. |
| 8,545,566 B2 | 10/2013 | Niemiec et al. |
| 8,550,994 B2 | 10/2013 | Miles et al. |
| 8,556,808 B2 | 10/2013 | Miles et al. |
| 8,556,979 B2 | 10/2013 | Glerum et al. |
| 8,579,809 B2 | 11/2013 | Parker |
| 8,579,898 B2 | 11/2013 | Prandi et al. |
| 8,579,979 B2 | 11/2013 | Edie et al. |
| 8,579,981 B2 | 11/2013 | Lim et al. |
| 8,602,984 B2 | 12/2013 | Raymond et al. |
| 8,608,785 B2 | 12/2013 | Reed et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,419 B2 | 3/2014 | Hardt et al. |
| 8,668,715 B2 | 3/2014 | Sandhu |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,285 B2 | 5/2014 | Lewis et al. |
| 8,715,353 B2 | 5/2014 | Bagga et al. |
| 8,740,983 B1 * | 6/2014 | Arnold .................. A61F 2/4611 623/17.16 |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,304 B2 | 8/2014 | Weiman et al. |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 | 9/2014 | Donahoe et al. |
| 8,845,731 B2 | 9/2014 | Weiman |
| 8,845,732 B2 | 9/2014 | Weiman |
| 8,845,734 B2 | 9/2014 | Weiman |
| 8,852,252 B2 | 10/2014 | Venturini et al. |
| 8,852,282 B2 | 10/2014 | Farley et al. |
| 8,864,833 B2 | 10/2014 | Glerum et al. |
| 8,882,813 B2 | 11/2014 | Jones et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 8,998,906 B2 | 4/2015 | Kirschman |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,548 B2 | 7/2015 | Matityahu |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,161,841 B2 | 10/2015 | Kana et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,341 B2 | 6/2016 | Gowan |
| 9,364,343 B2 | 6/2016 | Duffield et al. |
| 9,370,434 B2 | 6/2016 | Weiman |
| 9,370,435 B2 | 6/2016 | Walkenhorst et al. |
| 9,381,008 B2 | 7/2016 | Thornburg |

(56) References Cited

U.S. PATENT DOCUMENTS

| | | |
|---|---|---|
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Amin |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,468,405 B2 | 10/2016 | Miles et al. |
| 9,474,622 B2 | 10/2016 | McLaughlin et al. |
| 9,474,625 B2 | 10/2016 | Weiman |
| 9,480,573 B2 | 11/2016 | Perloff et al. |
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |
| 9,510,954 B2 | 12/2016 | Glerum et al. |
| 9,517,098 B2 | 12/2016 | Anderson |
| 9,522,070 B2 | 12/2016 | Flower et al. |
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |
| 9,585,767 B2 | 3/2017 | Robinson |
| 9,592,129 B2 | 3/2017 | Slivka et al. |
| 9,597,195 B2 | 3/2017 | Cain |
| 9,603,643 B2 | 3/2017 | Reed et al. |
| 9,603,713 B2 | 3/2017 | Moskowitz et al. |
| 9,603,717 B2 | 3/2017 | Barra et al. |
| 9,615,818 B2 | 4/2017 | Baudouin et al. |
| 9,615,936 B2 | 4/2017 | Duffield et al. |
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,763,722 B2 | 9/2017 | Roybal |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Arnin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,907,671 B2 | 3/2018 | Fessler |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,937,060 B2 * | 4/2018 | Fuhrer .................. A61F 2/442 |
| 9,943,342 B2 | 4/2018 | Tanaka et al. |
| 9,943,418 B2 | 4/2018 | Davenport et al. |
| 9,949,775 B2 | 4/2018 | Reed et al. |
| 9,949,841 B2 | 4/2018 | Glerum et al. |
| 9,956,087 B2 | 5/2018 | Seifert et al. |
| 9,962,202 B2 | 5/2018 | Anderson |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,004,608 B2 | 6/2018 | Carnes et al. |
| 10,016,282 B2 | 7/2018 | Seifert et al. |
| 10,016,284 B2 | 7/2018 | Moskowitz et al. |
| 10,022,239 B1 | 7/2018 | Entner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,771 B2 | 7/2018 | Capote et al. |
| 10,034,772 B2 | 7/2018 | Glerum et al. |
| 10,034,773 B2 | 7/2018 | McLaughlin et al. |
| 10,039,539 B2 | 8/2018 | Friedrich et al. |

(56) References Cited

U.S. PATENT DOCUMENTS

| | | |
|---|---|---|
| 10,039,650 B2 | 8/2018 | Lamborne et al. |
| 10,052,214 B2 | 8/2018 | Jimenez et al. |
| 10,058,431 B2 | 8/2018 | Tyber et al. |
| 10,060,469 B2 | 8/2018 | Jimenez et al. |
| 10,070,852 B2 | 9/2018 | Mast et al. |
| 10,076,320 B2 | 9/2018 | Mast et al. |
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |
| 10,111,758 B2 | 10/2018 | Robinson |
| 10,117,754 B2 | 11/2018 | Davenport et al. |
| 10,117,755 B2 | 11/2018 | Emerick et al. |
| 10,137,002 B2 | 11/2018 | Padovani et al. |
| 10,137,006 B2 | 11/2018 | Dewey et al. |
| 10,137,007 B2 | 11/2018 | Dewey et al. |
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,515 B2 | 1/2019 | Lee et al. |
| 10,172,652 B2 | 1/2019 | Woolley et al. |
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |
| 10,238,375 B2 | 3/2019 | O'Connell et al. |
| 10,238,383 B2 | 3/2019 | Moskowitz et al. |
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,622 B2 | 6/2019 | Brumfield et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |
| 10,327,912 B1 | 6/2019 | Suddaby |
| 10,327,917 B2 | 6/2019 | Glerum et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,633 B2 | 10/2019 | Moskowitz et al. |
| 10,426,634 B1 | 10/2019 | Al-Jazaeri et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,889 B2 | 3/2020 | Roybal |
| 10,575,960 B2 | 3/2020 | Duffield et al. |
| 10,582,959 B2 | 3/2020 | Langer et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,163 B2 | 5/2020 | Tyber et al. |
| 10,639,166 B2 | 5/2020 | Weiman et al. |
| 10,653,458 B2 | 5/2020 | Tanaka et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Neiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 | 11/2020 | Weiman et al. |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,447 B2 | 12/2020 | Tanaka et al. |
| 10,874,522 B2 | 12/2020 | Weiman |
| 10,874,523 B2 | 12/2020 | Weiman et al. |
| 10,874,524 B2 | 12/2020 | Bjork |

(56) References Cited

U.S. PATENT DOCUMENTS

| | | | |
|---|---|---|---|
| 10,881,524 B2 | 1/2021 | Eisen et al. |
| 10,881,531 B2 | 1/2021 | Berry |
| 10,888,431 B1 | 1/2021 | Robinson |
| 10,898,344 B2 | 1/2021 | Alheidt et al. |
| 10,898,346 B1 | 1/2021 | Suddaby |
| 10,925,656 B2 | 2/2021 | Cole et al. |
| 10,925,750 B2 | 2/2021 | Zappacosta et al. |
| 10,925,752 B2 | 2/2021 | Weiman |
| 10,932,920 B2 | 3/2021 | Dewey et al. |
| 10,940,014 B2 | 3/2021 | Greenhalgh |
| 10,945,858 B2 | 3/2021 | Bechtel et al. |
| 10,952,866 B2 | 3/2021 | Warren et al. |
| 10,959,855 B2 | 3/2021 | Miller et al. |
| 10,959,856 B2 | 3/2021 | Seifert et al. |
| 10,973,649 B2 | 4/2021 | Weiman et al. |
| 10,973,650 B2 | 4/2021 | Stein |
| 10,980,642 B2 | 4/2021 | Glerum et al. |
| 10,980,644 B2 | 4/2021 | Purcell et al. |
| 10,993,814 B2 | 5/2021 | Wolters |
| 11,007,067 B2 | 5/2021 | Masson et al. |
| 11,013,617 B2 | 5/2021 | Weiman et al. |
| 11,020,238 B2 | 6/2021 | Nichols et al. |
| 11,020,239 B2 | 6/2021 | Miller et al. |
| 11,026,804 B2 | 6/2021 | Jimenez et al. |
| 11,026,812 B2 | 6/2021 | Daffinson et al. |
| 11,033,401 B2 | 6/2021 | Shoshtaev |
| 11,033,402 B2 | 6/2021 | Melkent et al. |
| 11,033,404 B2 | 6/2021 | Faulhaber |
| 11,039,935 B2 | 6/2021 | McAfee |
| 11,045,326 B2 | 6/2021 | Seifert et al. |
| 11,045,327 B2 | 6/2021 | Nichols et al. |
| 11,051,949 B2 | 7/2021 | Walker et al. |
| 11,051,951 B2 | 7/2021 | Robinson et al. |
| 11,058,469 B2 | 7/2021 | Mahajan et al. |
| 11,065,127 B1 | 7/2021 | Entner et al. |
| 11,065,129 B2 | 7/2021 | Sandul |
| 11,065,130 B2 | 7/2021 | Branch et al. |
| 11,076,966 B2 | 8/2021 | Faulhaber |
| 11,083,584 B2 | 8/2021 | Lauf et al. |
| 11,083,595 B2 | 8/2021 | Robinson |
| 11,090,167 B2 | 8/2021 | Emerick et al. |
| 11,096,795 B2 | 8/2021 | Padovani et al. |
| 11,096,797 B2 | 8/2021 | Moskowitz et al. |
| 11,103,366 B2 | 8/2021 | Glerum et al. |
| RE48,719 E | 9/2021 | Suddaby et al. |
| 11,109,980 B2 | 9/2021 | Seifert et al. |
| 11,116,644 B2 | 9/2021 | Marrocco et al. |
| 11,123,198 B2 | 9/2021 | Black et al. |
| 11,123,200 B2 | 9/2021 | Faulhaber |
| 11,129,731 B2 | 9/2021 | Miller et al. |
| 11,135,071 B2 | 10/2021 | Dewey et al. |
| 11,147,680 B2 | 10/2021 | Tyber et al. |
| 11,154,404 B2 | 10/2021 | Freedman et al. |
| 11,160,666 B2 | 11/2021 | Burkhardt et al. |
| 11,160,669 B2 | 11/2021 | Rogers et al. |
| 11,166,826 B2 | 11/2021 | Huang |
| 11,173,044 B1 | 11/2021 | Jones et al. |
| 11,179,234 B2 | 11/2021 | Dacosta et al. |
| 11,285,014 B1 | 3/2022 | Josse et al. |
| 11,376,134 B1 | 7/2022 | Dewey et al. |
| 11,617,658 B2 | 4/2023 | Josse et al. |
| 11,723,780 B2 | 8/2023 | Seifert et al. |
| 11,737,892 B1 | 8/2023 | Kadaba et al. |
| 12,064,354 B2 | 8/2024 | Robinson et al. |
| 2002/0045943 A1 | 4/2002 | Uk |
| 2002/0045945 A1 | 4/2002 | Liu et al. |
| 2002/0055741 A1 | 5/2002 | Schlapfer et al. |
| 2002/0116066 A1 | 8/2002 | Chauvin et al. |
| 2002/0128713 A1 | 9/2002 | Ferree |
| 2002/0151976 A1 | 10/2002 | Foley et al. |
| 2002/0183762 A1 | 12/2002 | Anderson et al. |
| 2003/0050701 A1 | 3/2003 | Michelson |
| 2003/0130739 A1 | 7/2003 | Gerbec et al. |
| 2003/0163132 A1 | 8/2003 | Chin |
| 2004/0102778 A1 | 5/2004 | Huebner et al. |
| 2004/0172134 A1 | 9/2004 | Berry |
| 2004/0186570 A1 | 9/2004 | Rapp |
| 2004/0193158 A1 | 9/2004 | Lim et al. |
| 2004/0204713 A1 | 10/2004 | Abdou |
| 2004/0249461 A1 | 12/2004 | Ferree |
| 2004/0254643 A1 | 12/2004 | Jackson |
| 2004/0254644 A1 | 12/2004 | Taylor |
| 2005/0015094 A1 | 1/2005 | Keller |
| 2005/0015149 A1 | 1/2005 | Michelson |
| 2005/0033429 A1 | 2/2005 | Kuo |
| 2005/0033439 A1 | 2/2005 | Gordon et al. |
| 2005/0147478 A1 | 7/2005 | Greenberg |
| 2005/0154459 A1 | 7/2005 | Wolek et al. |
| 2005/0209698 A1 | 9/2005 | Gordon et al. |
| 2005/0228398 A1 | 10/2005 | Rathbun et al. |
| 2006/0122701 A1 | 6/2006 | Kiester |
| 2006/0129244 A1 | 6/2006 | Ensign |
| 2006/0260446 A1 | 11/2006 | Chang |
| 2006/0276901 A1 | 12/2006 | Zipnick et al. |
| 2007/0173840 A1 | 7/2007 | Huebner |
| 2007/0218750 A1 | 9/2007 | Corrao et al. |
| 2007/0233150 A1 | 10/2007 | Blain et al. |
| 2007/0270859 A1 | 11/2007 | Companioni et al. |
| 2008/0058804 A1 | 3/2008 | Lechot et al. |
| 2008/0132959 A1 | 6/2008 | Mikkonen et al. |
| 2008/0140207 A1 | 6/2008 | Olmos et al. |
| 2008/0287957 A1 | 11/2008 | Hester et al. |
| 2009/0024158 A1 | 1/2009 | Viker |
| 2009/0036746 A1 | 2/2009 | Blackwell et al. |
| 2009/0093830 A1 | 4/2009 | Miller |
| 2009/0105834 A1 | 4/2009 | Hovda et al. |
| 2009/0292361 A1 | 11/2009 | Lopez |
| 2010/0070035 A1 | 3/2010 | Mayer |
| 2010/0076440 A1 | 3/2010 | Pamichev et al. |
| 2010/0082109 A1 | 4/2010 | Greenhalgh et al. |
| 2010/0114183 A1 | 5/2010 | Wassinger et al. |
| 2010/0152853 A1 | 6/2010 | Kirschman |
| 2010/0191336 A1 | 7/2010 | Greenhalgh |
| 2010/0211176 A1 | 8/2010 | Greenhalgh |
| 2010/0280617 A1 | 11/2010 | Coppes et al. |
| 2010/0286777 A1 | 11/2010 | Errico et al. |
| 2011/0118843 A1 | 5/2011 | Mathieu et al. |
| 2011/0130838 A1 | 6/2011 | Morgenstern Lopez |
| 2011/0144755 A1 | 6/2011 | Baynham et al. |
| 2011/0153020 A1 | 6/2011 | Abdelgany et al. |
| 2011/0218572 A1 | 9/2011 | Lechmann et al. |
| 2011/0218631 A1 | 9/2011 | Woodburn, Sr. et al. |
| 2011/0237898 A1 | 9/2011 | Stone et al. |
| 2011/0301577 A1 | 12/2011 | Simmen et al. |
| 2012/0004732 A1 | 1/2012 | Goel et al. |
| 2012/0010717 A1 | 1/2012 | Spann |
| 2012/0095515 A1 | 4/2012 | Hamilton |
| 2012/0101581 A1 | 4/2012 | Mathieu et al. |
| 2012/0109142 A1 | 5/2012 | Dayan |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0143195 A1 | 6/2012 | Sander |
| 2012/0150237 A1 | 6/2012 | Combrowski |
| 2012/0197401 A1 | 8/2012 | Duncan et al. |
| 2012/0209385 A1 | 8/2012 | Aferzon |
| 2012/0215313 A1 | 8/2012 | Saidha et al. |
| 2012/0215316 A1 | 8/2012 | Mohr et al. |
| 2012/0232349 A1 | 9/2012 | Perrow |
| 2013/0103095 A1* | 4/2013 | Brumfield ......... A61B 17/7064 606/301 |
| 2013/0158664 A1 | 6/2013 | Palmatier et al. |
| 2013/0184823 A1 | 7/2013 | Malberg |
| 2013/0190876 A1 | 7/2013 | Drochner et al. |
| 2013/0211526 A1 | 8/2013 | Alheidt et al. |
| 2013/0226191 A1 | 8/2013 | Thoren et al. |
| 2013/0231747 A1 | 9/2013 | Olmos et al. |
| 2013/0274557 A1 | 10/2013 | Bowman et al. |
| 2013/0304136 A1 | 11/2013 | Gourlaouen-Preissler et al. |
| 2013/0317312 A1 | 11/2013 | Eastlack et al. |
| 2014/0018816 A1 | 1/2014 | Fenn et al. |
| 2014/0039622 A1 | 2/2014 | Glerum et al. |

(56) References Cited

U.S. PATENT DOCUMENTS

| | | |
|---|---|---|
| 2014/0107790 A1 | 4/2014 | Combrowski |
| 2014/0114321 A1 | 4/2014 | Davenport et al. |
| 2014/0114420 A1 | 4/2014 | Robinson |
| 2014/0148904 A1 | 5/2014 | Robinson |
| 2014/0163682 A1 | 6/2014 | Iott et al. |
| 2014/0180419 A1 | 6/2014 | Dmuschewsky |
| 2014/0194992 A1 | 7/2014 | Medina |
| 2014/0249629 A1 | 9/2014 | Moskowitz et al. |
| 2014/0249631 A1 | 9/2014 | Weiman |
| 2014/0277471 A1 | 9/2014 | Gray et al. |
| 2014/0277473 A1 | 9/2014 | Perrow |
| 2014/0277487 A1 | 9/2014 | Davenport et al. |
| 2014/0277500 A1 | 9/2014 | Logan et al. |
| 2014/0303674 A1 | 10/2014 | Sasing |
| 2014/0364855 A1 | 12/2014 | Stoll et al. |
| 2014/0379085 A1 | 12/2014 | Duffield et al. |
| 2015/0173915 A1 | 6/2015 | Laubert et al. |
| 2015/0223945 A1 | 8/2015 | Weiman et al. |
| 2015/0230931 A1 | 8/2015 | Greenhalgh |
| 2015/0238236 A1 | 8/2015 | Sasing |
| 2015/0354635 A1 | 12/2015 | McClymont et al. |
| 2015/0374507 A1 | 12/2015 | Wolters et al. |
| 2016/0008924 A1 | 1/2016 | Canourgues et al. |
| 2016/0022434 A1 | 1/2016 | Robinson |
| 2016/0051373 A1 | 2/2016 | Faulhaber |
| 2016/0058571 A1 | 3/2016 | McLaughlin et al. |
| 2016/0081681 A1 | 3/2016 | Waugh et al. |
| 2016/0089247 A1 | 3/2016 | Nichols et al. |
| 2016/0095710 A1 | 4/2016 | Juszczyk et al. |
| 2016/0095718 A1 | 4/2016 | Burkhardt et al. |
| 2016/0100951 A1* | 4/2016 | Suddaby ............... A61F 2/442 623/17.16 |
| 2016/0128847 A1 | 5/2016 | Kurtaliaj et al. |
| 2016/0199073 A1 | 7/2016 | Nino et al. |
| 2016/0242930 A1 | 8/2016 | Duffield et al. |
| 2016/0256291 A1 | 9/2016 | Miller |
| 2016/0278830 A1 | 9/2016 | Arrington |
| 2016/0296340 A1 | 10/2016 | Gordon et al. |
| 2016/0310291 A1 | 10/2016 | Greenhalgh |
| 2016/0345952 A1 | 12/2016 | Kucharzyk et al. |
| 2016/0367377 A1 | 12/2016 | Faulhaber |
| 2017/0010025 A1 | 1/2017 | Mayershofer |
| 2017/0029635 A1 | 2/2017 | Doll et al. |
| 2017/0035406 A1 | 2/2017 | Abidin et al. |
| 2017/0049651 A1 | 2/2017 | Lim et al. |
| 2017/0049653 A1 | 2/2017 | Lim et al. |
| 2017/0095345 A1 | 4/2017 | Davenport et al. |
| 2017/0100255 A1 | 4/2017 | Hleihil et al. |
| 2017/0100257 A1 | 4/2017 | Weiman et al. |
| 2017/0105844 A1 | 4/2017 | Kuyler et al. |
| 2017/0112630 A1 | 4/2017 | Kuyler et al. |
| 2017/0151065 A1 | 6/2017 | Warren et al. |
| 2017/0156882 A1 | 6/2017 | Rathbun et al. |
| 2017/0156884 A1 | 6/2017 | Rathbun et al. |
| 2017/0189200 A1 | 7/2017 | Miller et al. |
| 2017/0189204 A1 | 7/2017 | Riemhofer et al. |
| 2017/0202678 A1 | 7/2017 | Duffield et al. |
| 2017/0215856 A1 | 8/2017 | Martinelli et al. |
| 2017/0224502 A1 | 8/2017 | Wolters et al. |
| 2017/0224504 A1 | 8/2017 | Butler et al. |
| 2017/0231675 A1 | 8/2017 | Combrowski |
| 2017/0231780 A1 | 8/2017 | D'Urso |
| 2017/0246006 A1 | 8/2017 | Carnes et al. |
| 2017/0290677 A1 | 10/2017 | Olmos et al. |
| 2017/0296352 A1 | 10/2017 | Richerme et al. |
| 2017/0333200 A1 | 11/2017 | Arnin |
| 2017/0367842 A1 | 12/2017 | Predick et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0000606 A1 | 1/2018 | Hessler et al. |
| 2018/0030362 A1 | 2/2018 | Kosler et al. |
| 2018/0031810 A1 | 2/2018 | Hsu et al. |
| 2018/0036136 A1 | 2/2018 | Duffield et al. |
| 2018/0036138 A1 | 2/2018 | Robinson |
| 2018/0104066 A1 | 4/2018 | Bae et al. |
| 2018/0116819 A1 | 5/2018 | Maguire et al. |
| 2018/0116891 A1 | 5/2018 | Beale et al. |
| 2018/0193160 A1 | 7/2018 | Hsu et al. |
| 2018/0193164 A1 | 7/2018 | Shoshtaev |
| 2018/0206999 A1 | 7/2018 | Suddaby |
| 2018/0256356 A1 | 9/2018 | Robinson et al. |
| 2018/0256359 A1 | 9/2018 | Greenhalgh |
| 2018/0256360 A1 | 9/2018 | Cain |
| 2018/0256362 A1 | 9/2018 | Slivka et al. |
| 2018/0263784 A1 | 9/2018 | Bechtel et al. |
| 2018/0271513 A1 | 9/2018 | Perrow et al. |
| 2018/0280142 A1 | 10/2018 | Schultz et al. |
| 2018/0303473 A1 | 10/2018 | Spann et al. |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1 | 11/2018 | Engstrom |
| 2018/0318102 A1 | 11/2018 | Seifert et al. |
| 2018/0325574 A1 | 11/2018 | Bjork et al. |
| 2018/0338838 A1 | 11/2018 | Cryder et al. |
| 2018/0338841 A1 | 11/2018 | Miller et al. |
| 2018/0344307 A1 | 12/2018 | Hynes et al. |
| 2018/0360616 A1 | 12/2018 | Luu |
| 2019/0000640 A1 | 1/2019 | Weiman |
| 2019/0000702 A1 | 1/2019 | Lim et al. |
| 2019/0000707 A1 | 1/2019 | Lim et al. |
| 2019/0020121 A1 | 1/2019 | Paulotto et al. |
| 2019/0021716 A1 | 1/2019 | Waugh et al. |
| 2019/0021873 A1 | 1/2019 | Dmuschewsky |
| 2019/0046329 A1 | 2/2019 | Padovani et al. |
| 2019/0046381 A1 | 2/2019 | Lim et al. |
| 2019/0046383 A1 | 2/2019 | Lim et al. |
| 2019/0060083 A1 | 2/2019 | Weiman et al. |
| 2019/0082949 A1 | 3/2019 | Weiman |
| 2019/0083081 A1 | 3/2019 | Ortiz et al. |
| 2019/0091033 A1 | 3/2019 | Dewey et al. |
| 2019/0105175 A1 | 4/2019 | Zappacosta et al. |
| 2019/0125328 A1 | 5/2019 | Blain |
| 2019/0133434 A1 | 5/2019 | Lee et al. |
| 2019/0133645 A1 | 5/2019 | Gordon et al. |
| 2019/0133779 A1 | 5/2019 | McLaughlin et al. |
| 2019/0133780 A1 | 5/2019 | Matthews et al. |
| 2019/0133784 A1 | 5/2019 | Gunn et al. |
| 2019/0133788 A1 | 5/2019 | Weiman et al. |
| 2019/0142480 A1 | 5/2019 | Woolley et al. |
| 2019/0151115 A1 | 5/2019 | Nichols et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0209155 A1 | 7/2019 | Mast et al. |
| 2019/0216453 A1 | 7/2019 | Predick et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0247098 A1 | 8/2019 | Brumfield et al. |
| 2019/0254650 A1 | 8/2019 | Martinelli et al. |
| 2019/0254838 A1 | 8/2019 | Miller et al. |
| 2019/0254839 A1 | 8/2019 | Nichols et al. |
| 2019/0262009 A1 | 8/2019 | Cheng |
| 2019/0262139 A1 | 8/2019 | Wolters |
| 2019/0269521 A1 | 9/2019 | Shoshtaev |
| 2019/0274670 A1 | 9/2019 | O'Connell et al. |
| 2019/0274671 A1 | 9/2019 | Lauf et al. |
| 2019/0274836 A1 | 9/2019 | Eisen et al. |
| 2019/0282373 A1 | 9/2019 | Alheidt |
| 2019/0290446 A1 | 9/2019 | Masson et al. |
| 2019/0290447 A1 | 9/2019 | Stein |
| 2019/0298416 A1 | 10/2019 | Rezach |
| 2019/0298524 A1 | 10/2019 | Lauf et al. |
| 2019/0298540 A1 | 10/2019 | Aghayev et al. |
| 2019/0321022 A1 | 10/2019 | Karpowicz et al. |
| 2019/0321190 A1 | 10/2019 | Wagner et al. |
| 2019/0328539 A1 | 10/2019 | Suh et al. |
| 2019/0328540 A1 | 10/2019 | Seifert et al. |
| 2019/0329388 A1 | 10/2019 | Erickson et al. |
| 2019/0336301 A1 | 11/2019 | Engstrom |
| 2019/0336304 A1 | 11/2019 | Burkhardt et al. |
| 2019/0350573 A1 | 11/2019 | Vogel et al. |

(56) References Cited

U.S. PATENT DOCUMENTS

| | | |
|---|---|---|
| 2019/0358049 A1 | 11/2019 | Faulhaber |
| 2019/0358050 A1 | 11/2019 | Fessler |
| 2019/0358051 A1 | 11/2019 | Flower et al. |
| 2019/0380840 A1 | 12/2019 | Tyber et al. |
| 2019/0388232 A1 | 12/2019 | Purcell et al. |
| 2020/0008951 A1 | 1/2020 | McClintock et al. |
| 2020/0030114 A1 | 1/2020 | Cain |
| 2020/0030116 A1 | 1/2020 | Jimenez et al. |
| 2020/0038200 A1 | 2/2020 | Foley et al. |
| 2020/0054461 A1 | 2/2020 | Marrocco et al. |
| 2020/0060844 A1 | 2/2020 | Mathieu et al. |
| 2020/0069316 A1 | 3/2020 | DeSoutter et al. |
| 2020/0078190 A1 | 3/2020 | Rogers et al. |
| 2020/0093526 A1 | 3/2020 | Daly et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0107824 A1 | 4/2020 | Fleischer |
| 2020/0129306 A1 | 4/2020 | Miller et al. |
| 2020/0129307 A1 | 4/2020 | Hunziker et al. |
| 2020/0138591 A1 | 5/2020 | Moskowitz et al. |
| 2020/0138593 A1 | 5/2020 | Martynova et al. |
| 2020/0146840 A1 | 5/2020 | Black et al. |
| 2020/0179120 A1 | 6/2020 | Bielenstein et al. |
| 2020/0205993 A1 | 7/2020 | Davenport et al. |
| 2020/0214754 A1 | 7/2020 | Bowen et al. |
| 2020/0222202 A1 | 7/2020 | Kuyler et al. |
| 2020/0229944 A1 | 7/2020 | Suh et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0281741 A1 | 9/2020 | Grotz |
| 2020/0289287 A1 | 9/2020 | Emerick et al. |
| 2020/0297507 A1 | 9/2020 | Iott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390433 A1 | 12/2020 | Yu et al. |
| 2020/0390565 A1 | 12/2020 | Jimenez et al. |
| 2020/0397593 A1 | 12/2020 | Davenport et al. |
| 2020/0405497 A1 | 12/2020 | Olmos et al. |
| 2020/0405498 A1 | 12/2020 | Gray et al. |
| 2020/0405499 A1 | 12/2020 | Gerbec et al. |
| 2020/0405500 A1 | 12/2020 | Cain |
| 2021/0007860 A1 | 1/2021 | Glerum et al. |
| 2021/0015626 A1 | 1/2021 | Suddaby |
| 2021/0030555 A1 | 2/2021 | Weiman et al. |
| 2021/0030561 A1 | 2/2021 | Gleason |
| 2021/0045891 A1 | 2/2021 | Rogers et al. |
| 2021/0045892 A1 | 2/2021 | Rogers et al. |
| 2021/0052395 A1 | 2/2021 | Tott et al. |
| 2021/0068959 A1 | 3/2021 | McLuen et al. |
| 2021/0068974 A1 | 3/2021 | Cowan et al. |
| 2021/0068982 A1 | 3/2021 | Cames et al. |
| 2021/0077271 A1 | 3/2021 | Sharabani |
| 2021/0077272 A1 | 3/2021 | Eisen et al. |
| 2021/0085479 A1 | 3/2021 | Weiman et al. |
| 2021/0093462 A1 | 4/2021 | Lucasiewicz et al. |
| 2021/0106434 A1 | 4/2021 | Alheidt et al. |
| 2021/0113349 A1 | 4/2021 | Weiman et al. |
| 2021/0121299 A1 | 4/2021 | Hyder |
| 2021/0121300 A1 | 4/2021 | Weiman et al. |
| 2021/0137697 A1 | 5/2021 | Weiman |
| 2021/0137699 A1 | 5/2021 | Jang et al. |
| 2021/0137701 A1 | 5/2021 | Miller et al. |
| 2021/0154811 A1 | 5/2021 | Spreiter et al. |
| 2021/0161678 A1 | 6/2021 | Dewey et al. |
| 2021/0177618 A1 | 6/2021 | Branch et al. |
| 2021/0186706 A1 | 6/2021 | Spitler et al. |
| 2021/0186709 A1 | 6/2021 | Weiman et al. |
| 2021/0196470 A1 | 7/2021 | Shoshtaev |
| 2021/0205092 A1 | 7/2021 | Glerum et al. |
| 2021/0205094 A1 | 7/2021 | Weiman et al. |
| 2021/0220145 A1 | 7/2021 | Stein |
| 2021/0220147 A1 | 7/2021 | Berry |
| 2021/0236298 A1 | 8/2021 | Weiman et al. |
| 2021/0251770 A1 | 8/2021 | Purcell et al. |
| 2021/0251776 A1 | 8/2021 | Daffinson et al. |
| 2021/0259848 A1 | 8/2021 | Kang et al. |
| 2021/0259849 A1 | 8/2021 | Robinson et al. |
| 2021/0259850 A1 | 8/2021 | Eisen et al. |
| 2021/0267767 A1 | 9/2021 | Stein |
| 2021/0275317 A1 | 9/2021 | Spetzger |
| 2021/0275318 A1 | 9/2021 | Reimels |
| 2021/0275319 A1 | 9/2021 | Reimels |
| 2021/0275321 A1 | 9/2021 | Seifert et al. |
| 2021/0282938 A1 | 9/2021 | Nichols et al. |
| 2021/0298915 A1 | 9/2021 | Faulhaber |
| 2021/0298916 A1 | 9/2021 | Melkent et al. |
| 2021/0307920 A1 | 10/2021 | Walker et al. |
| 2021/0315705 A1 | 10/2021 | Altarac et al. |
| 2021/0322179 A1 | 10/2021 | Miller et al. |
| 2021/0322181 A1 | 10/2021 | Predick |
| 2021/0322182 A1 | 10/2021 | Faulhaber |
| 2021/0330472 A1 | 10/2021 | Shoshtaev |
| 2021/0346174 A1 | 11/2021 | Flint et al. |
| 2021/0353277 A1 | 11/2021 | Gregersen et al. |
| 2021/0401586 A1* | 12/2021 | Zakelj ............... A61F 2/4455 |
| 2022/0015924 A1 | 1/2022 | Freedman et al. |
| 2022/0047312 A1 | 2/2022 | Seykora et al. |
| 2022/0087819 A1 | 3/2022 | Robinson et al. |
| 2022/0133336 A1 | 5/2022 | Tsai et al. |
| 2022/0133497 A1 | 5/2022 | Dewey et al. |
| 2022/0133498 A1 | 5/2022 | Josse et al. |
| 2022/0133499 A1 | 5/2022 | Josse et al. |
| 2022/0218325 A1 | 7/2022 | Josse |
| 2022/0265256 A1 | 8/2022 | Villamil et al. |
| 2022/0313450 A1 | 10/2022 | Donohoe et al. |
| 2022/0387184 A1 | 12/2022 | Josse et al. |
| 2022/0409397 A1 | 12/2022 | Hayes et al. |
| 2023/0015512 A1 | 1/2023 | Eisen et al. |
| 2023/0027836 A1 | 1/2023 | Predick et al. |
| 2023/0137358 A1 | 5/2023 | Hayes et al. |

FOREIGN PATENT DOCUMENTS

| | | |
|---|---|---|
| EP | 0 767 636 A1 | 4/1997 |
| EP | 0 880 950 A1 | 12/1998 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| EP | 2954860 A2 | 12/2015 |
| EP | 3031424 A1 | 6/2016 |
| EP | 3 069 694 A1 | 9/2016 |
| EP | 3213720 A1 | 9/2017 |
| FR | 2781998 A1 | 2/2000 |
| FR | 3082115 A1 | 12/2019 |
| GB | 2 377 387 A | 1/2003 |
| KR | 102117224 B1 | 6/2020 |
| KR | 102192022 B1 | 12/2020 |
| WO | 92/14423 A1 | 9/1992 |
| WO | 97/ 00054 A1 | 1/1997 |
| WO | 99/26562 A1 | 6/1999 |
| WO | 99/66867 A1 | 12/1999 |
| WO | 00/12033 A1 | 3/2000 |
| WO | 00/25706 A1 | 5/2000 |
| WO | 00/49977 A1 | 8/2000 |
| WO | 02/19952 A1 | 3/2002 |
| WO | 03/105673 A2 | 12/2003 |
| WO | 2006116850 A1 | 11/2006 |
| WO | 2012139022 A2 | 10/2012 |
| WO | 2014/133755 A1 | 9/2014 |

(56) References Cited

FOREIGN PATENT DOCUMENTS

| WO | 2015063721 A1 | 5/2015 |
|---|---|---|
| WO | 2015198335 A1 | 12/2015 |
| WO | 2016057940 A1 | 4/2016 |
| WO | 2016/205607 A1 | 12/2016 |
| WO | 2017/168208 A1 | 10/2017 |
| WO | 2018049227 A1 | 3/2018 |
| WO | 2021055323 A1 | 3/2021 |

OTHER PUBLICATIONS

International Search Report and Written Opinion in Application No. PCT/US2022/030094 dated Sep. 16, 2022.
International Search Report, and Written Opinion for Application. No. PCT/US2019/019067, dated Jun. 3, 2019.
International Search Report and Written Opinion for Application No. PCT/US2019/019060, dated Jun. 5, 2019.
International Search Report and Written Opinion, PCT/IB2020/000932, dated Jul. 29, 2021.
International Search Report and Written Opinion, PCT/IB2020/000942, dated Aug. 10, 2021.
European Search Report, EP19756905, dated Oct. 18, 2021.
International Search Report and Written Opinion in Application No. PCT/IB2023/058417 dated Dec. 7, 2023.
International Search Report and Written Opinion in Application No. PCT/IB2023/057720 dated Nov. 8, 2023.
International Search Report and Written Opinion in Application No. PCT/US2022/027200 dated Aug. 19, 2022.
International Search Report and Written Opinion in Application No. PCT/US2022/016831 dated Sep. 29, 2022.
Chinese Office Action in Application No. 201980010758.4 dated Jun. 16, 2023.
International Search Report and Written Opinion in Application No. PCT/US2022/016809 dated Jul. 27, 2022.
International Search Report and Written Opinion in Application No. PCT/US2022/027695 dated Jul. 27, 2022.
European Search Report in Application No. 22828961.7 dated Mar. 14, 2025.
International Search Report and Written Opinion in Application No. PCT/IB2024/054985 dated Sep. 10, 2024.

\* cited by examiner

100

100

100

100

100

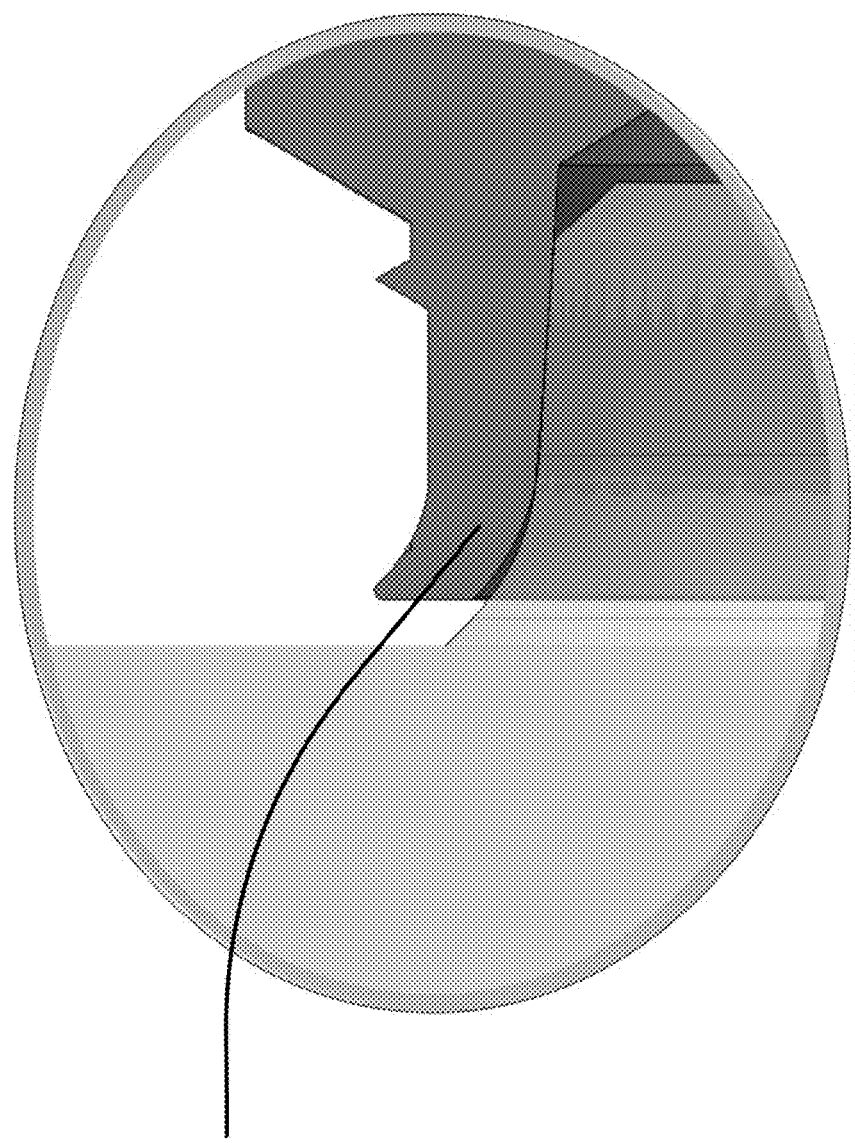
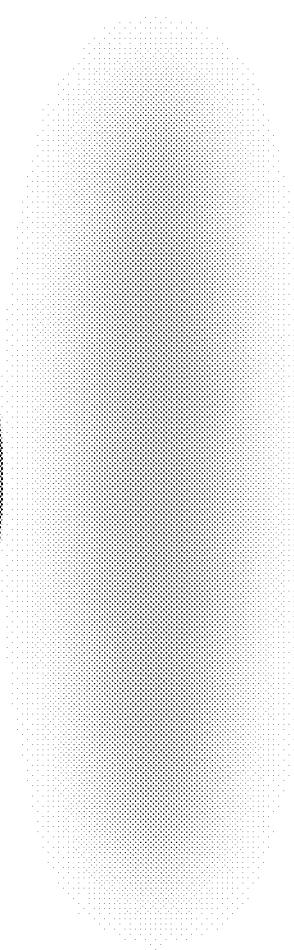
FIG. 41
499

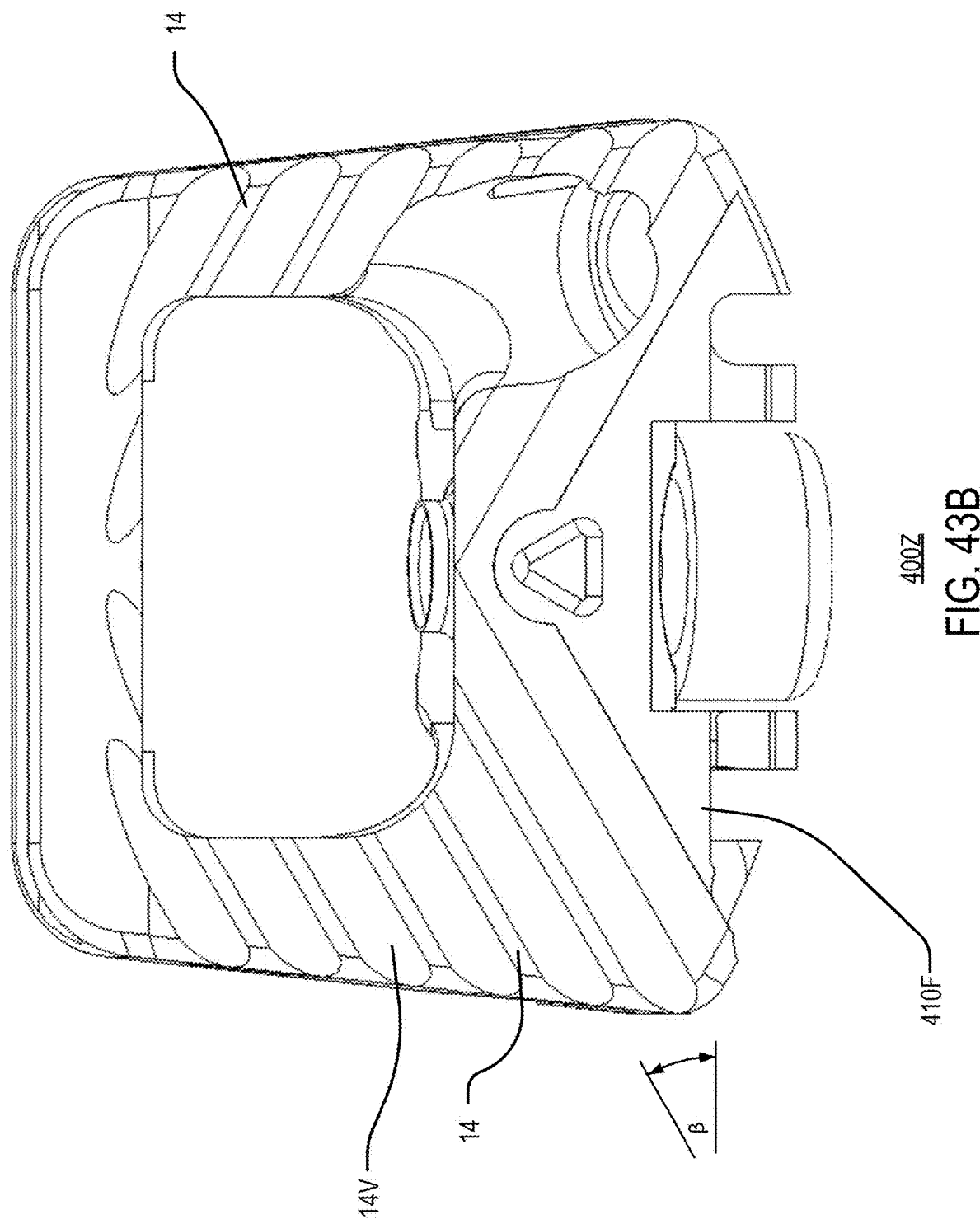

EXPANDABLE INTERBODY IMPLANT AND CORRESPONDING SURGICAL TOOL

CROSS-REFERENCE TO RELATED APPLICATIONS

This application is a continuation in part of: U.S. patent application Ser. No. 17/665,449, titled EXPANDABLE IMPLANT AND CORRESPONDING INSERTER, filed Feb. 4, 2022; U.S. patent application Ser. No. 17/515,709, titled EXPANDABLE IMPLANT AND CORRESPONDING INSERTER, filed Nov. 1, 2021; and U.S. patent application Ser. No. 17/356,950, titled EXPANDABLE INTERBODY IMPLANT, filed Jun. 24, 2021 the entire disclosure of each application is incorporated herein by reference. This application also incorporates by reference U.S. application Ser. No. 17/307,578, titled EXTERNALLY DRIVEN EXPANDABLE INTERBODY AND RELATED METHODS, filed May 5, 2021; U.S. Pat. No. 11,096,796, titled INTERBODY SPINAL IMPLANT HAVING A ROUGHENED SURFACE TOPOGRAPHY ON ONE OR MORE INTERNAL SURFACES, and filed on Mar. 4, 2013; and U.S. Pat. No. 10,821,000, titled TITANIUM IMPLANT SURFACES FREE FROM ALPHA CASE AND WITH ENHANCED OSTEOINDUCTION, and filed Jun. 29, 2017.

FIELD

In one aspect, the present technology is generally related to an externally driven expandable interbody implant for use in a medical procedure related to the spine. In some embodiments, disclosed implants may be used in an anterior cervical discectomy and fusion (ACDF) procedure although other uses in other areas of the spine or between two bones are also contemplated.

BACKGROUND

Mechanically operated interbody implants may be used to align and/or realign a patient's spine during a medical procedure and/or for purposes of fusion, degenerative tissue and/or trauma/repair procedures. Conventional implants designed for the Thoracic and Lumbar region of the spine often include top and bottom endplates and a mechanical means to separate the top and bottom endplates. The mechanical mechanisms to separate the top and bottom endplates are often cumbersome and require a large footprint that is often unsuitable, for example, for ACDF type surgeries of the cervical portion of the spine. Many currently available ACDF type implants may be limited in an ability to optimize the adjustment of lordosis or sagittal alignment of the vertebral bodies because they may rely on a fixed lordotic angle between the superior/cephalad and inferior/caudad faces of the device.

SUMMARY

The techniques of this disclosure generally relate to an expandable interbody implant including a superior endplate and an inferior endplate hingedly coupled and which may further include a locking element to secure the inferior endplate and superior endplate in a particular configuration, for example. The superior and inferior endplates may be moved in a multitude of expanded and/or lordosed or kyphosed or otherwise angled configurations via an external inserter for example. In various embodiments, a locking screw may be a breakoff type screw. In various embodiments at least one breakoff tang on the implant may be used to for gripping of the implant to insert it into a disc space and afterwards the breakoff tang may be broken off and removed. Additionally, in various embodiments the locking screw may be used to grip the implant and insert it into a disc space. Additionally, in various embodiments female recesses, rather than tangs (or male bosses/protrusions), may be used for gripping of the implant and inserting the implant into a disc space.

In one aspect, the present disclosure provides for an expandable implant movable between a contracted position (closed position) and an expanded position, for example. The expandable implant may include an expandable body extending from a proximal end to a distal end in a proximal-to-distal direction (may also be referred to as an anterior-to-posterior direction depending on surgical technique), extending from a first lateral side to a second lateral side in a widthwise direction, and extend from a superior endplate to an inferior endplate in a heightwise direction (may also be referred to as a cephalad-to-caudal and/or vertical direction depending on surgical technique), for example. In various embodiments, the expandable body may be defined by a superior endplate and an inferior endplate that are hingedly connected, for example. In various embodiments, the superior endplate includes a first core having a distal engagement surface (may also be referred to as a posterior engagement surface depending on surgical technique) and the inferior endplate includes a second core having a proximal engagement surface (may also be referred to as an anterior engagement surface) and a threaded screw aperture, for example. In various embodiments, disclosed implants may include a threaded breakoff screw having a fracture surface that is disposed in the threaded screw aperture and movable between a locked position and an unlocked position, for example. In various embodiments, when in the locked position, the breakoff screw urges the distal engagement surface of the first core into direct contact with the proximal engagement surface of the second core, for example.

In another aspect, the disclosure provides for a system including a medical implant and a surgical tool, for example. The system may include an expandable implant movable between a contracted position and an expanded position, for example. In various embodiments, the expanded position may also refer to a distracted and angled orientation of the superior endplate and inferior endplate. The expandable implant may include an expandable body extending from a proximal end to a distal end in a proximal-to-distal direction and extending from a first lateral side to a second lateral side in a widthwise direction, for example. In various embodiments, the expandable body may be defined by a superior endplate and an inferior endplate that are hingedly connected, for example. In various embodiments, the superior endplate includes a first core having a distal engagement surface and the inferior endplate includes a second core having a proximal engagement surface and a threaded screw aperture, for example. In various embodiments, disclosed implants may include a locking screw that is disposed in the threaded screw aperture and movable between a locked position and an unlocked position, for example. In various embodiments, when in the locked position, the locking screw urges the distal engagement surface of the first core into direct contact with the proximal engagement surface of the second core, for example. The system may also include a surgical tool for expanding the implant and tightening the locking screw while the implant is expanded at a desired height, position, and/or angle.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 29 is a reference drawing showing the human spine of which various disclosed implant embodiments may be installed in.

FIG. 41 is an enlarged view of region S-W of FIG. 40.

FIG. 43B is a top down view of an implant having angled engagement features.

DETAILED DESCRIPTION

Figure 1:
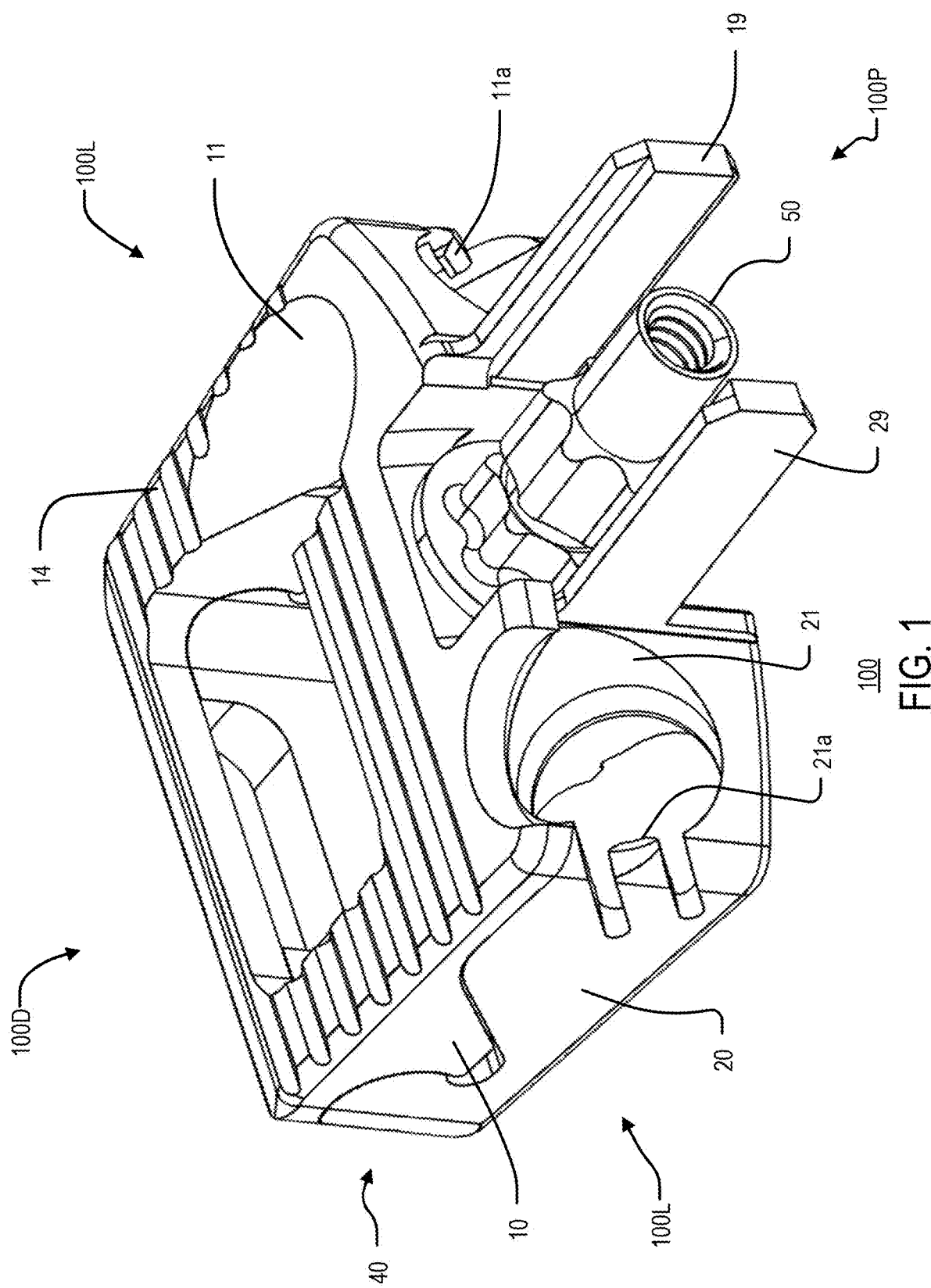
FIG. 1 is a perspective view of an expandable implant.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring to FIGS. 1-43 generally, various embodiments and views of an expandable implant 100 are disclosed. The components of expandable implant 100 can be fabricated from biologically acceptable materials suitable for medical applications, including metals, synthetic polymers, ceramics and bone material and/or their composites. For example, the components, individually or collectively, can be fabricated from materials such as stainless steel alloys, commercially pure titanium, titanium alloys, Grade 5 titanium, superelastic titanium alloys, cobalt-chrome alloys, superelastic metallic alloys (e.g., Nitinol, super elasto-plastic metals, such as GUM METAL™), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe, polylactic acid or polylactide and their combinations.

In various embodiments, components may be coated with a ceramic, titanium, and/or other biocompatible material to provide surface texturing at (a) the macro scale, (b) the micro scale, and/or (c) the nano scale, for example. Similarly, components may undergo a subtractive manufacturing process providing for surface texturing configured to facilitate osseointegration and cellular attachment and osteoblast maturation. Example surface texturing of additive and subtractive manufacturing processes may comprise (a) macroscale structural features having a maximum peak-to-valley height of about 40 microns to about 500 microns, (b) micro-scale structural features having a maximum peak-to-valley height of about 2 microns to about 40 microns, and/or (c) nano-scale structural features having a maximum peak-to-valley height of about 0.05 microns to about 5 microns. In various embodiments, the three types of structural features may be overlapping with one another, for example. Additionally, such surface texturing may be applied to any surface, e.g., both external exposed facing surfaces of components and internal non exposed surfaces of components. Further discussion regarding relevant surface texturing and coatings is described in, for example, U.S. Pat. No. 11,096, 796, titled Interbody spinal implant having a roughened surface topography on one or more internal surfaces, and filed on Mar. 4, 2013—the entire disclosure of which is incorporated herein by reference in its entirety. Accordingly, it shall be understood that any of the described coating and texturing processes of U.S. Pat. No. 11,096,796, may be applied to any component of the various embodiments disclosed herein, e.g., the exposed surfaces and internal surfaces of endplates. Another example technique for manufacturing an orthopedic implant having surfaces with osteoinducting roughness features including micro-scale structures and nano-scale structures is disclosed in U.S. Pat. No. 10,821,000, the entire contents of which are incorporated herein by reference. Additionally, an example of a commercially available product may be the Adaptix™ Interbody System sold by Medtronic Spine and comprising a titanium cage made with Titan nanoLOCK™.

Figure 2:
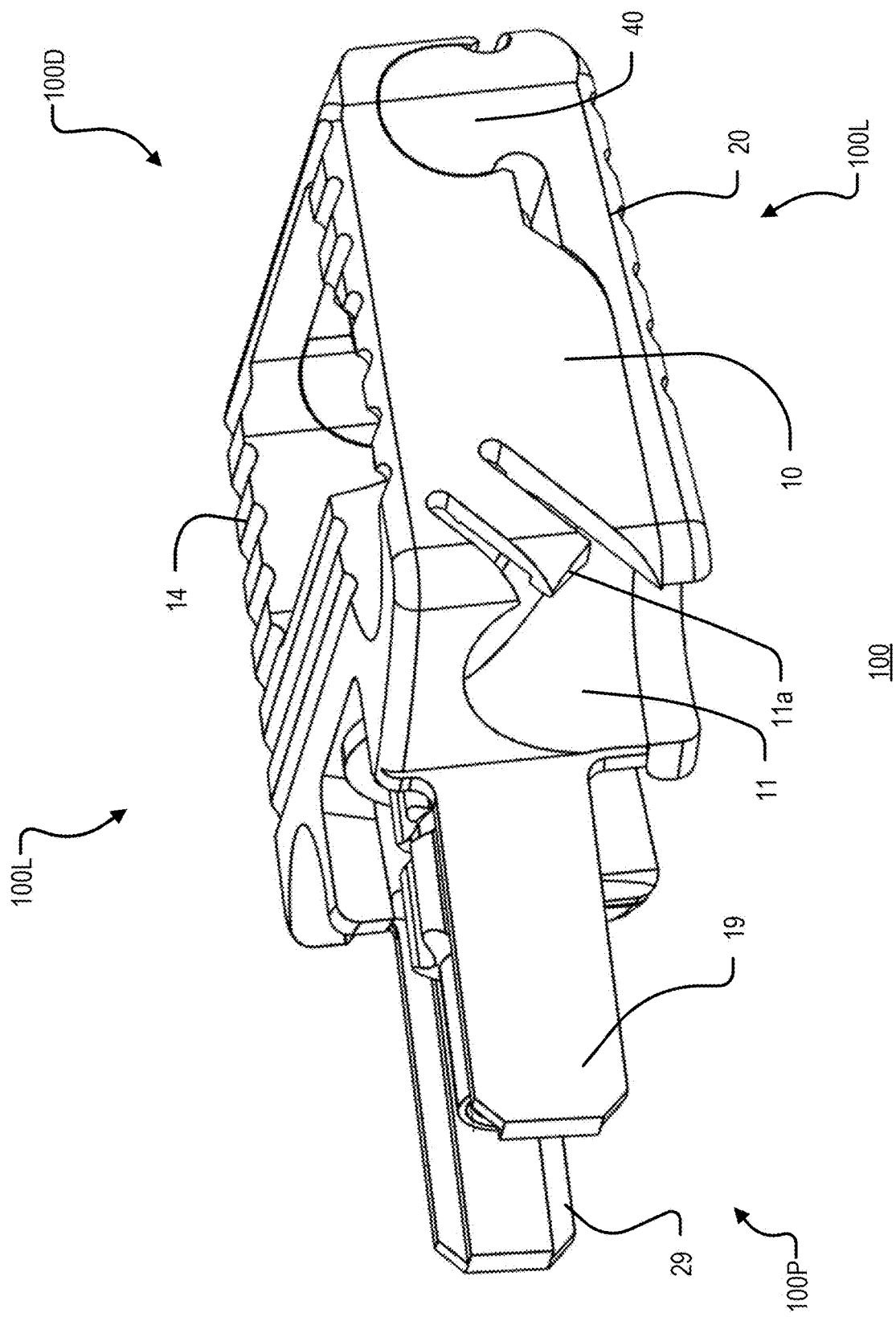
FIG. 2 is an alternate perspective view of an expandable implant.
Figure 3:
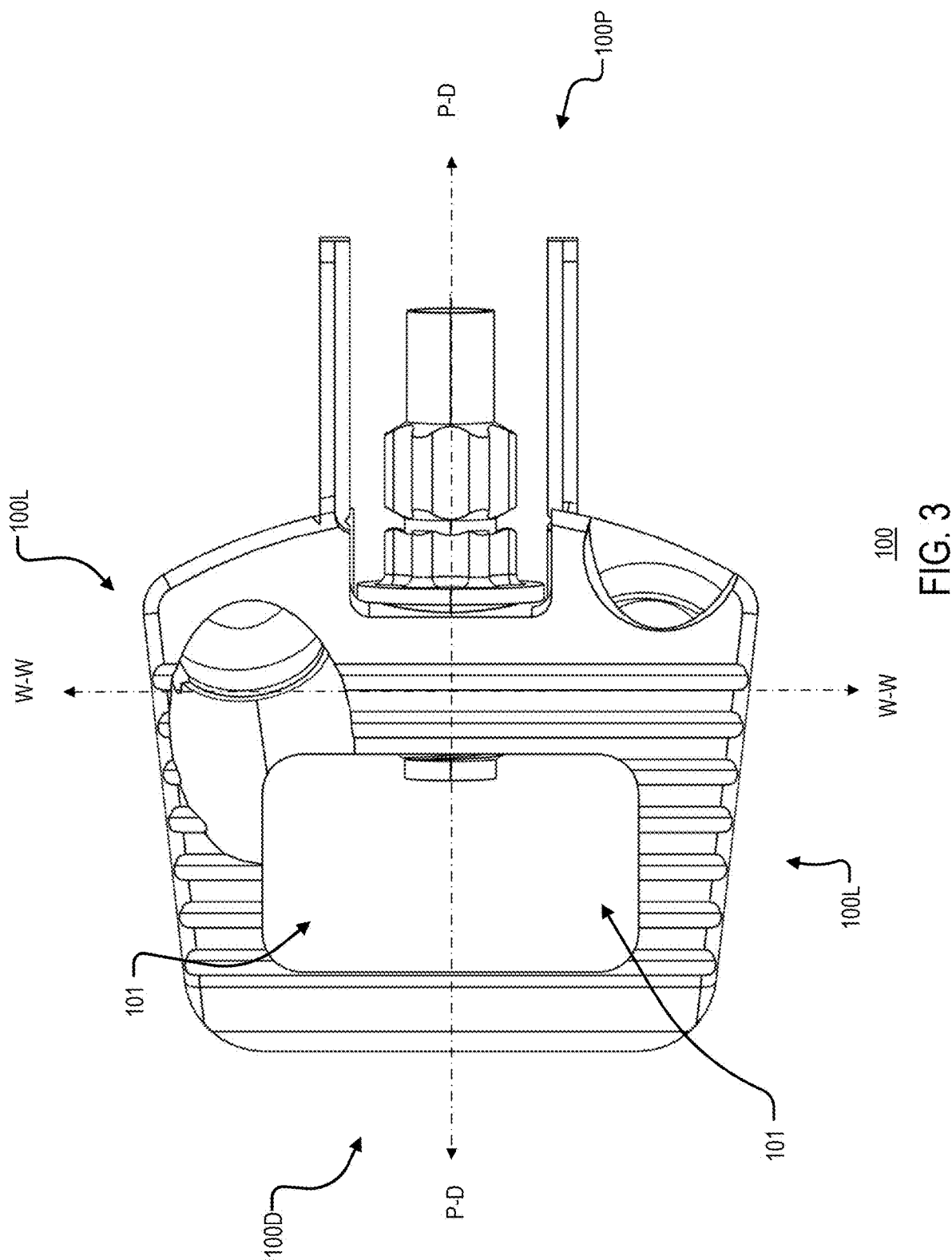
FIG. 3 is a top down view of an expandable implant.

Referring generally to FIGS. 1-5 various views of an expandable implant 100 in a collapsed position are illustrated. FIGS. 1-2 are various perspective views of an expandable implant 100. FIG. 3 is a top down view of an expandable implant 100. In the example embodiment, expandable implant 100 may include a proximal end 100P, a distal end 100D, and first and second lateral sides 100L. Additionally, a pair of bone screw apertures 11, 21 may be positioned on the proximal end 100P, for example. In various embodiments, bone screw apertures 11, 21 may comprise a corresponding bone screw retention mechanism 11a, 21a (may also be referred to as an anti-backout locking mechanism). In the example embodiment, the bone screw retention mechanisms 11a, 21a, comprise a flexible tang member having a hook portion at an end thereof that allows the flexible tang member to flex outward in a lateral direction away from the corresponding bone screw aperture 11, 21 during initial installation of the bone screw and to flex back inward towards the corresponding bone screw aperture 11, 21 to prevent a corresponding bone screw from backing out. For example, as the bone is installed in bone screw aperture 11, 21, the bone screw retention mechanism 11a, 21a, may flex outward as the underside of the head portion contacts inclined surface 11c (see FIG. 19).

In various embodiments, and as illustrated in FIGS. 1-2, mounting tangs 19, 29 may extend in a proximal direction (may also be referred to as an anterior direction depending on surgical technique and orientation), for example. In various embodiments, implant 100 may be referred to as an externally driven expandable implant because an end user or surgeon may use a surgical tool to open and close implant 100, e.g. expand implant 100. For example, an external tool may adjust the lordotic angle of implant 100 as will be explained in detail with respect to FIGS. 20-25. Once implant 100 is expanded to an appropriate lordotic angle (also referred to as angle of inclination), an end user may fix the relative angle of the superior endplate 10 relative to the inferior endplate 20 by tightening locking screw 50, for example. In some embodiments, superior endplate 10 may be referred to as a "cephalad" endplate and inferior endplate 20 may be referred to as a "caudal" endplate.

Locking screw 50 may also be used in other embodiments, such as fixation of posterior rods, fixation of pedicle screws, and other set screw constructs. Additionally, locking screw 50 may be referred to as a "breakoff screw" in some embodiments.

At least one advantage of relying on an external tool to adjust a lordotic angle of implant 100 may be the reduction of internal components within implant 100 relative to other forms of implants relying on various moving mechanisms and/or expansion mechanisms, for example. Accordingly, in various embodiments, implant 100 may have a relatively large void space in the interior thereof, which may facilitate a fusion process during an ACDF procedure. For example, implant 100 may have a relatively large internal volume 101 that is open through the superior endplate 10 and inferior endplate 20 which may be packed with bone graft material, for example.

As illustrated in FIG. 3, implant 100 may extend in a proximal-to-distal direction (may also referred to as a longitudinal direction and/or an anterior-to-posterior direction depending on surgical technique and final orientation) from the proximal end 100P (may be referred to as anterior end depending on surgical technique and final orientation) to the distal end 100D (may be referred to as posterior end depending on surgical technique and final orientation) though axis P-D through the center of the implant 100, for example. Implant 100 may extend in a widthwise direction (also referred to as lateral direction) from the first lateral side 100L to the second lateral side 100L through axis W-W through the center of the implant 100 and the center of locking screw 50, for example. The axis P-D may be perpendicular and/or substantially perpendicular to the axis W-W. For example, the proximal-to-distal direction may be perpendicular to the widthwise direction. Additionally, a width of the implant may taper from a proximal end 100P where it is widest towards a distal end 100D where it is narrowest. In various embodiments, implant 100 may extend from a superior endplate 10 to an inferior endplate 20 in a heightwise direction (may also be referred to as a cephalad-to-caudal and/or vertical direction depending on surgical technique and final orientation).

Figure 4:
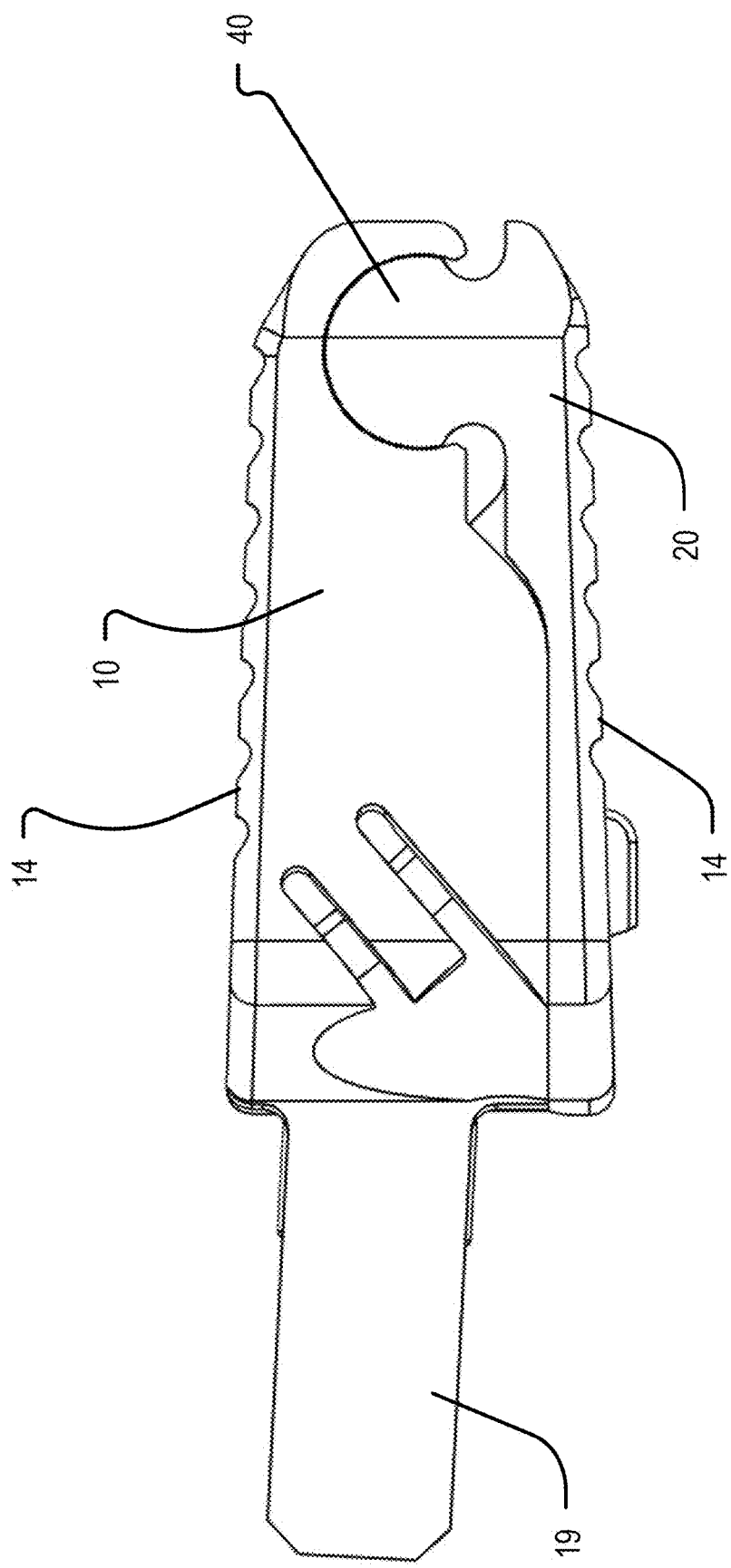
FIG. 4 is a side view of an expandable implant.

FIG. 4 is a side view of an expandable implant 100. In the example illustration, it is shown that a superior endplate 10 is connected to an inferior endplate 20 such that the superior endplate may pivot about a hinge member 40. In the example embodiment, hinge member 40 comprises an arcuate rail portion of inferior endplate 20 that extends in the widthwise direction, for example. In other embodiments, the hinge member 40 may be reversed relative to the superior and inferior endplates than as illustrated in FIG. 4. In the example embodiment, hinge member 40 may be nested into a corresponding arcuate cavity of the superior endplate 10 such that superior endplate 10 may expand and/or otherwise rotate about hinge member 40. Additionally, in various embodiments the superior endplate 10 and/or inferior endplate 20 may include various engagement elements 14 for engaging with an adjacent boney structure such as a vertebrae, for example. In the example embodiment, the engagement elements comprise a series of alternating rails and valleys therebetween that extend in the widthwise direction. In some embodiments, the valleys may be angled about 20-40 degrees and in at least one embodiment the valleys may be angled at about 30 degrees relative to the corresponding rail (see FIGS. 42A and 42B). At least one advantage of this orientation may be a relatively greater resistance and/or suppression of expulsion of the implant 100 in both the lateral direction and in the proximal-to-distal direction. However, claws, hooks, dimples, spikes, etc. are also contemplated as example engagement elements 14. In some embodiments, an acid etching process may be utilized to form a roughened or textured surface to facilitate securing the implant between boney portions and/or suppressing expulsion of implant 100.

Figure 5:
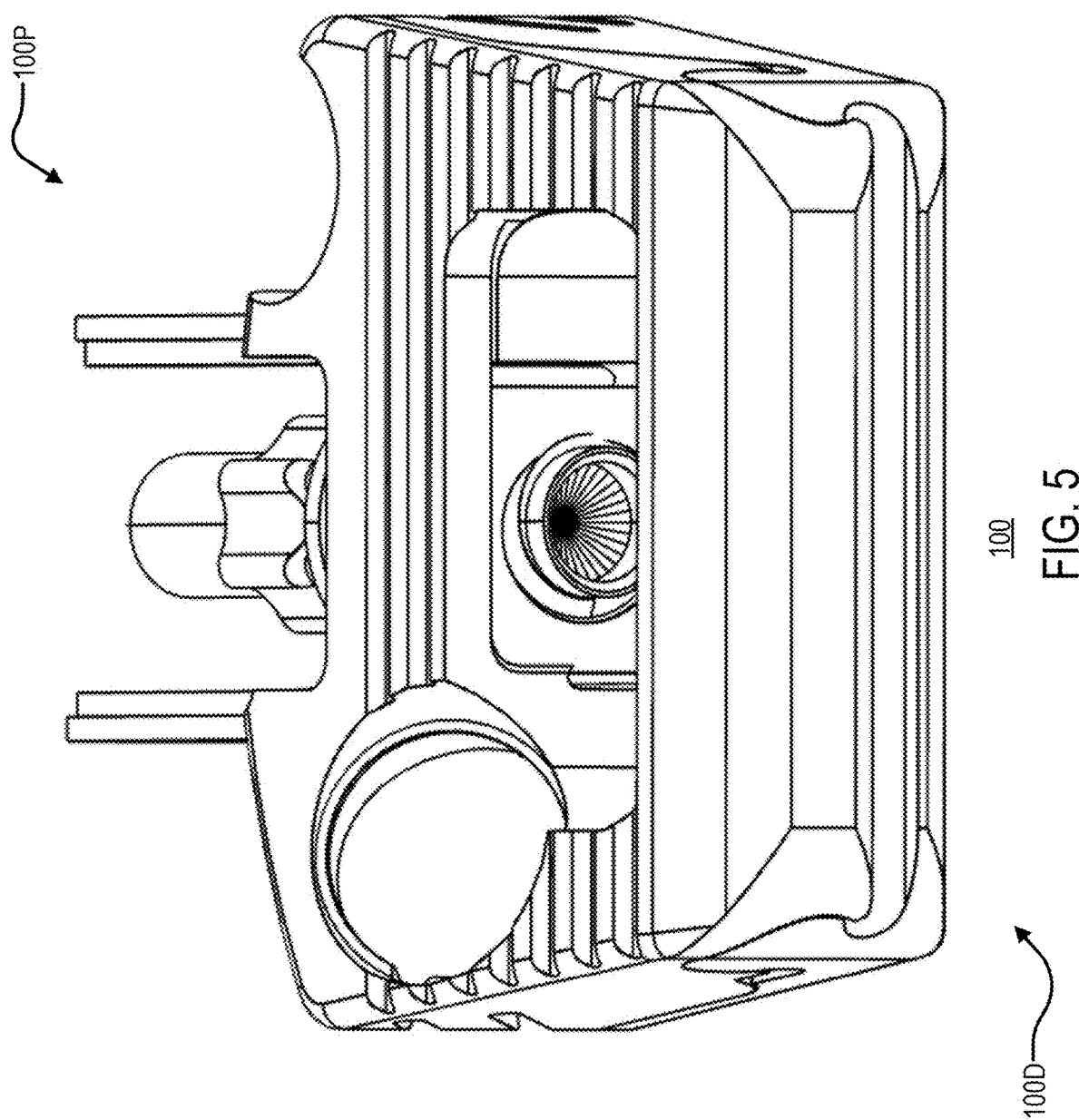
FIG. 5 is a rear perspective view of an expandable implant.
Figure 6:
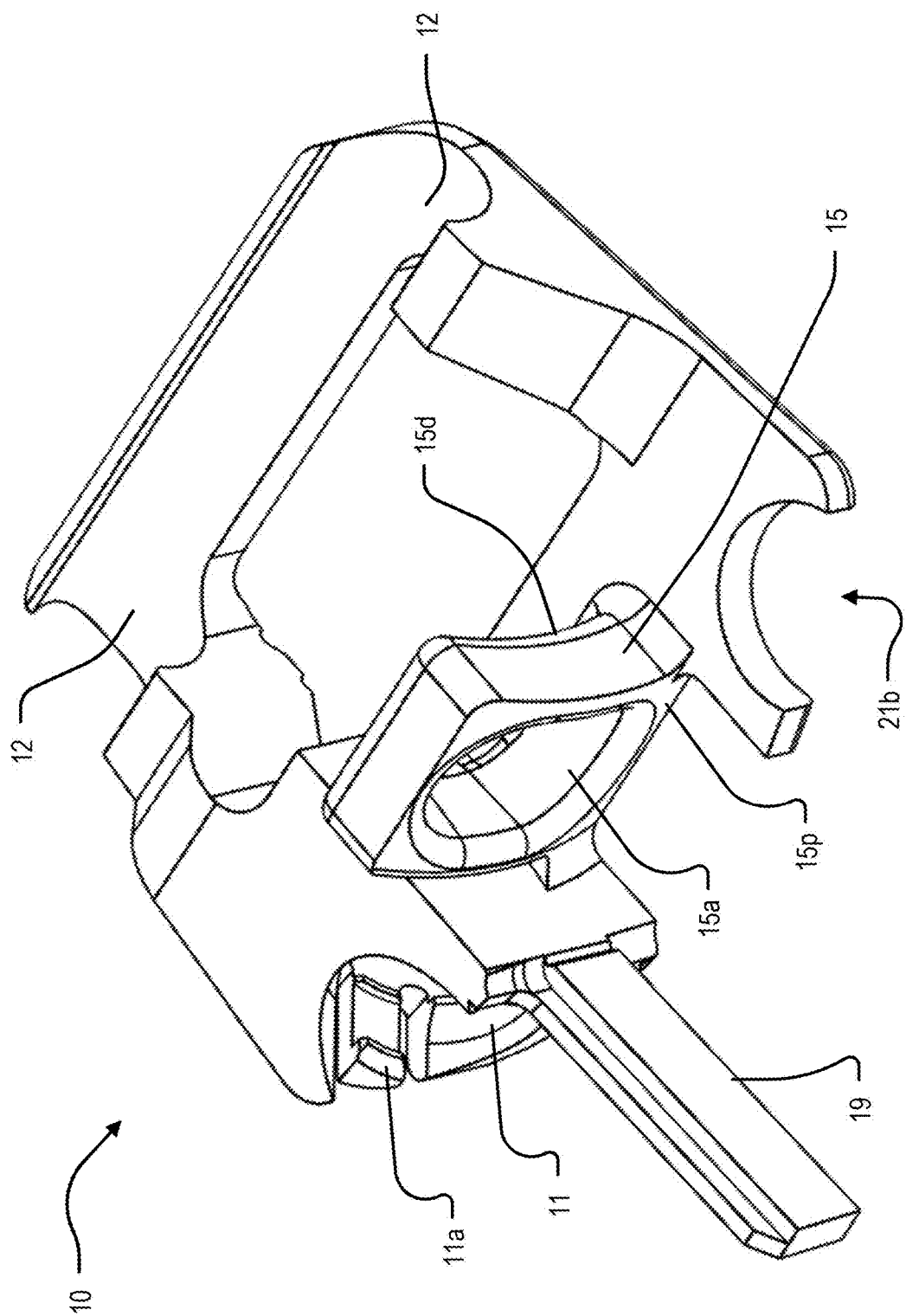
FIG. 6 is a perspective view of the interior of a superior endplate of an expandable implant.
Figure 7:
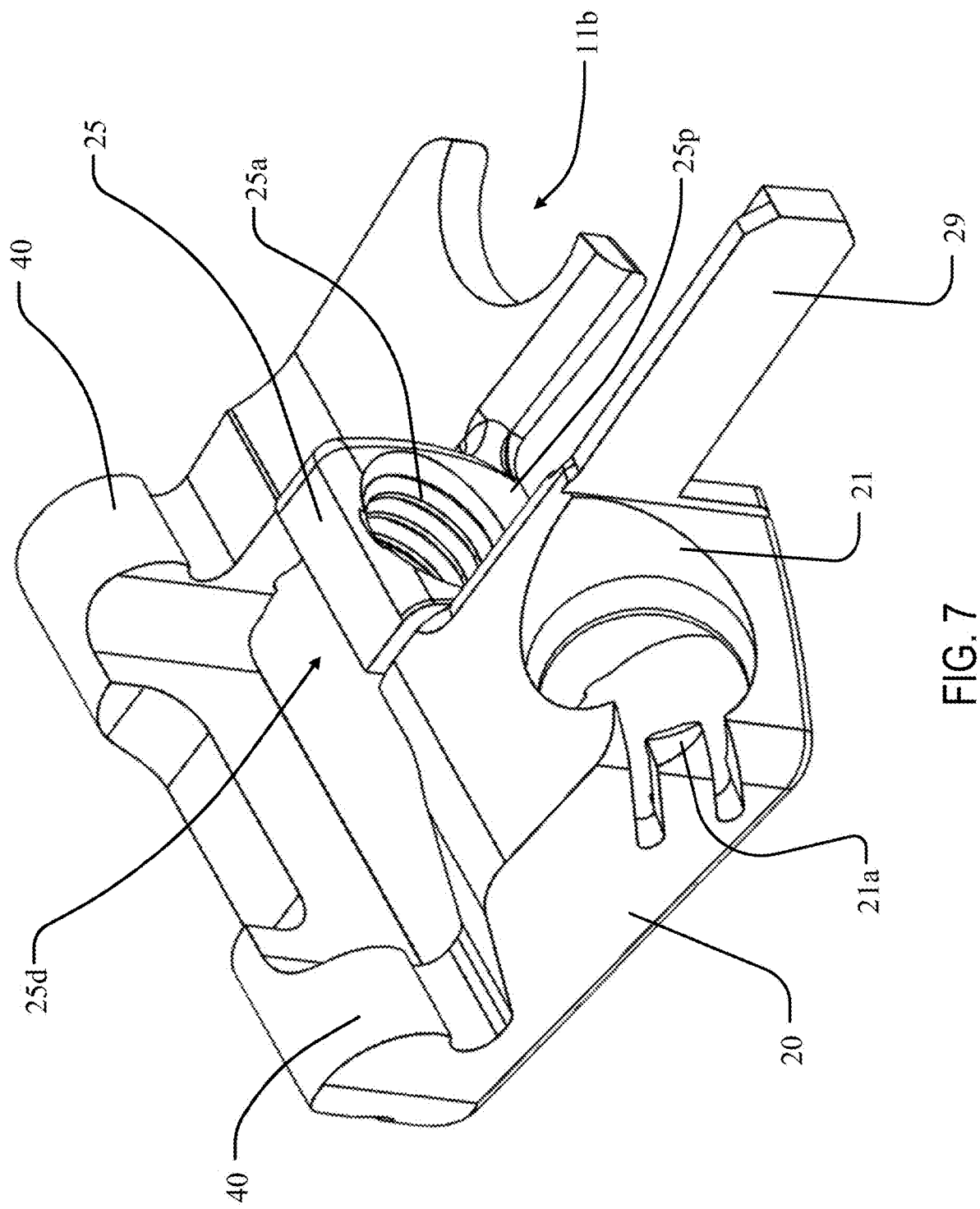
FIG. 7 is a perspective view of the interior of an inferior endplate of an expandable implant.

FIG. 5 is a rear perspective view of an expandable implant 100. In the example illustration it is shown that the distal end 100D is narrower than the proximal end 100P. FIG. 6 is a perspective view of the interior of a superior endplate 10. In the example illustration, it is shown that the distal end of superior endplate 10 includes an arcuate channel 12 of which the hinge member 40 may be disposed inside of. The proximal end of superior endplate 10 may include a bone screw aperture cutout 21b to allow a relief area for a corresponding bone screw to be insert through bone screw aperture 21 of inferior endplate 20, for example. Superior endplate 10 may also include a core 15 comprising an aperture 15a that extends from a proximal surface 15p thereof to a distal surface 15d thereof, for example. In various embodiments, aperture 15a may be referred to as a "slot'" or "screw slot". In some embodiments, core 15 may be referred to as a support frame and take a generally rectangular shape. In various embodiments, the distal surface 15d may be curved and generally face the distal end 100D of implant 100. FIG. 7 is a perspective view of the interior of an inferior endplate 20. In the example illustration, it is shown that the distal end of inferior endplate 20 includes a hinge member 40 in the form of an arcuate rail that may be disposed inside of the arcuate channel 12 of the superior endplate 10, for example. The proximal end of inferior endplate 20 may include a bone screw aperture cutout 11b to allow a relief area for a corresponding bone screw to be insert through bone screw aperture 11 of superior endplate 10, for example. Inferior endplate 20 may also include a core 25 comprising a threaded aperture 25a that extends from a proximal surface 25p thereof to a distal surface 25d thereof, for example. In some embodiments, core 25 may be referred to as a support frame and take a generally rectangular shape. In various embodiments, the superior endplate 10 and inferior endplate 20 may each be formed by a unitary single piece, respectively.

Figure 8:
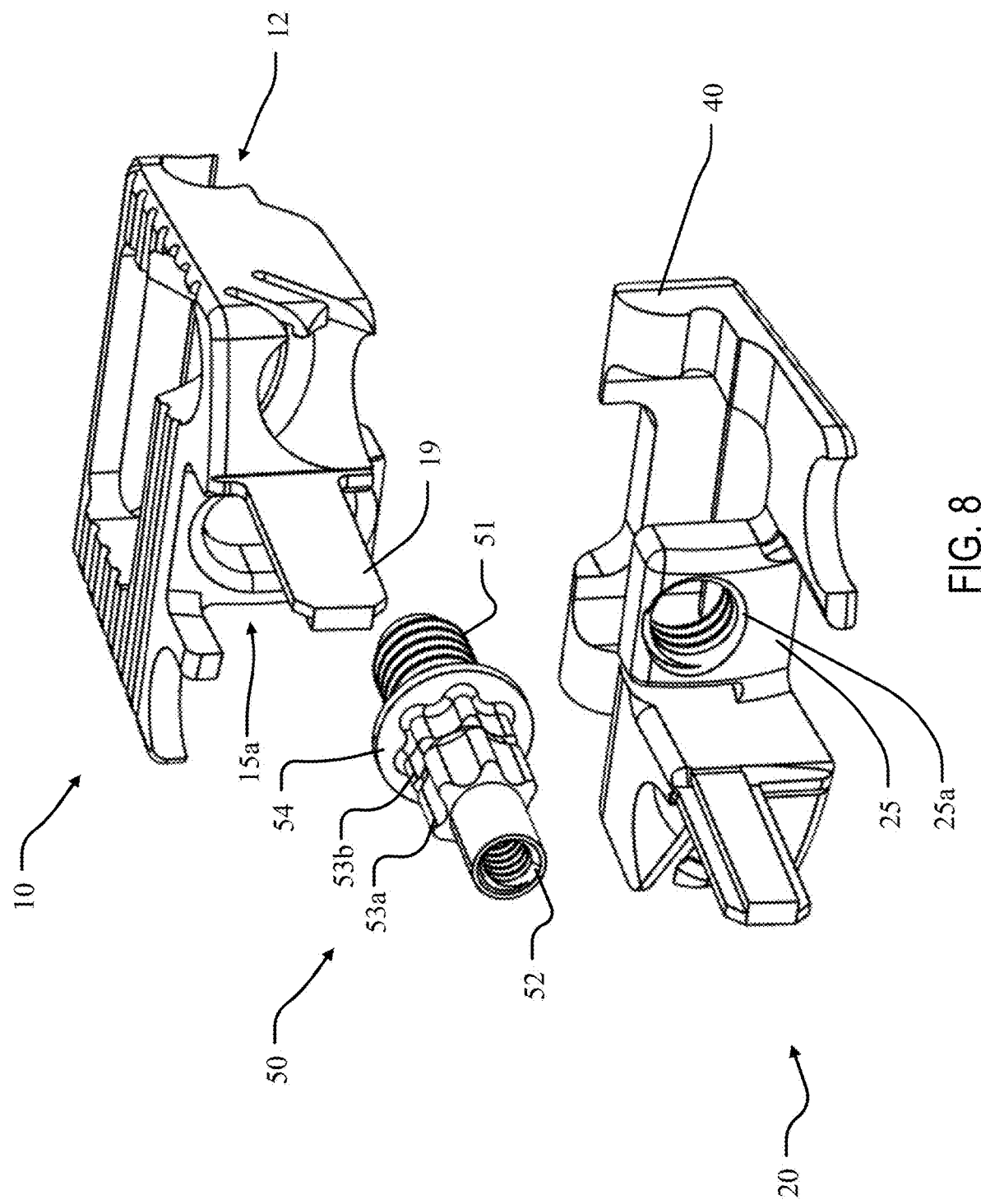
FIG. 8 is a perspective exploded parts view of an expandable implant.
Figure 9:
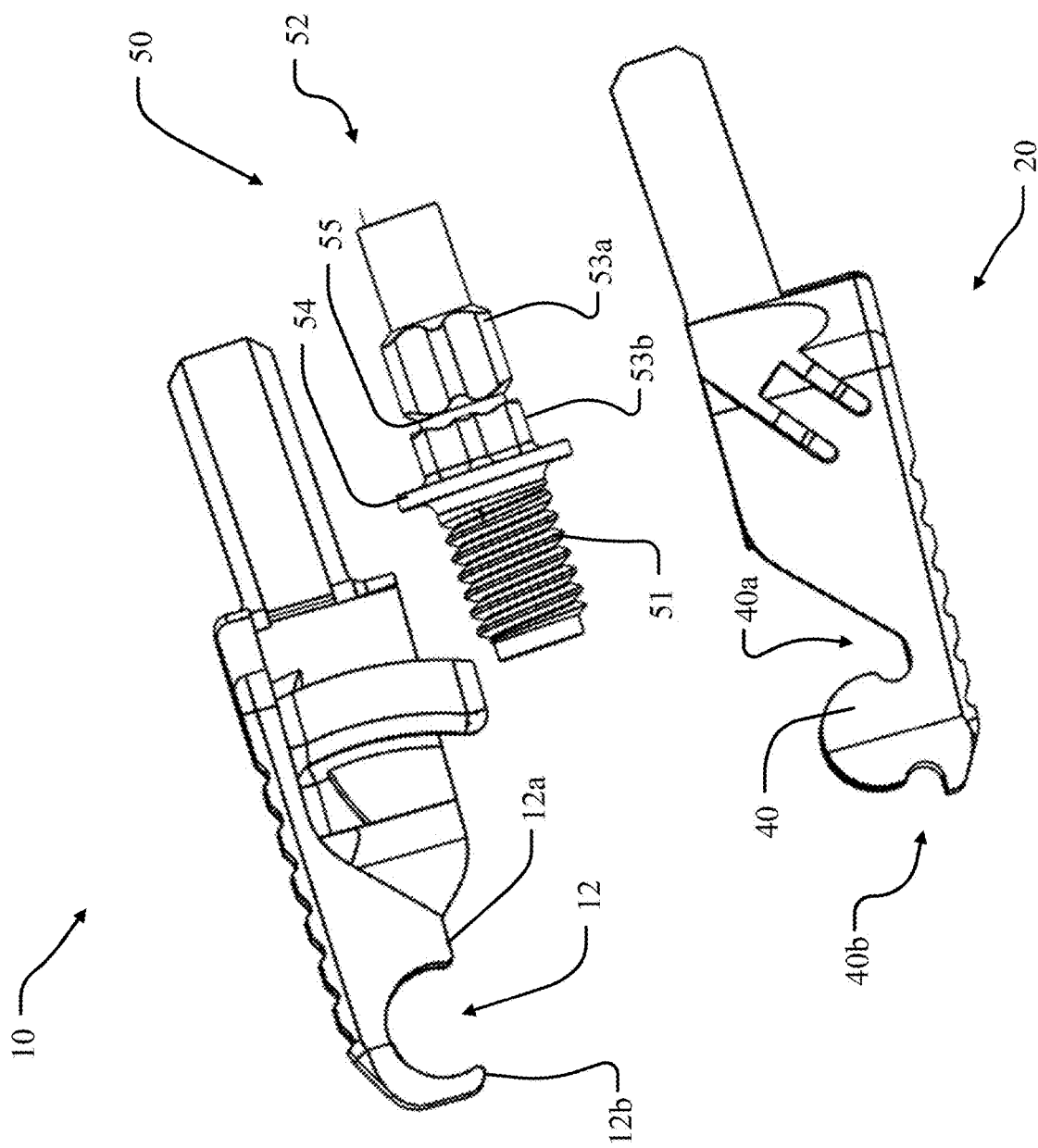
FIG. 9 an exploded parts view of an expandable implant from a side view perspective.

FIG. 8 is a perspective exploded parts view and FIG. 9 is an exploded parts view from a side view perspective of an expandable implant 100. In the example embodiment, a locking screw 50 is illustrated. Locking screw 50 may include an external thread pattern 51 on an outside circumferential surface thereof, for example. The external thread pattern 51 of locking screw 50 may have a size and shape generally corresponding to the threaded aperture 25a of core 25 of inferior endplate 20, for example. In various embodiments, an engagement surface 54 may be disposed adjacent and proximal of external thread pattern 51. In the example embodiment, engagement surface 54 is shaped like a washer and is directly connected to locking screw 50. However, in other embodiments, engagement surface 54 may be a washer or separated element, for example. In some embodiments, engagement surface 54 may be conically shaped and/or spherically shaped. Engagement surface 54 may include a relatively planar and/or flat distal surface and/or proximal surface (anterior/ventral surface). In various embodiments, a proximal end of set screw 50 may include an aperture having an internal threaded surface 52. For example, a cylindrical shaped proximal end may include an aperture having a thread pattern disposed on an internal circumferential surface of the cylindrical shaped proximal end. In the example embodiment, a first drive feature 53a and a second drive feature 53b may be disposed adjacent to and distally with respect to a proximal most end of set screw 50. Additionally, first and second drive features 53a, 53b may be disposed proximally with respect to engagement surface 54. In the example embodiment, drive features 53a, 53b take a hexalobular shape, although various other shapes such as hexagonal, polygonal, Torx, etc. are also contemplated. In some embodiments, a surgical drive tool having a corresponding socket may be coupled to drive features 53a, 53b to cause rotation of locking screw 50. Similarly, in some alternative embodiments, a drive tool with a protruding threaded member having a thread pattern with a corresponding size and shape to internal threaded surface 52 may also cause rotation of set screw 50.

As seen best in FIG. 9, set screw 50 may also include a breakoff location 55, for example. In the example embodiment, breakoff location 55 is disposed directly between drive features 53a, 53b and is designed to shear off when a sufficient rotational force (torque) is applied to a proximal end of set screw 50 while a distal end of set screw 50 is stationary, e.g., when set screw 50 is secured in a locked position and a continued rotational force (torque) is applied to the proximal end of set screw 50 the drive feature 53a and cylindrical end having the internal threaded surface 52 may breakoff. In various embodiments, the internal threaded surface 52 may also be utilized to ensure that the broken off portion is removed from the patient and remains connected to a surgical tool/breakoff tool. As also seen best in FIG. 9, the inferior endplate 20 may include a first relief 40a and a second relief 40b on opposite sides of hinge member 40. The first relief 40a may have a size and shape corresponding to a size and shape of a first portion 12a of superior endplate 10 and the second relief 40b may have a size and shape corresponding to a size and shape of a second portion 12b of superior endplate 10, for example. In various embodiments, portions 12a, 12b may comprise a hook shape, outdent, and/or protrusion, for example. In the example embodiment, portions 12a, 12b may be disposed on opposite sides of channel 12 and cup hinge member 40 such that the superior endplate 10 and inferior endplate 20 may rotate relative to one another without becoming uncoupled.

Figure 10:
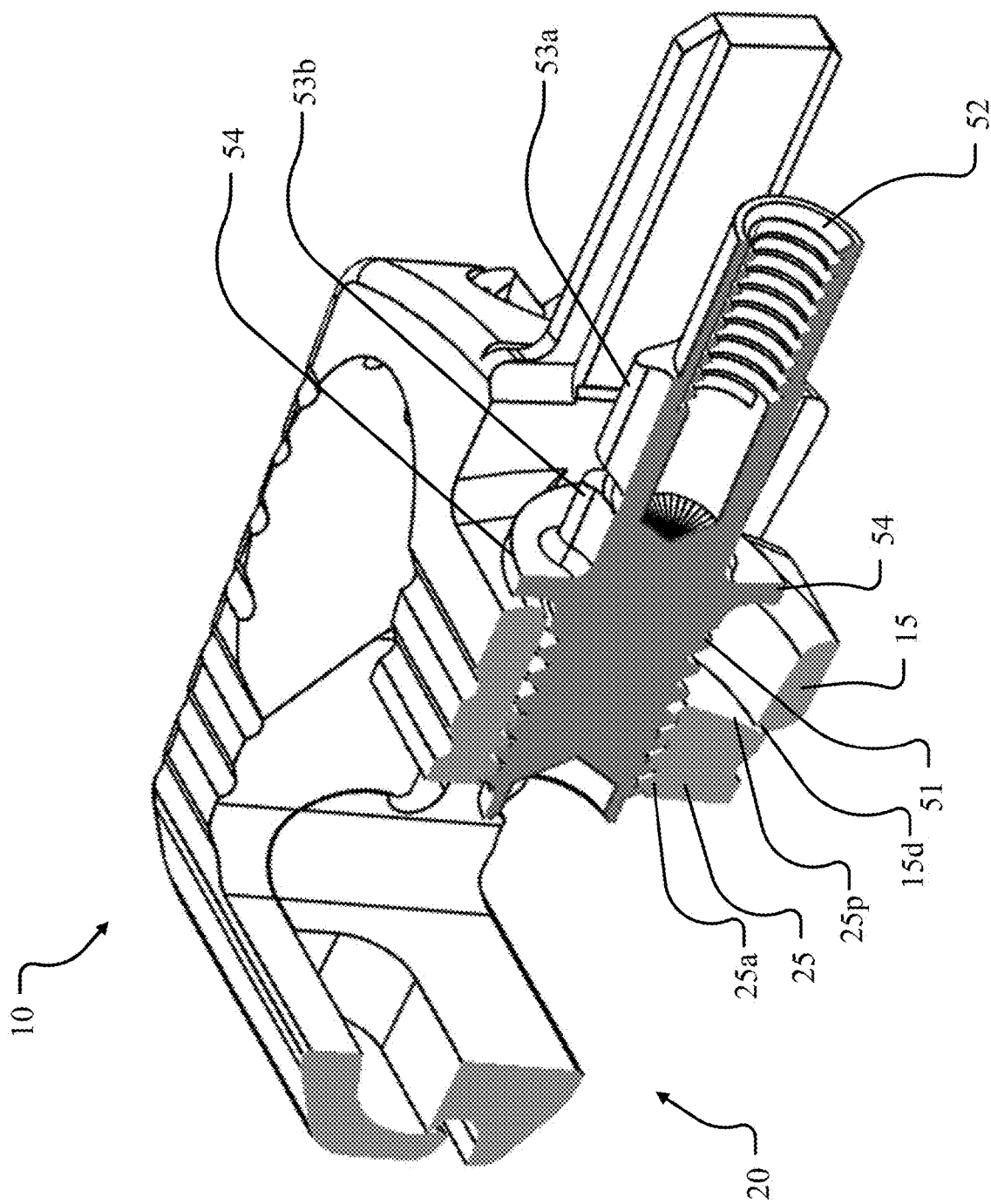
FIG. 10 is a perspective cross section view of an expandable implant.
Figure 11:
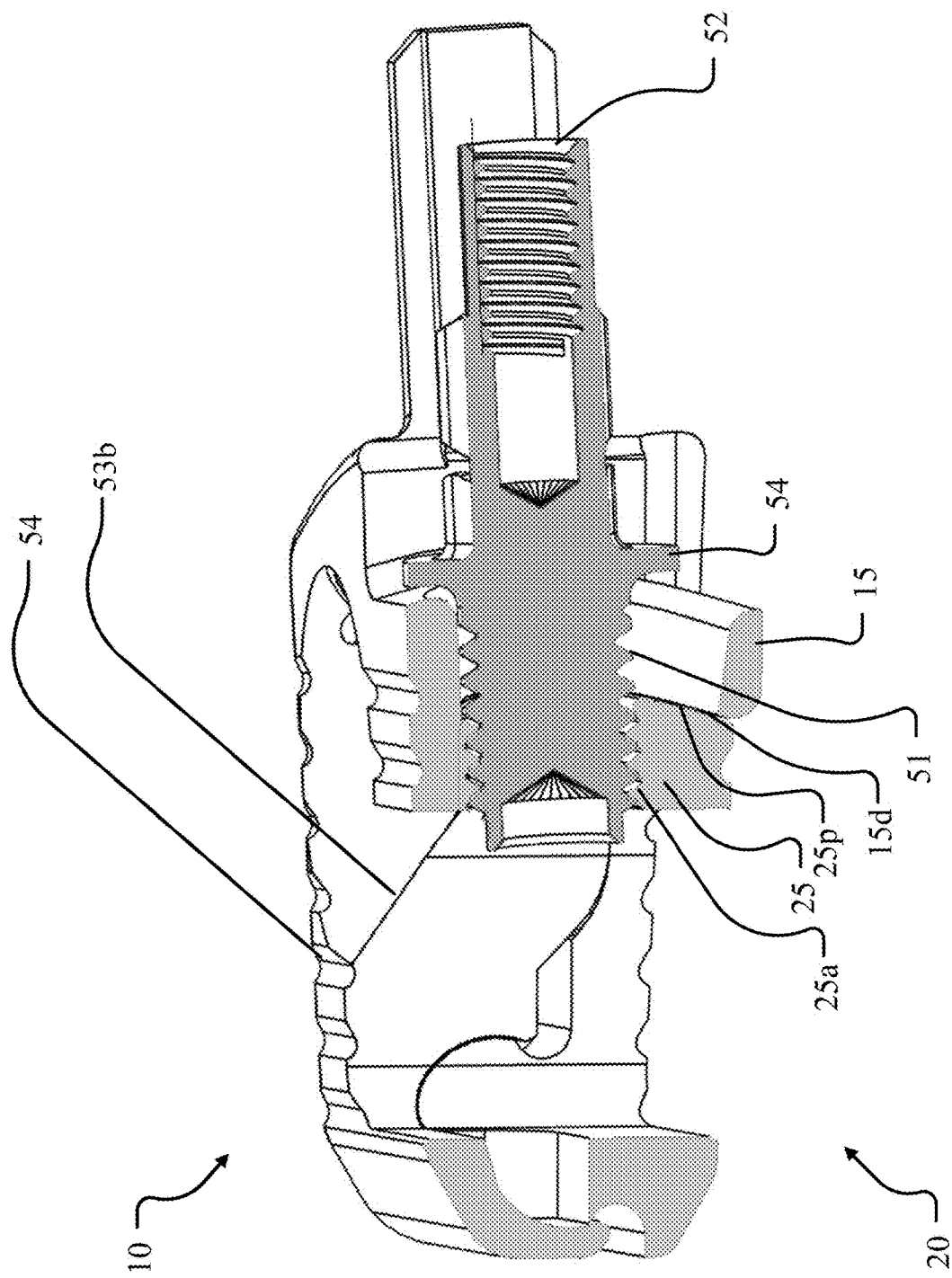
FIG. 11 is a cross section view of an expandable implant.

FIG. 10 is a perspective cross section view and FIG. 11 is a cross section view of expandable implant 100. In the example embodiment, the superior endplate 10 and inferior endplate 20 are coupled together by hinge member 40, and core 25 may be positioned behind of core 15, e.g., core 25 may be positioned distally with respect to core 15. Additionally, the outside external thread pattern 51 of locking screw 50 may engage with the threaded aperture 25a of the core 25 and extend through aperture 15a of core 15. In this way, when locking screw 50 is rotated, the distal surface 15d of core 15 may engage with the proximal surface 25p of core 25. For example, by tightening locking screw 50 the engagement surface 54 of locking screw 50 pushes against the proximal surface 15p of core 15 thereby bringing the superior endplate 10 and inferior endplate 20 into frictional engagement.

Figure 12:
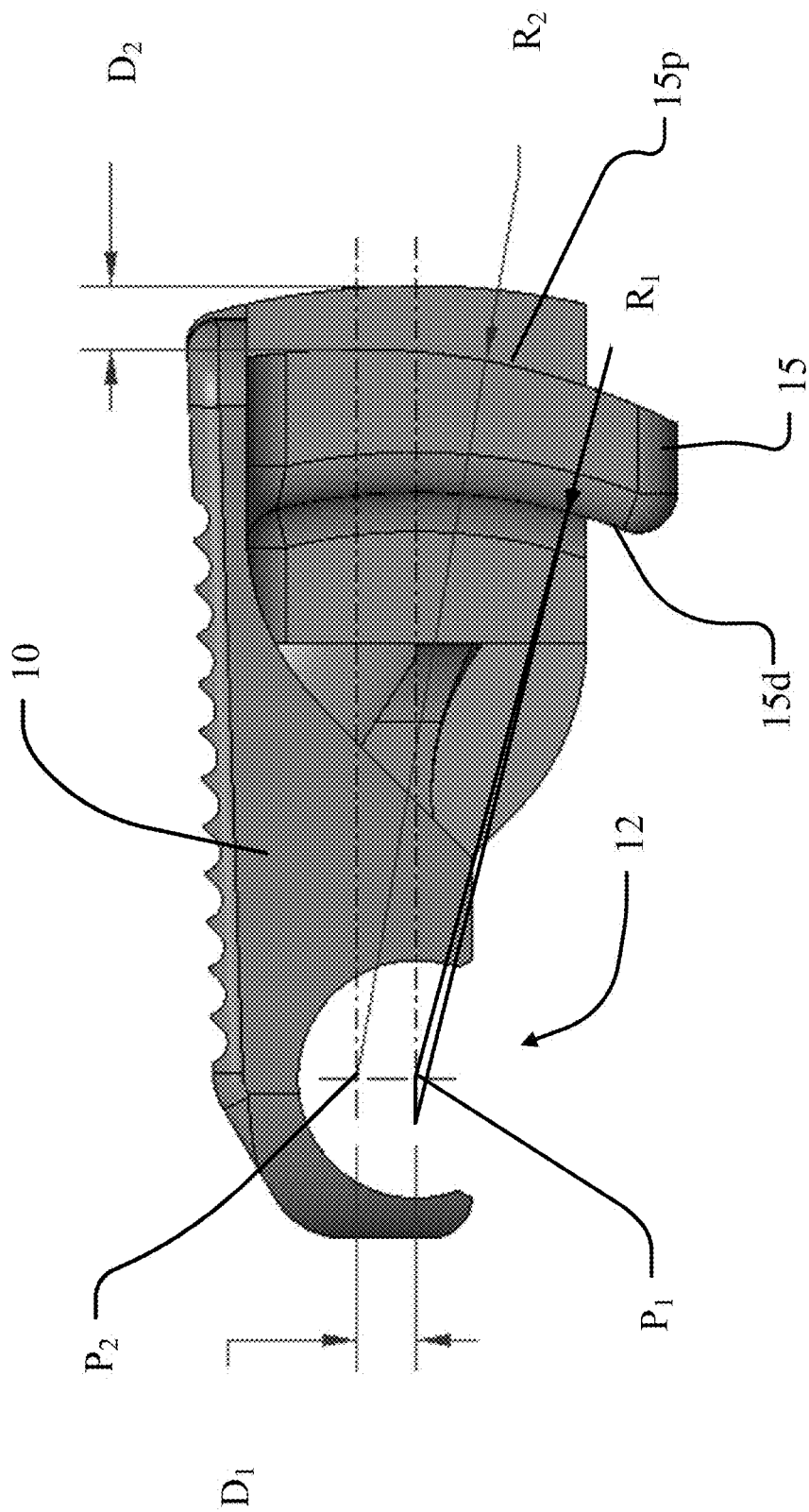
FIG. 12 is a side view of a superior endplate for use with at least some expandable implant embodiments.

FIG. 12 is a side view of a superior endplate 10 for use with at least some expandable implant 100 embodiments. In the example embodiment, superior endplate 10 may include an arcuate channel 12 of which the hinge member 40 may be disposed inside of. In various embodiments, arcuate channel 12 may be defined by a first circle having a center point at $P_1$ and/or a segment of the circle having the center point at $P_1$. The center point $P_1$ may define an axis of rotation that superior endplate 10 may rotate and/or pivot with respect to inferior endplate 20. For example, superior endplate 10 may be hingedly coupled to hinge member 40 as explained above and rotatable about an axis of rotation defined by center point $P_1$, for example. Additionally, in various embodiments a distal surface 15d of core 15 may be a curved surface defined (in part or in total) by a second circle having a center point at $P_1$ and a radius $R_1$. The proximal surface 15p of core 15 may also be a curved surface defined (in part or in total) by a segment of a circle having a radius $R_2$ and a center point $P_2$. In the example embodiment, $P_2$ is located a distance $D_1$ above point $P_1$ and radius $R_2$ is greater than radius $R_1$. Additionally, the proximal surface 15p of core 15 is offset a distance $D_2$ from the proximal most face of the superior endplate 10. In the example embodiment, center point $P_2$ is vertically above center point $P_1$ however, in other embodiments, center point $P_2$ may be offset by a greater amount or even a lesser amount than illustrated. In some examples, $P_2$ may not be aligned vertically above $P_1$. In various embodiments, $R_1$ may be about 7-9 mm+/−about 1 mm and $R_2$ may be about 8-10 mm+/−about 1 mm although these numbers may be modified in some embodiments having a larger or smaller footprint. In various embodiments $D_1$ is about 0.25 mm to about 1.0 mm and $D_2$ is about 0.25 mm to about 1.25 mm. In at least one embodiment, $D_1$ is about 0.75 mm and $D_2$ is about 0.8 mm and $R_2$ is about 9.2 mm.

The above explained geometrical relationship between the offset center points $P_1$ and $P_2$ and $R_1$ and $R_2$ may have several advantages in terms of operability and functionality. At least one advantage is that the superior endplate 10 may have a natural tendency to apply a force against the engagement surface 54 of locking screw 50 such that locking screw 50 may function similar to a wedge preventing implant 100 from fully collapsing. Another advantage is that a biasing force may be applied that naturally urges the superior endplate 10 and inferior endplate 20 into an expanded position which may assist with expanding the implant 100 when positioned between a superior vertebrae and an inferior vertebrae, for example. For example still, an end user such as a surgeon may expand implant 100 and the offset arrangement explained above may facilitate the function of keeping implant 100 lordosed at the chosen angle.

Figure 13B:
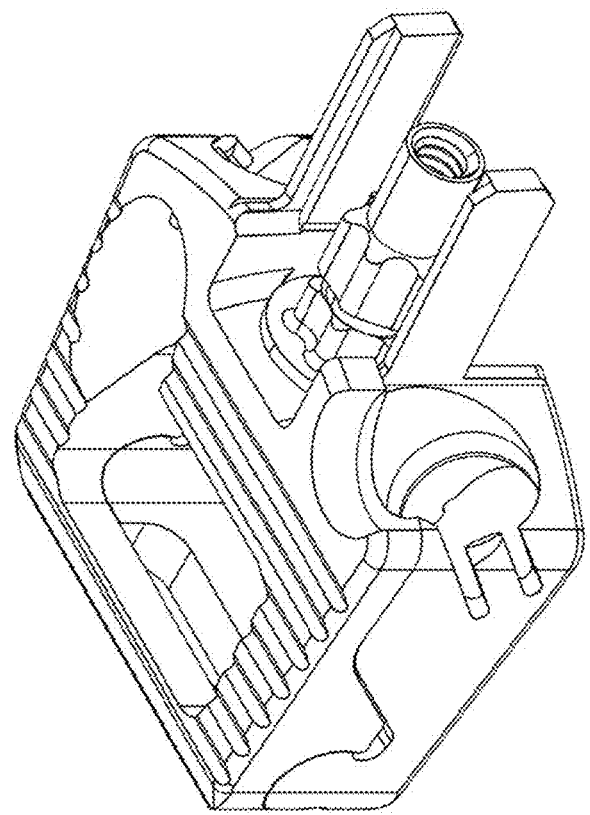
FIG. 13B is a perspective view of a second expandable implant.
Figure 13A:
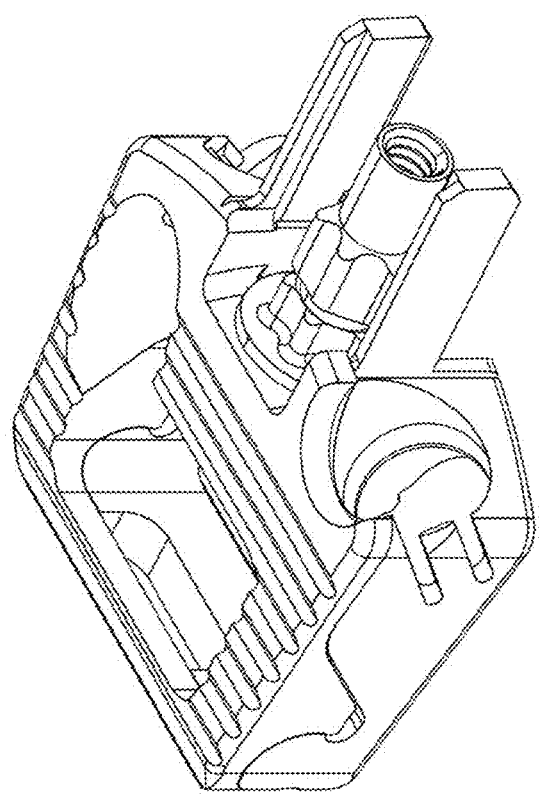
FIG. 13A is a perspective view of a first expandable implant.
Figure 14B:
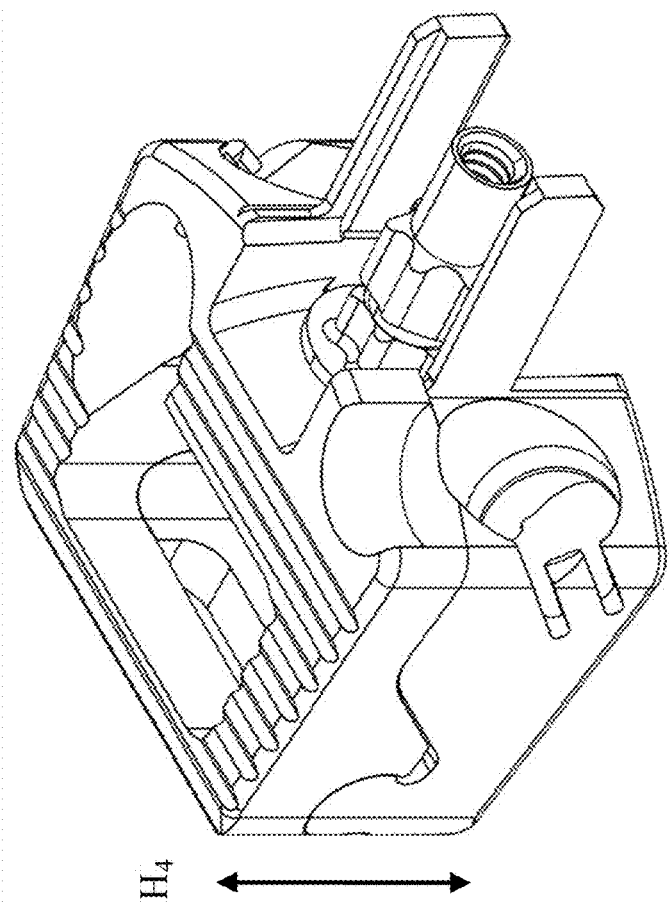
FIG. 14B is a perspective view of a fourth expandable implant.
Figure 14A:
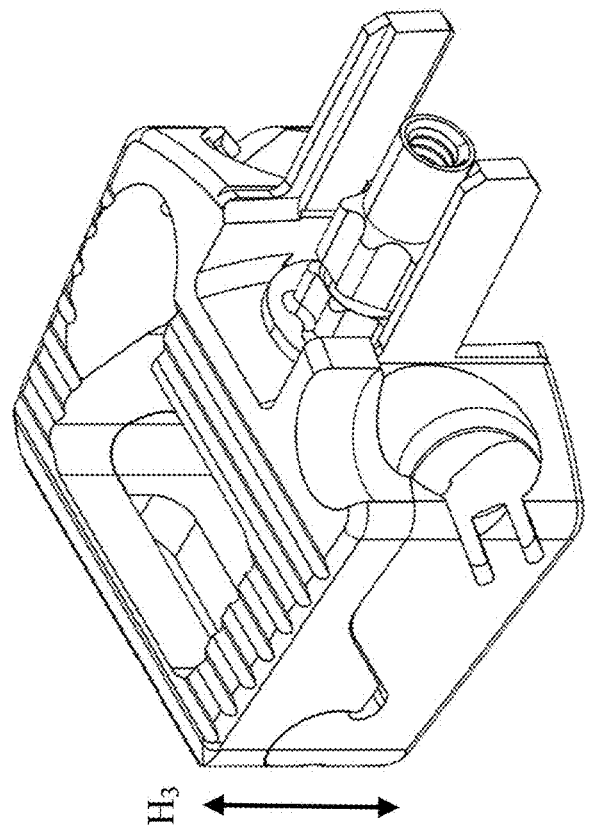
FIG. 14A is a perspective view of a third expandable implant.
Figure 15:
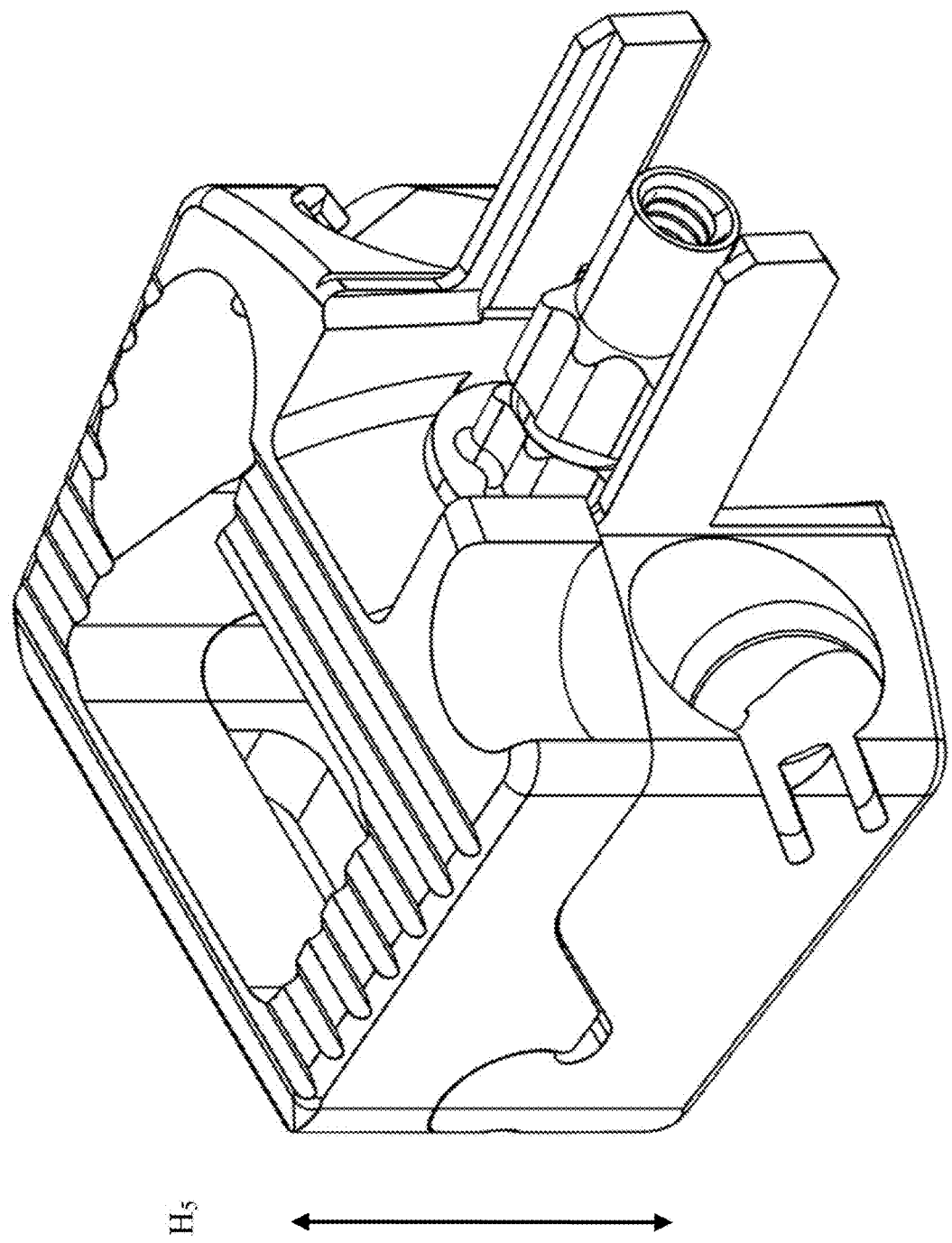
FIG. 15 is a perspective view of a fifth expandable implant.

FIG. 13A is a perspective view of a first expandable implant, FIG. 13B is a perspective view of a second expandable implant, FIG. 14A is a perspective view of a third expandable implant, FIG. 14B is a perspective view of a fourth expandable implant, and FIG. 15 is a perspective view of a fifth expandable implant. In the series of illustrations it is shown that various embodiments in accordance with the principles of this disclosure may be variously sized depending on the particular location in a human body and the particular patient specific human anatomy. For example, FIG. 13A illustrates a first expandable implant 100 having a first height $H_1$ or thickness between the superior endplate 10 and inferior endplate 20, FIG. 13B illustrates a second expandable implant 100 having a second height $H_2$ or thickness, FIG. 14A illustrates a third expandable implant 100 having a third height $H_3$ or thickness, FIG. 14B illustrates a fourth expandable implant 100 having a fourth height $H_4$ or thickness, and FIG. 15 illustrates a fifth expandable implant 100 having a fifth height $H_5$ or thickness. In at least some embodiments, $H_1$ may be about 5 mm, $H_2$ may be about 6 mm, $H_3$ may be about 7 mm, $H_4$ may be about 8 mm, $H_5$ may about 9 mm, for example. In various embodiments, an angle of inclination between the superior endplate 10 and inferior endplate 20 may be about 4 degrees to about 15 degrees in an expanded configuration, e.g., an angled and/or inclined configuration.

Figure 16:
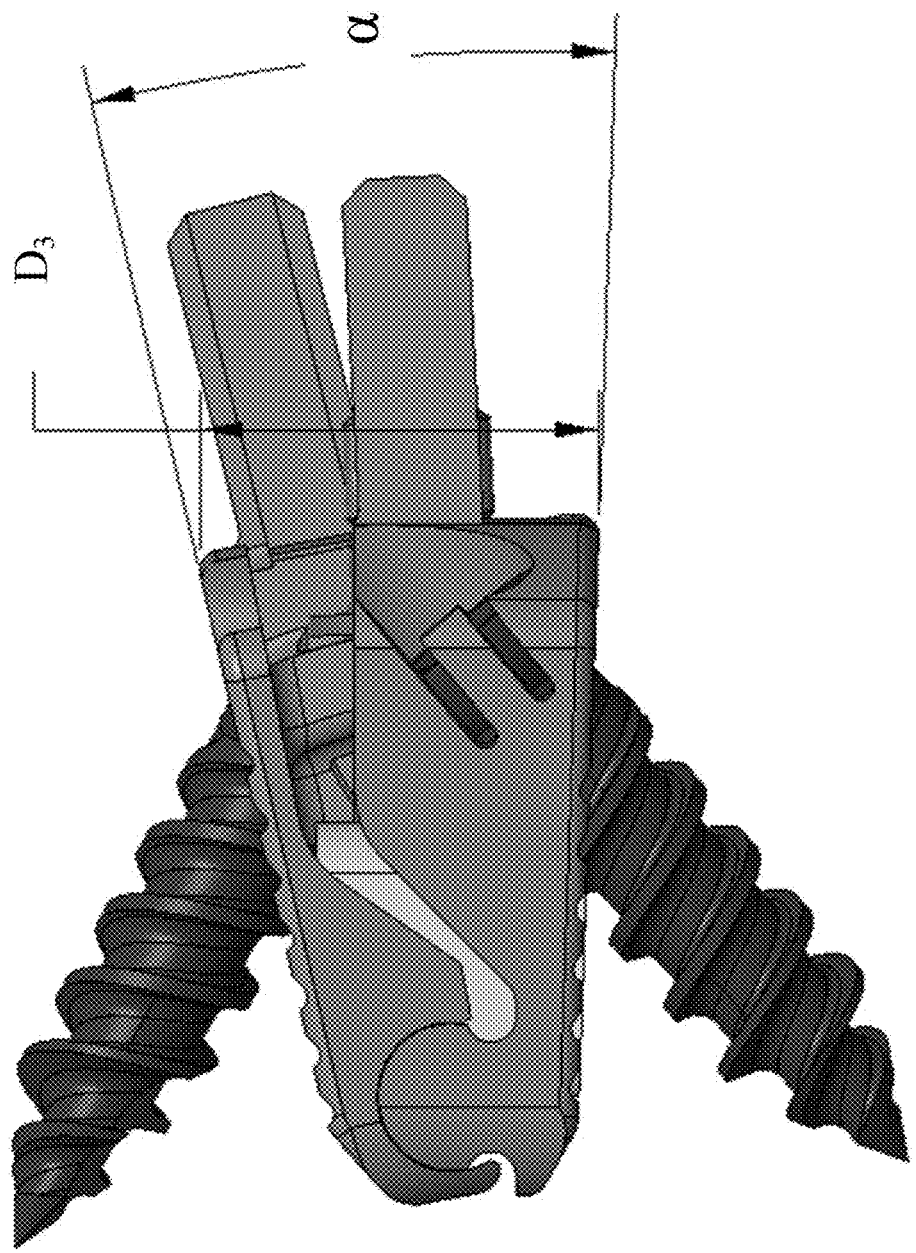
FIG. 16 is a side view of an expandable implant in the expanded configuration.

FIG. 16 is a side view of an expandable implant 100 in the expanded configuration. In an expanded position, a distance $D_3$ between the superior endplate 10 and inferior endplate 20 at the proximal end 100P may be relatively greater than in the closed configuration, for example. Additionally, an angle of inclination a may be relatively greater in an expanded position than in the closed configuration, for example. In this embodiment, implant 100 may have a height $H_1$ corresponding to FIG. 13A and be about 5 mm in a closed configuration. In the illustrated expanded configuration of FIG. 16, $D_3$ may be about 8 mm to 9 mm and a may be about 10 degrees to about 20 degrees. In at least one embodiment, $D_3$ may be 8 mm in a fully expanded position and a may be about 15 degrees, for example.

Figure 17:
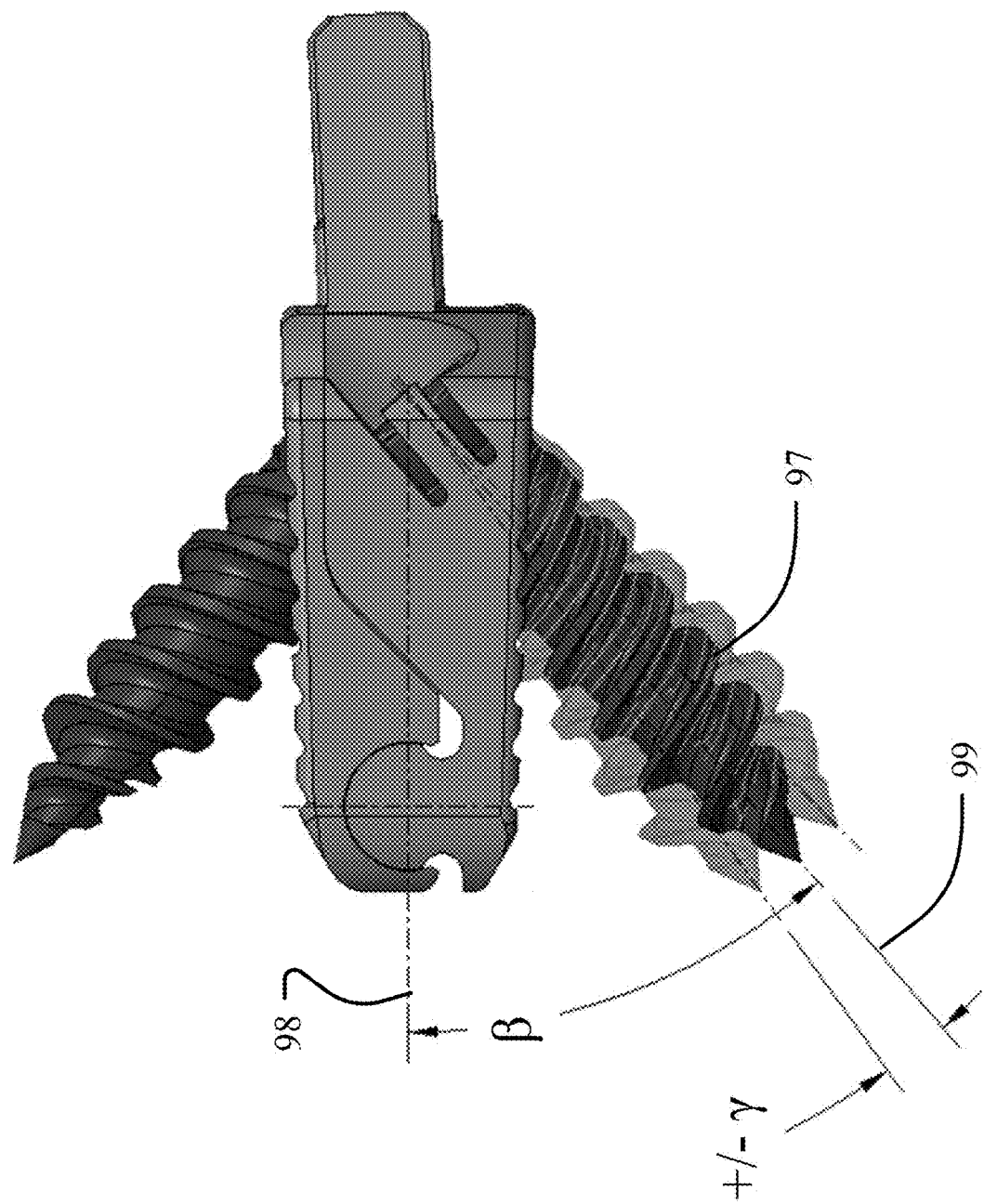
FIG. 17 is a side view of an expandable implant showing a bone screw trajectory.

FIG. 17 is a side view of an expandable implant 100 showing a bone screw trajectory 99. In the example embodiment, it is shown that a centered bone screw trajectory 99 of bone screw 97 is at an angle β with respect to a plane 98 that crosses through a center of the implant from a first lateral side to a second lateral side, for example. Additionally, the bone screw trajectory 99 may be varied+/− by a degree γ, for example. In various embodiments, β may be about 30 degrees to about 50 degrees and γ may be about 2 degrees to about 10 degrees. In the example embodiment, 13 may be about 40 degrees and γ may be about 5 degrees.

Figure 18:
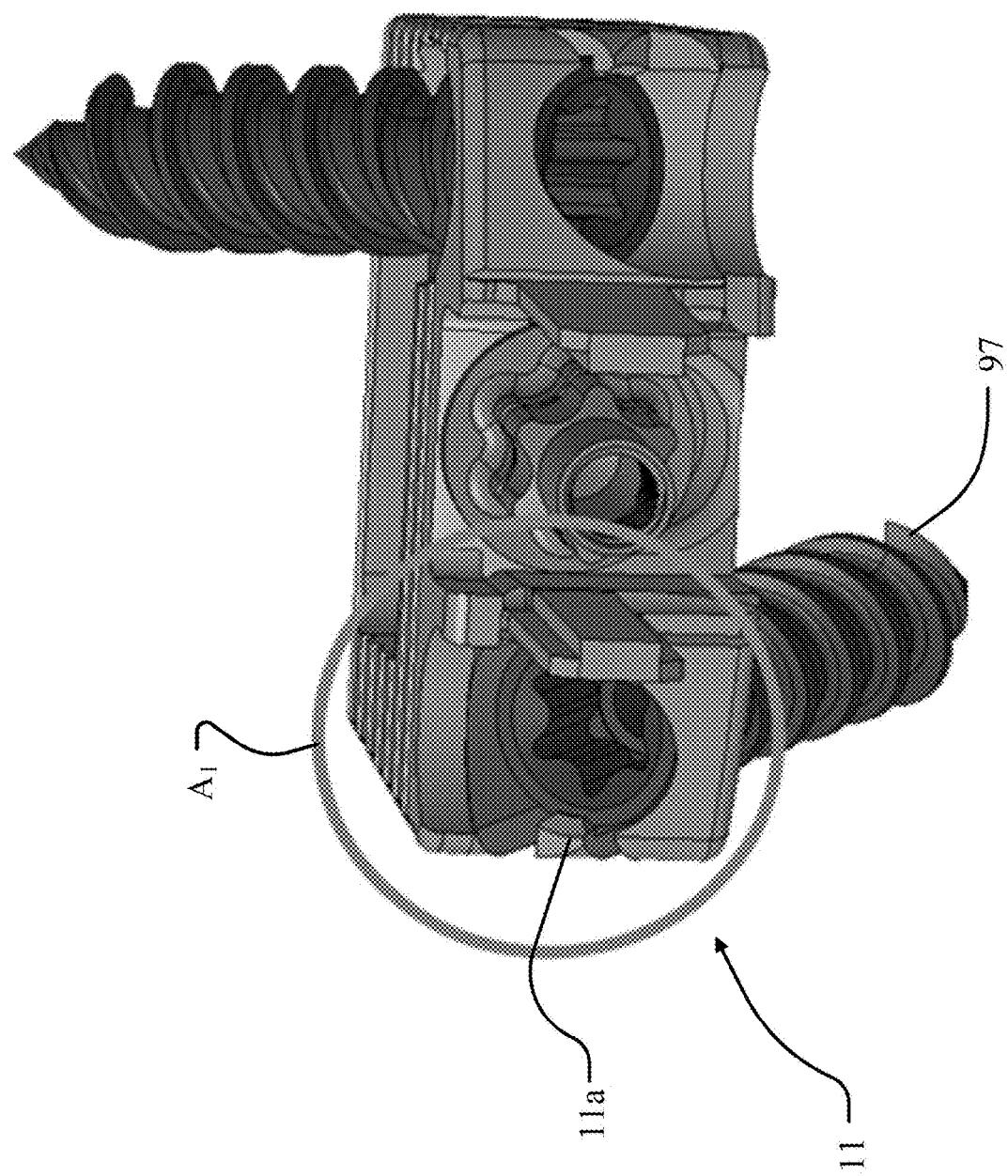
FIG. 18 is a front view of an expandable implant.
Figure 19:
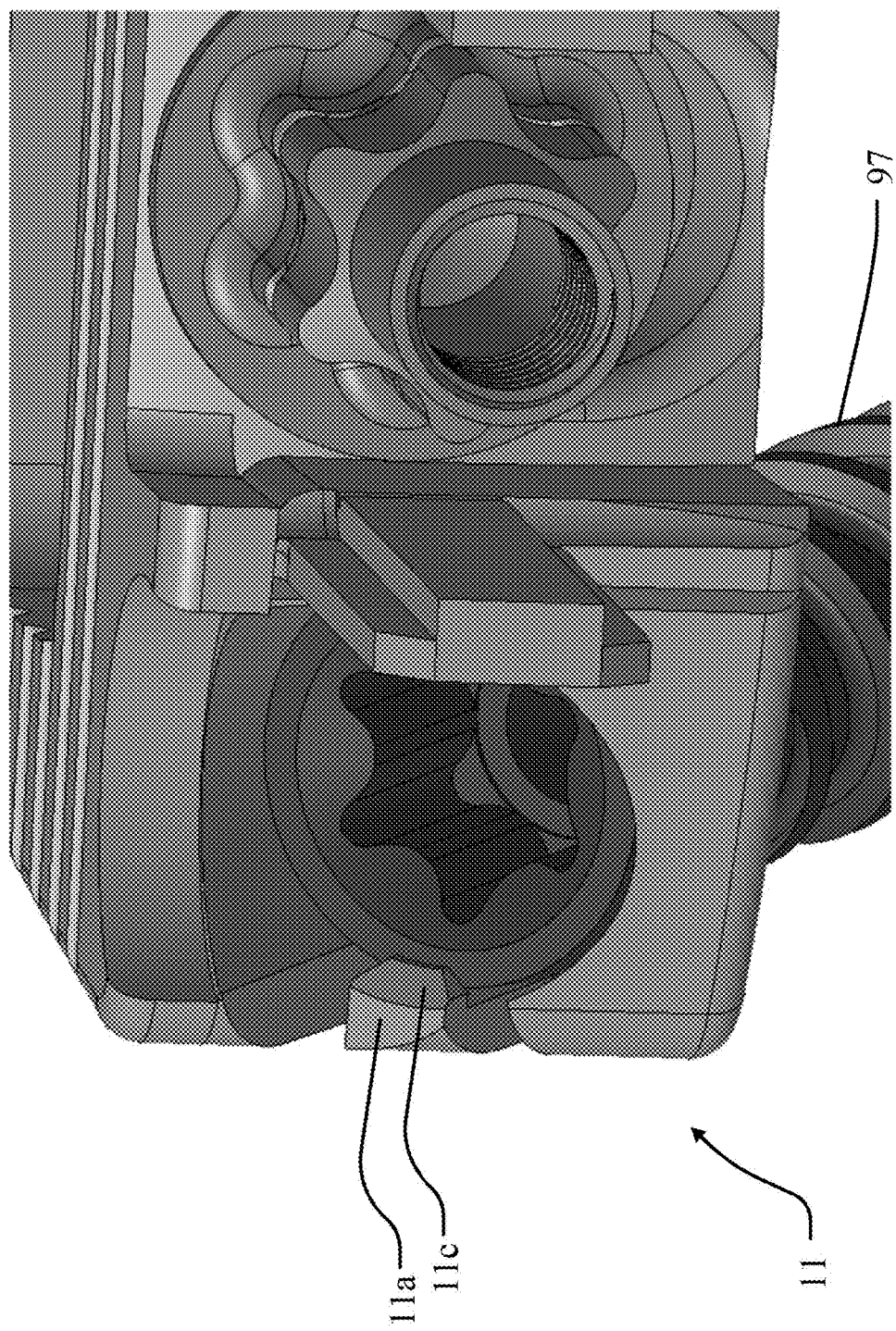
FIG. 19 is a front view of an enlarged area of FIG. 18.
Figure 20:
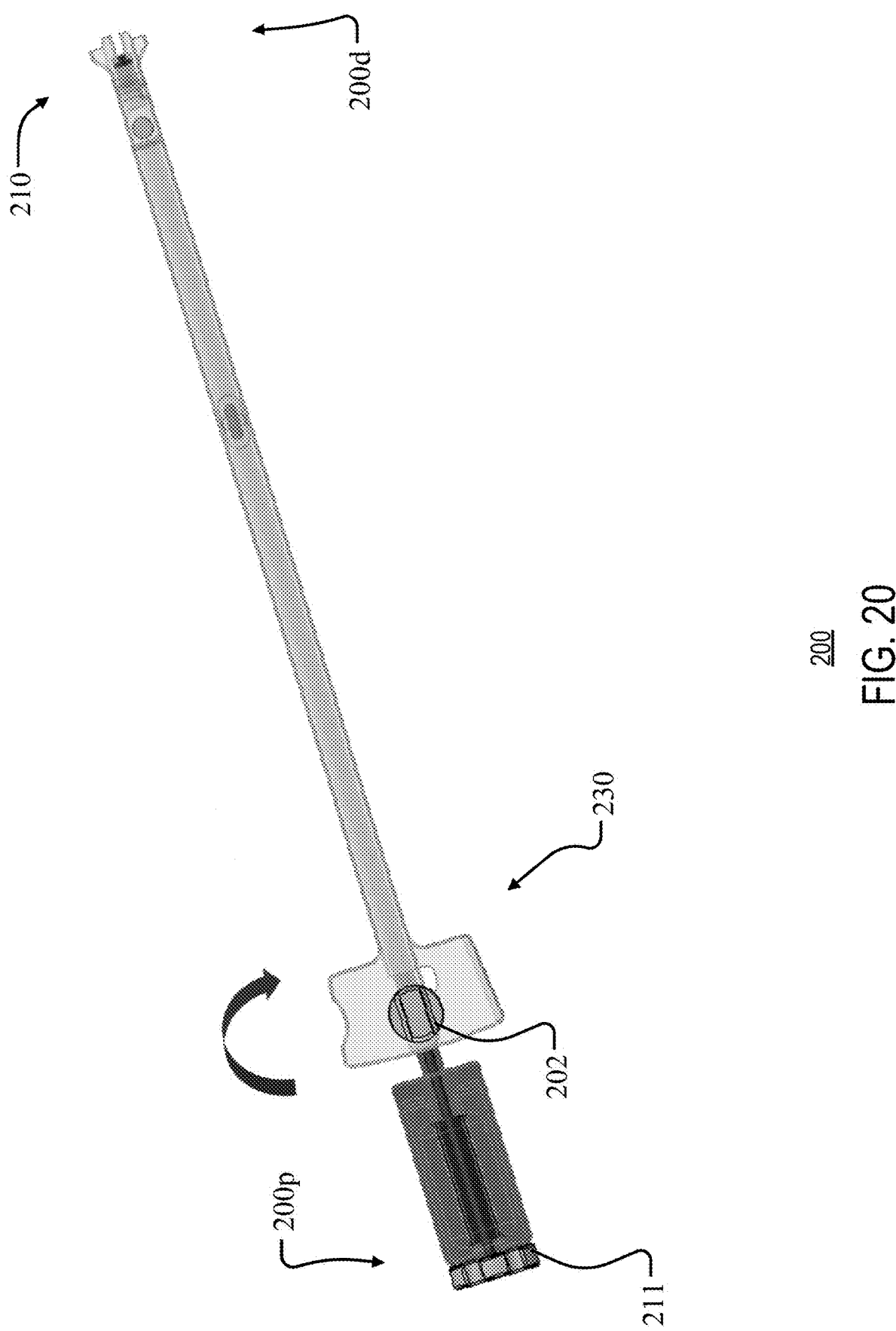
FIG. 20 is a perspective view of an inserter for use with disclosed expandable implants.
Figure 21:
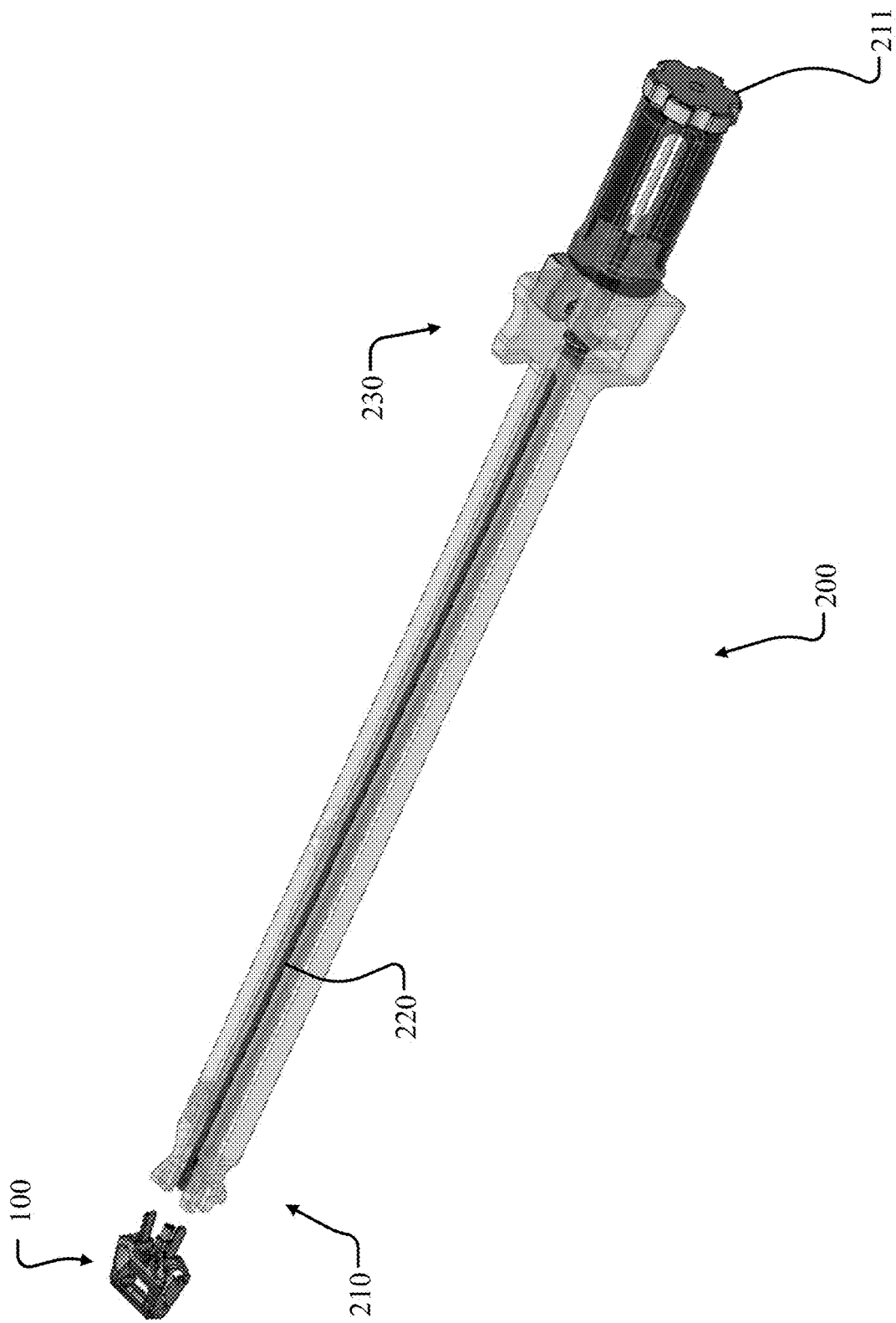
FIG. 21 is a perspective view of an inserter for use with disclosed expandable implants shown in skeleton outlining for ease of understanding.
Figure 22:
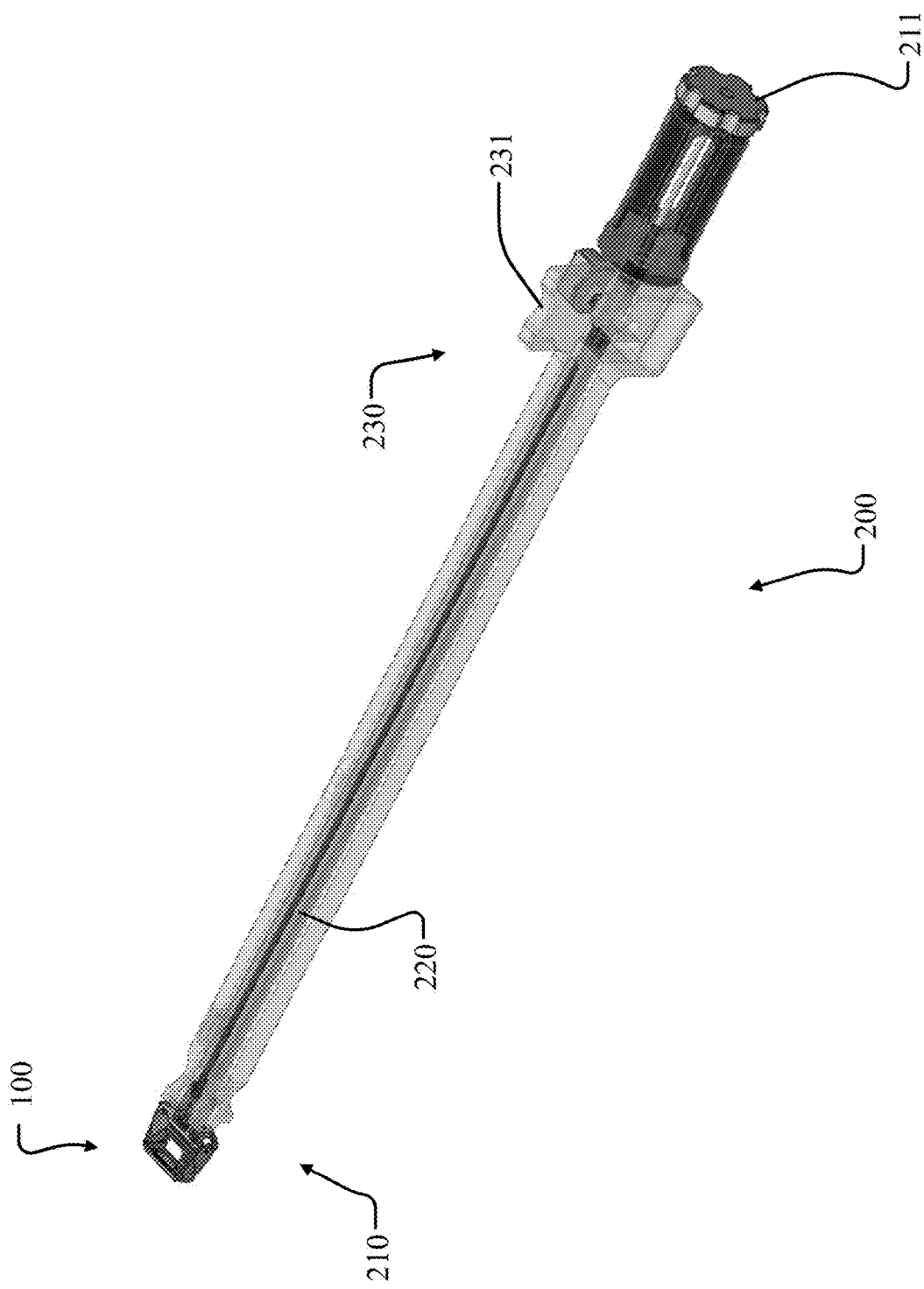
FIG. 22 is a perspective view of an inserter for use with disclosed expandable implants shown in skeleton outlining for ease of understanding.
Figure 23:
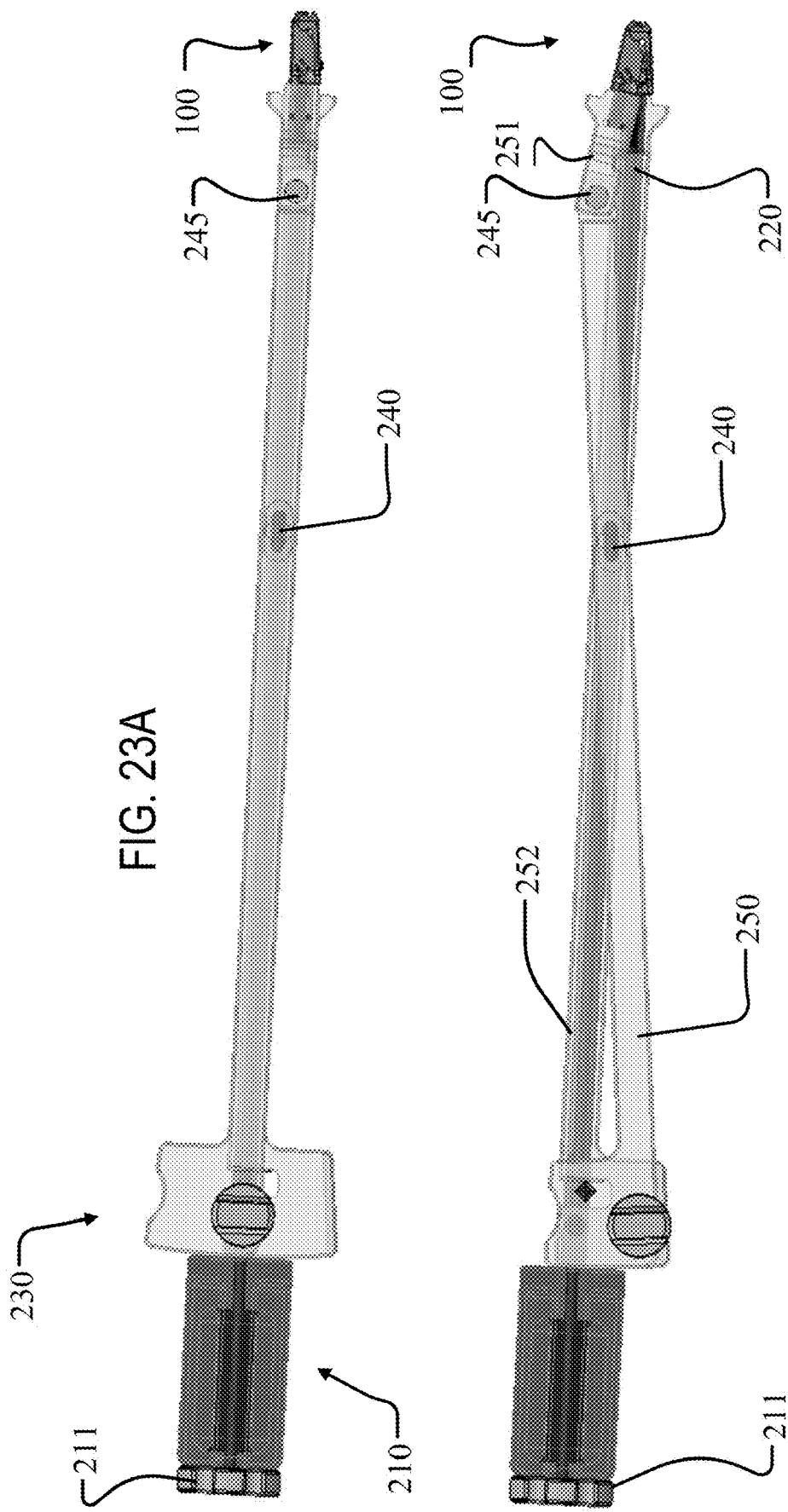
FIG. 23A is a rear view of an inserter in a non-expanded position.
FIG. 23B is a rear view of an inserter in an expanded position.
Figure 24:
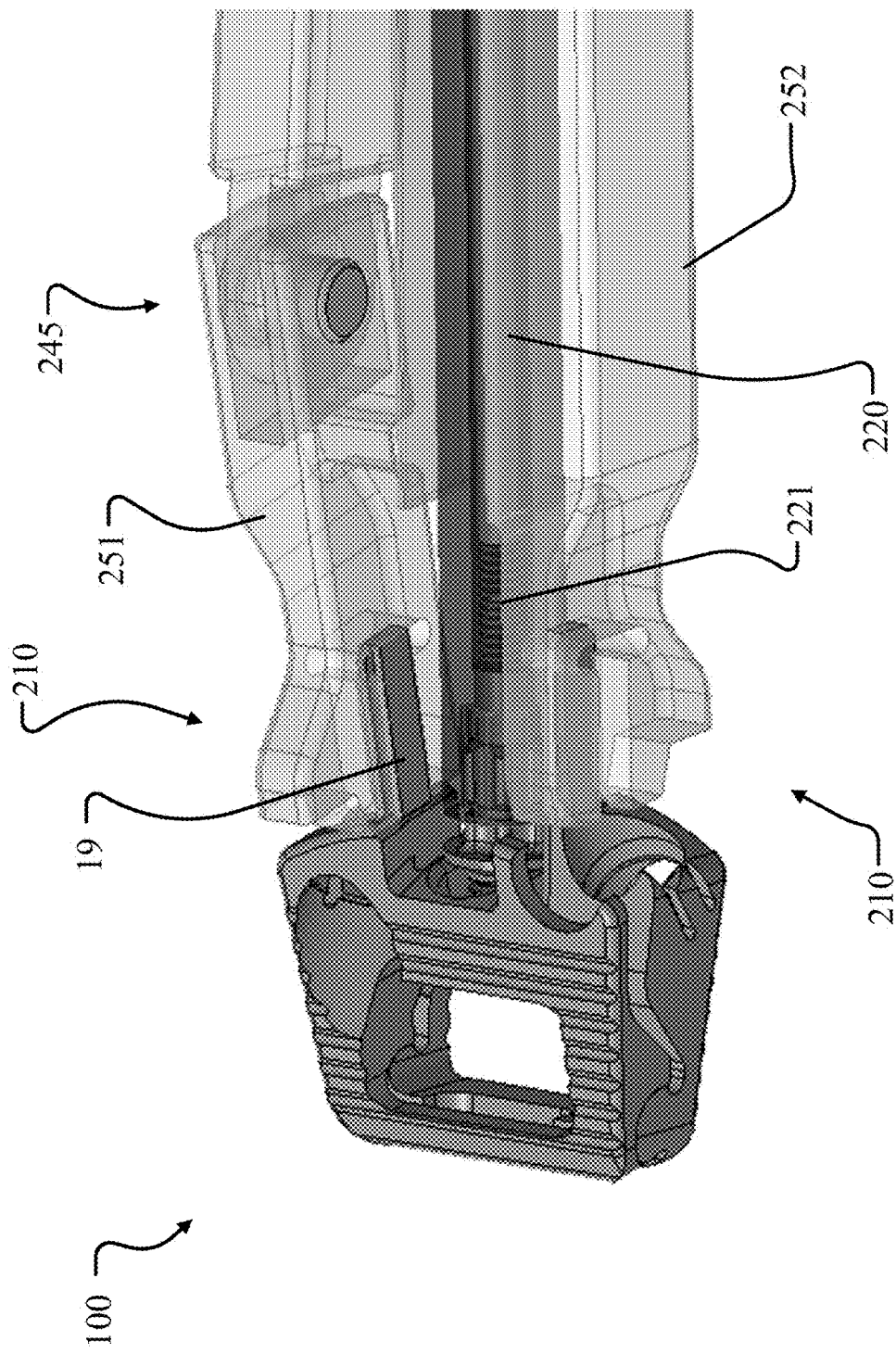
FIG. 24 is an enlarged view of a distal end of an inserter in an expanded position coupled to an example expandable implant in a corresponding expanded position.

FIG. 18 is a front view of an expandable implant showing an area $A_1$ and FIG. 19 is a front view of an enlarged area $A_1$ of FIG. 18. In the example embodiment, bone screw 97 is in a position extending through bone screw aperture 11 where it cannot backout due to bone screw retention mechanism 11a. The bone screw retention mechanism 11a includes an inclined surface 11c such that when bone screw 97 is being installed, an underside of the head portion of bone screw 97 directly contacts the inclined surface 11c thereby pushing the bone screw retention mechanism 11a laterally outward and away from bone screw aperture 11, for example. Thereafter, when bone screw 97 is installed and the head portion of bone screw 97 is beneath inclined surface 11c the bone screw retention mechanism may flex back towards bone screw aperture 11 such that it will prevent bone screw 97 from backing out, e.g., a blocking surface of bone screw retention mechanism 11a may contact an upper surface of the head portion of bone screw 97. In the example embodiment, bone screw retention mechanism 11a comprises flexible arm (or spring tab) having an inclined surface 11c (or ramp) that is disposed on a lateral end of implant 100 adjacent bone screw aperture 11.

Referring generally to FIGS. 20-24 an inserter 200 for use with disclosed expandable implants 100 is illustrated. Inserter 200 may extend in a longitudinal direction from a proximal end 200p to a distal end 200d, for example. Inserter 200 may include a pair of handles 230, a handle lock 202, and mounting arms 210 for securely coupling to mounting tangs 19, 29 of implant 100, for example. Inserter 200 may further include a tightening knob 211 that is connected to a drive shaft 220 having a drive end 221. Drive end 221 may have a size and shape generally corresponding to a size and shape of the various drive features of locking screw 50, for example the internal threaded surface 52, first drive feature 53a, and/or second drive feature 53b. In the example embodiment shown in FIG. 24, drive end 221 includes an end portion having an outside threaded surface with a corresponding size and shape to the internal threaded surface 52 of locking screw 50. In various embodiments, tightening knob 211 may rotate drive shaft 220 and drive end 221 to engage drive end 221 with locking screw 50 and pull implant 100 towards inserter tool 200 such that mounting tangs 19, 29 are securely nested within corresponding channels of mounting arms 210. Additionally, an end user may rotate inserter 200 thereby translating a rotational force through drive end 221 to locking screw 50, e.g., via first drive feature 53a, and/or second drive feature 53b.

As seen best in FIGS. 23A and 23B, inserter 200 may include a pair of handles 230, a stationary arm 252, a primary pivoting arm 250, and a secondary pivoting arm 251. For example, to expand implant 100 an end user may toggle handle lock 202 to an unlocked position and push down on thumb indentation 231 of the handle 230 that is connected to the primary pivoting arm 250 and secondary pivoting arm 251. In doing so, primary pivoting arm 250 may pivot with respect to medial pivot point 240 and secondary pivoting arm 251 may pivot with respect to distal pivot point 245, for example. The path of travel of secondary pivoting arm 251 may lift up on the corresponding mounting tang 19 or 29 and cause the superior endplate 10 and inferior endplate 20 to separate from one another at the proximal end, for example. In doing so, an end user can lordose implant 100 to a desired angle. For example, as seen best in FIG. 24, secondary pivoting arm 251 has lifted up on mounting tang 19, which is nested in a corresponding channel of mounting arm 210.

Figure 25:
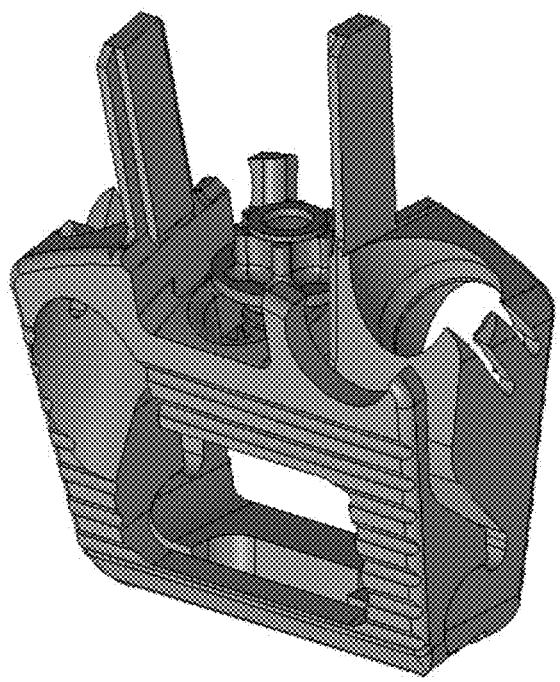
FIG. 25 is a perspective view of an expandable implant in an expanded configuration after a breakoff portion of a locking screw has been broken off.

Once implant 100 is lordosed to a desired configuration, an end user may rotate drive shaft 220 and drive end 221 to tighten locking screw 50 as explained previously. After locking screw 50 is relatively tight, the end user may continue to apply a rotational force to locking screw 50 until a proximal portion comprising the cylindrical part having an internal threaded surface 52, and the first drive feature 53a breaks off at breakoff location 55. For example, once locking screw 50 is tightened to a designed torque, the locking screw 50 may shear off as explained previously. At least one advantage of utilizing the locking screw 50, is that it may prevent over tightening which can cause deformation to implant 100. As shown in FIG. 25, implant 100 has been expanded to a desired position and/or lordotic angle. Additionally, locking screw 50 has locked the relative position of the superior endplate 10 with respect to the inferior endplate 20 and the proximal portion of locking screw 50 has been broken off as explained above.

Figure 26:
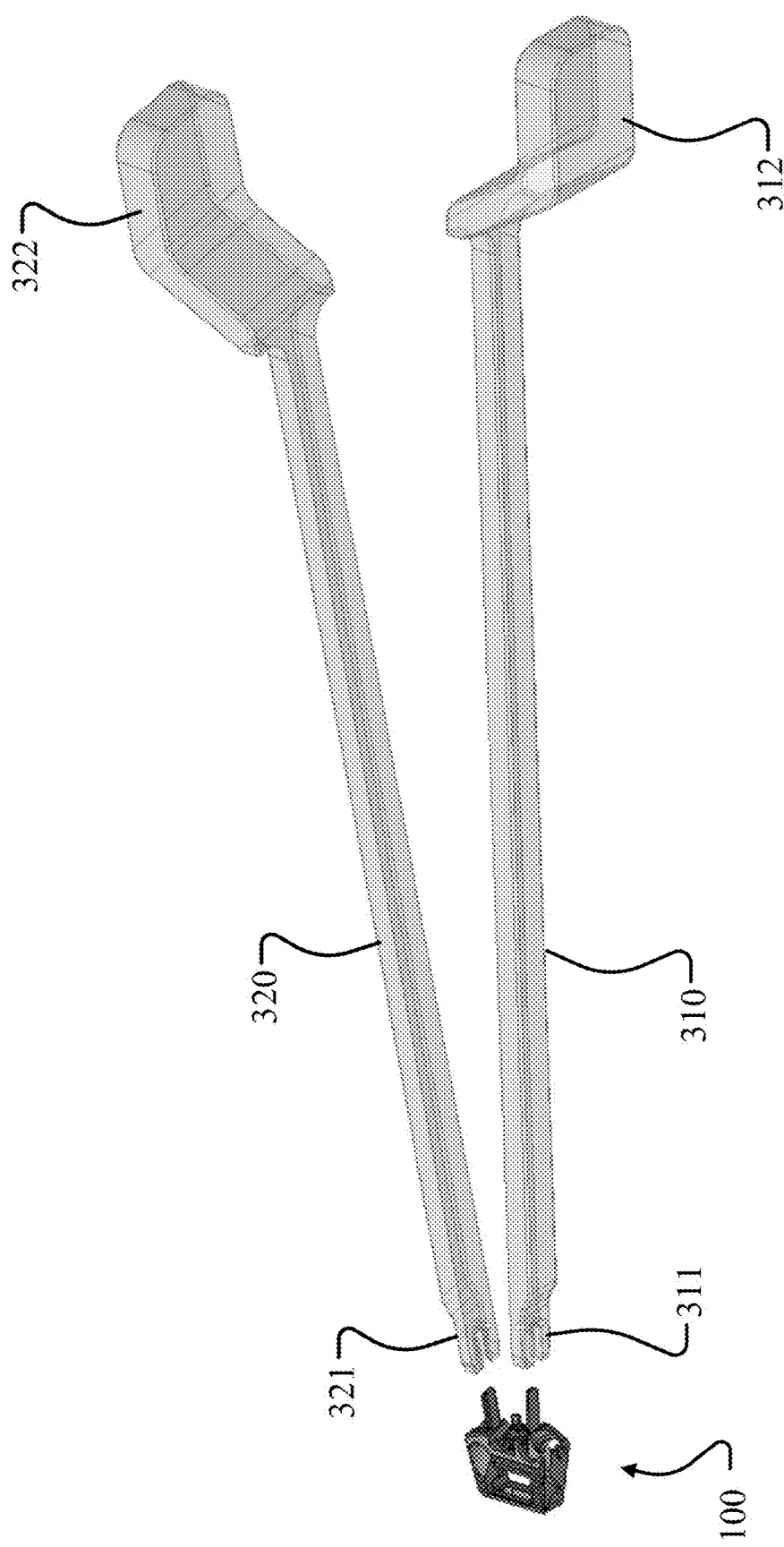
FIG. 26 is a perspective view of a surgical instrument for use with disclosed expandable implants.
Figure 27:
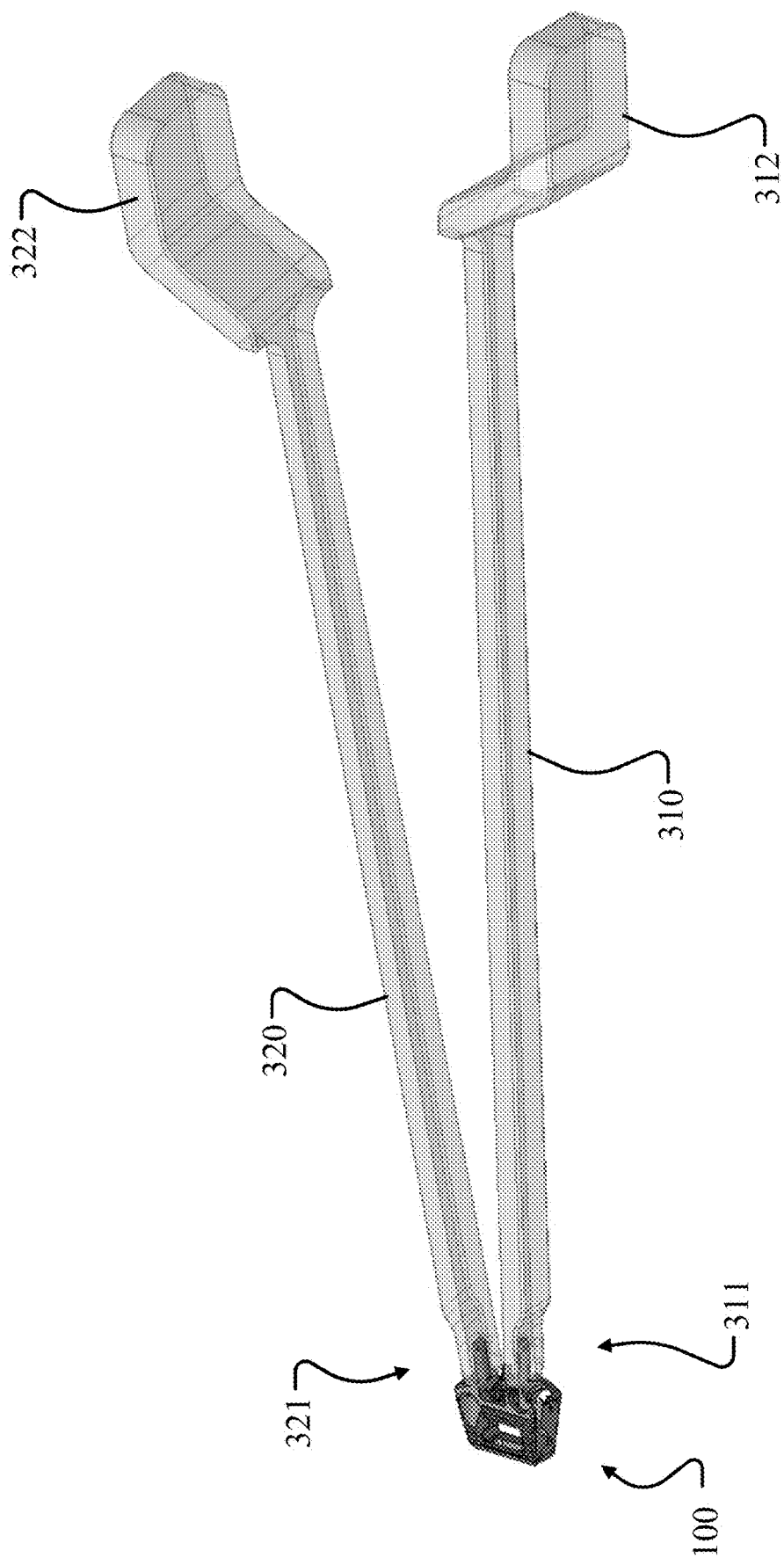
FIG. 27 is a perspective view of a surgical instrument for use with disclosed expandable implants.

FIGS. 26 and 27 are various views of a surgical instrument 300 for use with disclosed expandable implants 100. In some embodiments, surgical instrument 300 may be referred to as a breakoff instrument and may be used to breakoff the mounting tangs 19, 29 of implant 100. In the example embodiment, surgical instrument 300 comprises a first instrument 310 and a second instrument 320. First instrument 310 may extend in a longitudinal direction from handle 312 towards gripping end 311. Similarly, second instrument 320 may extend in a longitudinal direction from handle 322 to gripping end 321. Gripping ends 311, 321 may comprise a channel having a size and shape generally corresponding to mounting tangs 19, 29. For example, as seen best in FIG.

Figure 28:
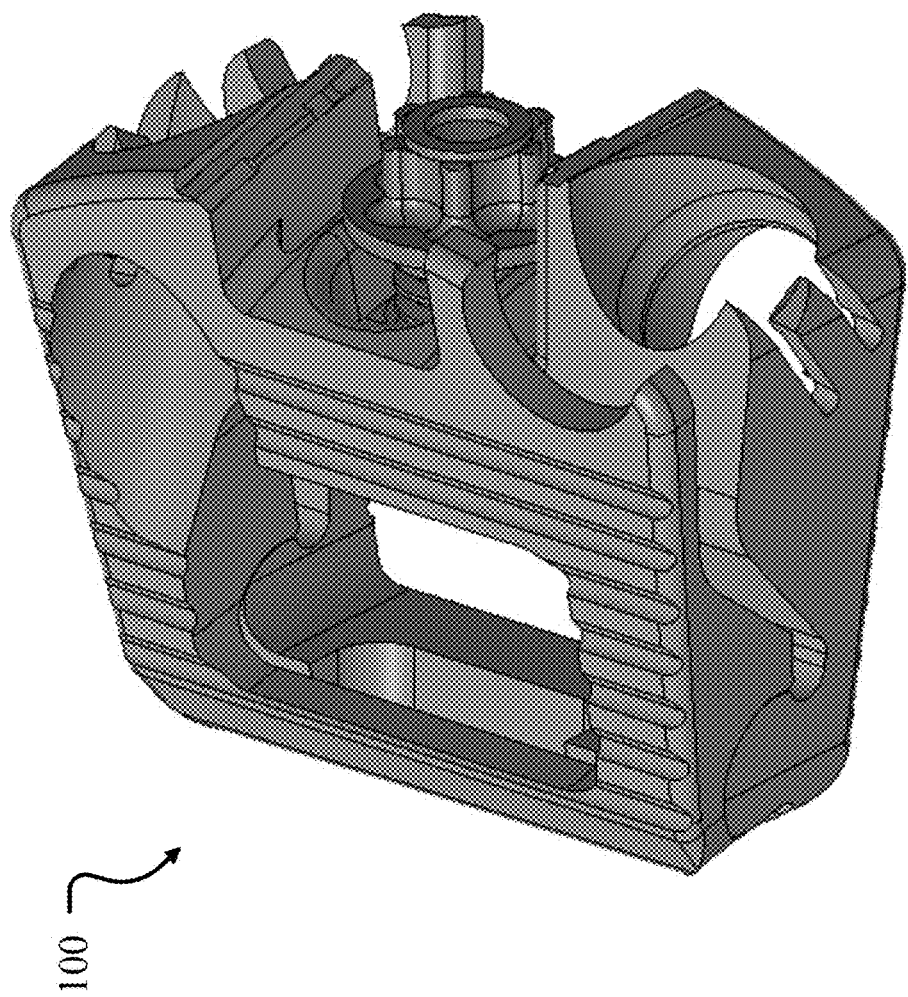
FIG. 28 is a perspective view of an expandable implant after the mounting tangs have been broken off.

27, the mounting tangs 19, 29 may be insert inside of the corresponding channels of gripping ends 311, 321. After the mounting tangs 19, 29 are nested within gripping ends 311, 321 an end user may push laterally outward and/or inward against handles 312, 322 to breakoff the corresponding mounting tang 19, 29. For example, as shown in FIG. 28 expandable implant 100 is in an expanded and lordosed configuration and the proximal portion of locking screw 50 and tangs 19, 29 have been broken off.

Figure 29:
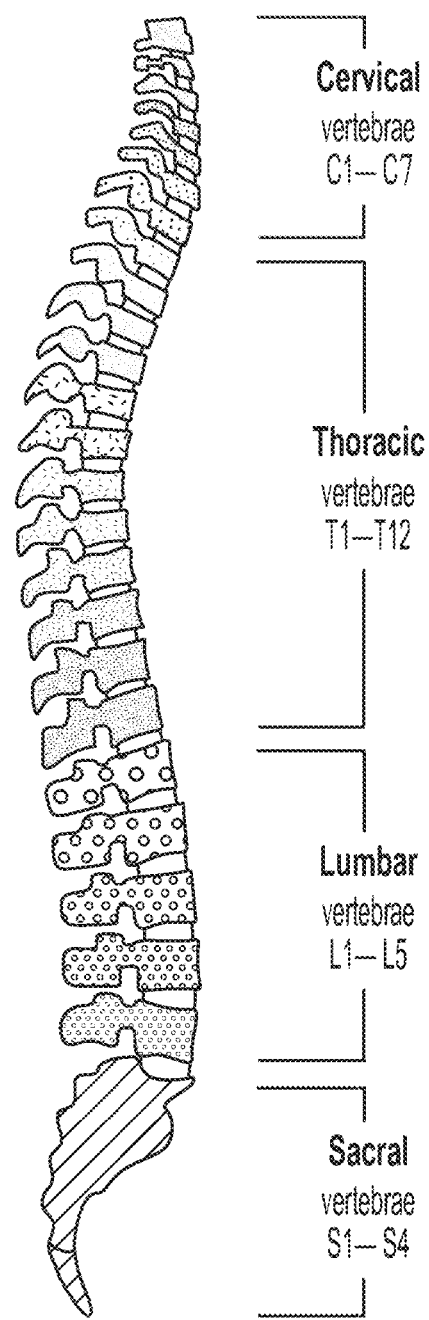
Figure 30:
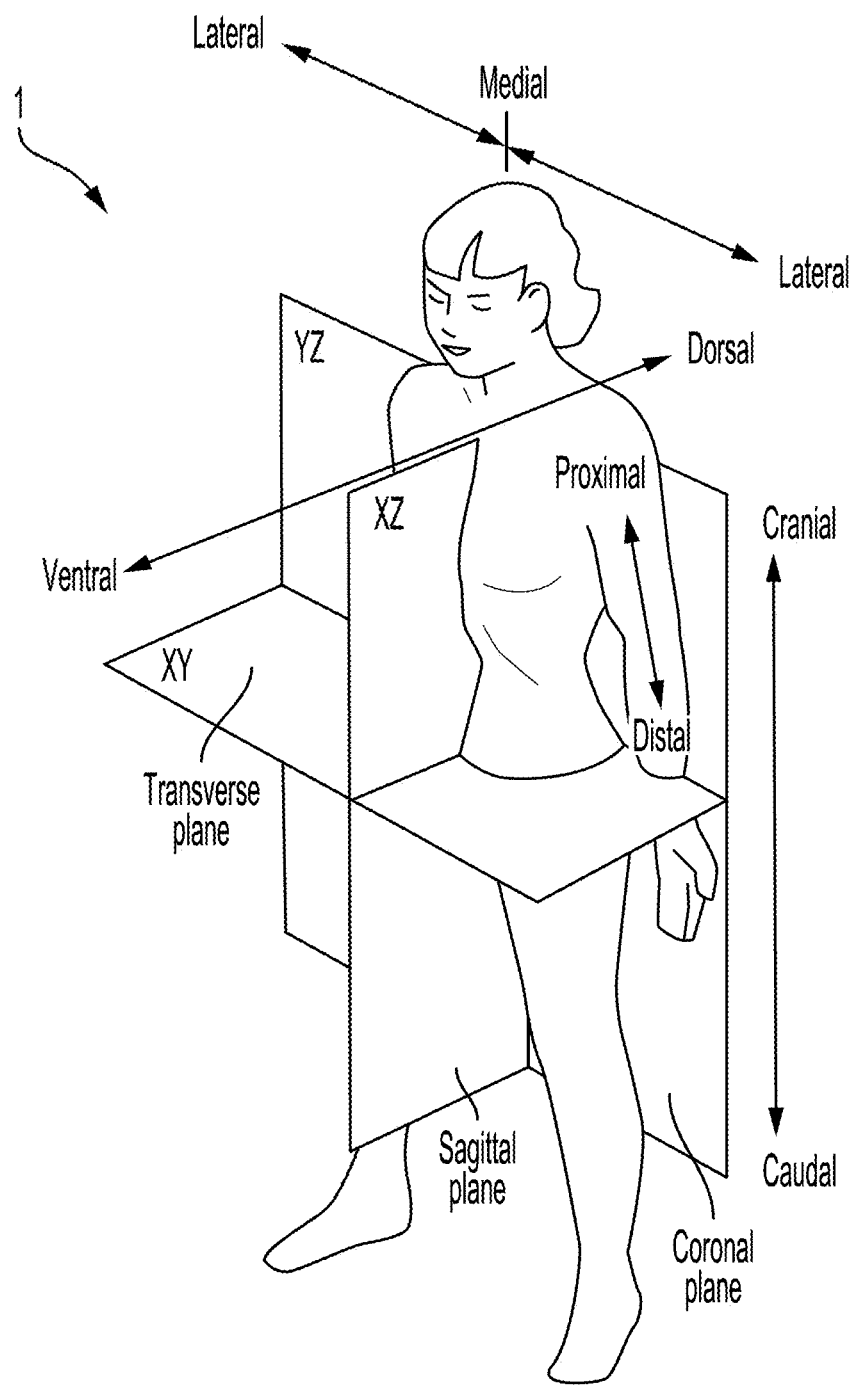
FIG. 30 is a reference drawing showing various planes and reference directions of which the various disclosed implant embodiments may move in or act in with respect to a patient.

FIG. 29 is a reference drawing showing the human spine of which various disclosed implant embodiments may be installed in. FIG. 30 is a reference drawing showing various planes and reference directions of which the various disclosed implant embodiments may move in or act in with reference to a patient 1.

Referring generally to FIGS. 31-37 a second implant 400 embodiment is disclosed. Implant 400 may include the same, similar, and/or substantially the same components and functionality as explained above with respect to implant 100. Accordingly, duplicative description will be omitted. It shall be understood that various components and functionality of implant 100 are readily combinable with implant 400 and vice versa unless the context clearly indicates otherwise.

Figure 31:
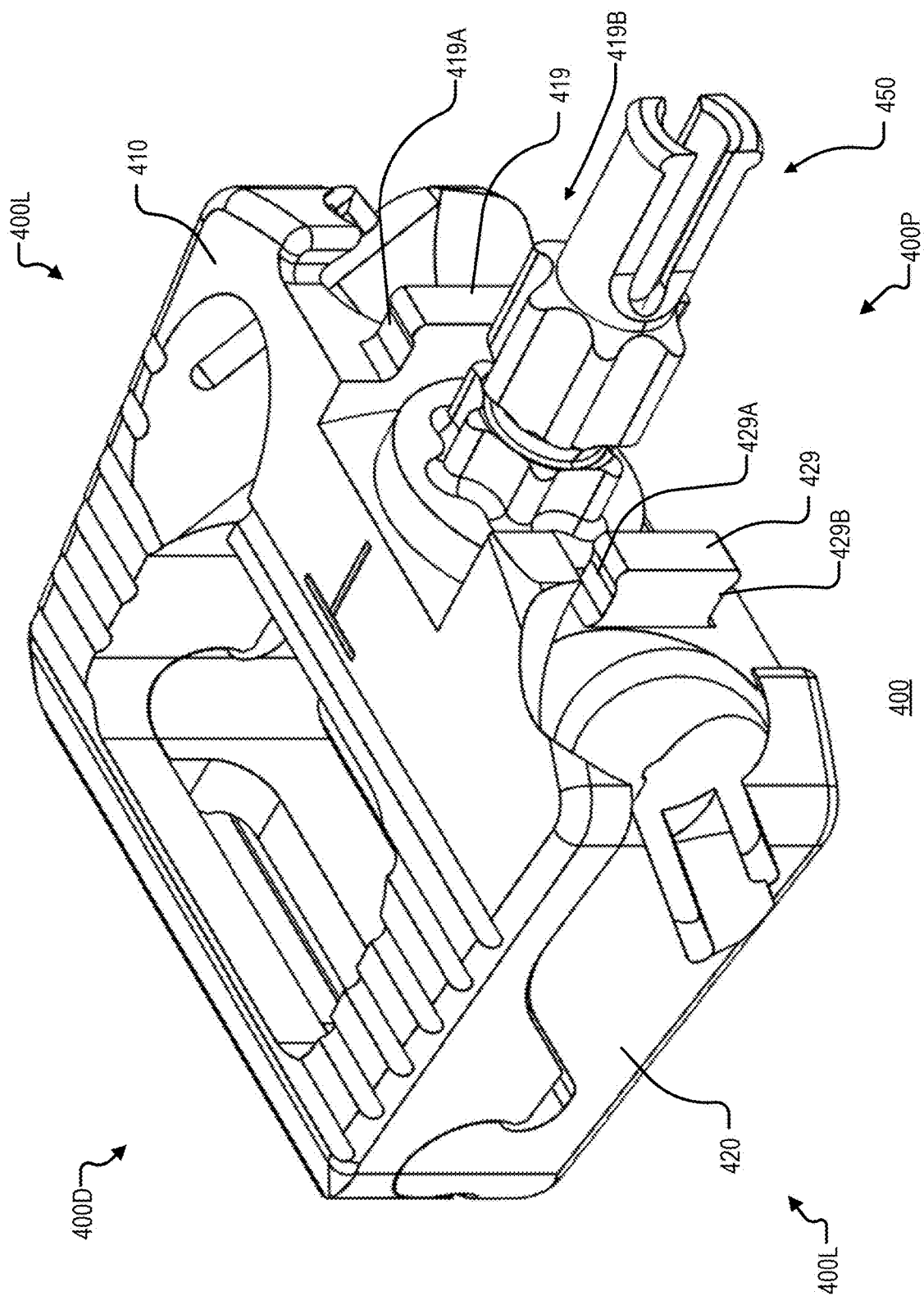
FIG. 31 is a perspective view of a second implant embodiment.

FIG. 31 is a perspective view of a second implant 400 embodiment. In this embodiment, implant 400 extends in a proximal-to-distal direction between a proximal end 400P and a distal end 400D and extends in a width-wise direction between a first lateral end 400L and a second lateral end 400L. Additionally, implant 400 includes a superior endplate 410 and an inferior endplate 420 having substantially similar features and functionality as explained above with respect to superior endplate 10 and inferior endplate 20 of implant 100, for example. However, in this embodiment, superior endplate 410 may include a first griping protrusion 419 extending in a proximal direction from the proximal end 400P of the superior endplate 410. Similarly, inferior endplate 420 may include a second griping protrusion 429 extending in a proximal direction from the proximal end 400P of the inferior endplate 420. In this embodiment, a size and shape of first gripping protrusion 419 is substantially the same as a size and shape of the second gripping protrusion 429. However, in other embodiments the first and second gripping protrusions 419, 429 may be differently sized and shaped, e.g., to bias the implant towards a surgical instrument and/or orientation for insertion. In this embodiment, and in the closed position, each gripping protrusion 419, 429 is disposed at approximately the same distance from an axis of rotation of breakoff set screw 450. In this embodiment, gripping protrusions 419, 429 may replace the need for the tangs 19, 29 of implant 100, for example. However, the concepts of utilizing breakoff tangs 19, 29 and gripping protrusions 419, 429 are not necessarily mutually exclusive and attributes of one may be combined and/or modified in view of the other.

In various embodiments, gripping protrusions 419, 429 may include various types of contouring to facilitate grasping of gripping protrusions 419, 429 with a corresponding inserter, for example surface indentations, surface outdents, channeling, etc. In the example embodiment, gripping protrusion 419 comprises a superior gripping surface 419A including an indented portion and an outdented chamfered portion at a proximal most end thereof, for example. Additionally, gripping protrusion 419 comprises an inferior gripping surface 419B including an indented portion and an outdented chamfered portion at a proximal most end thereof, for example. Likewise, gripping protrusion 429 comprises a superior gripping surface 429A including an indented portion and an outdented chamfered portion at a proximal most end thereof, for example. Additionally, gripping protrusion 429 comprises an inferior gripping surface 429B including an indented portion and an outdented chamfered portion at a proximal most end thereof, for example. In this way, gripping protrusions 419 and 429 are shaped like dovetails and a corresponding inserter tool may comprise a corresponding shaped dovetail groove which may grasp onto and/or slip over gripping protrusions 419 and 429 (not illustrated).

Figure 32:
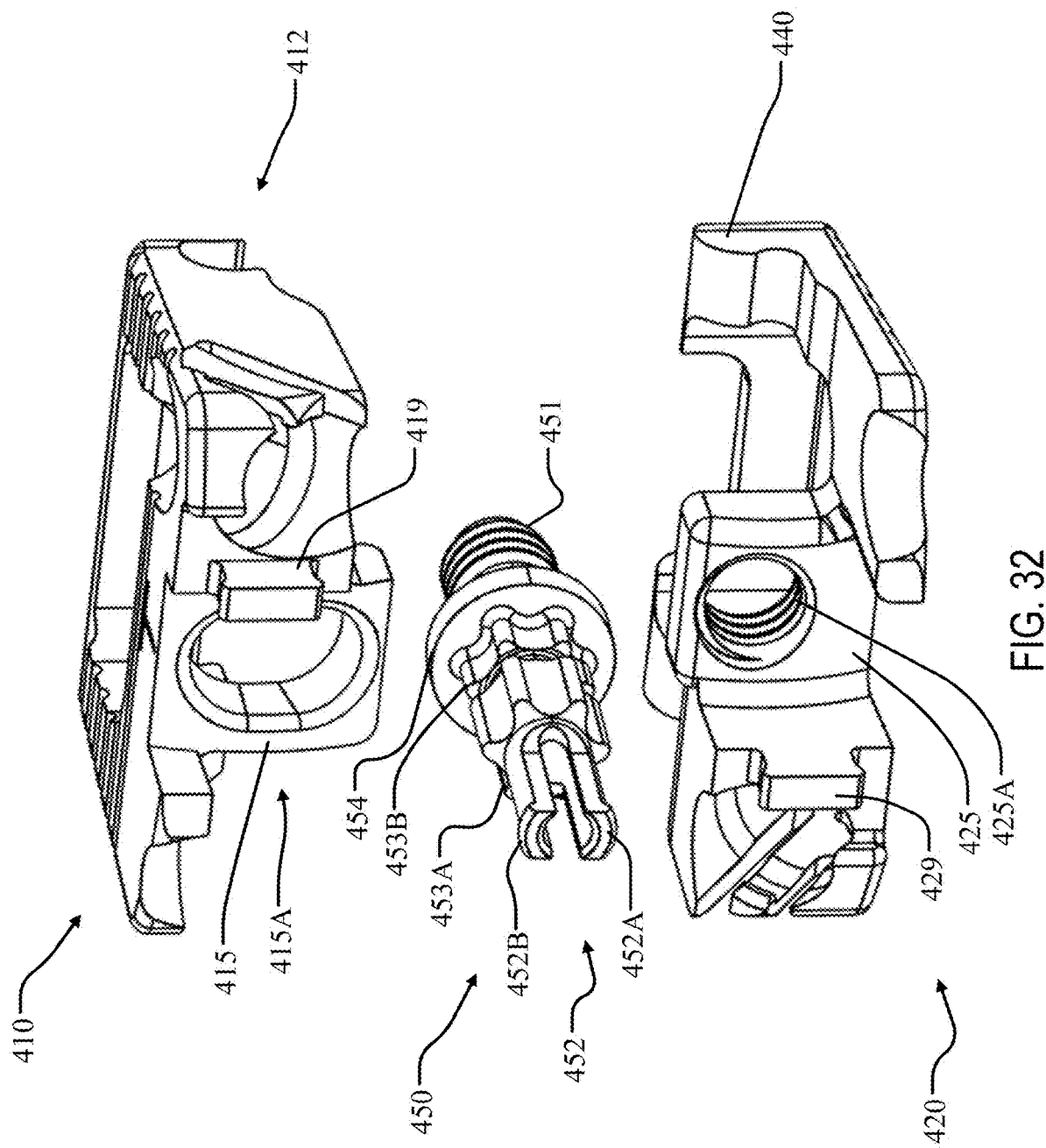
FIG. 32 is a first perspective exploded parts view of the second implant embodiment.
Figure 33:
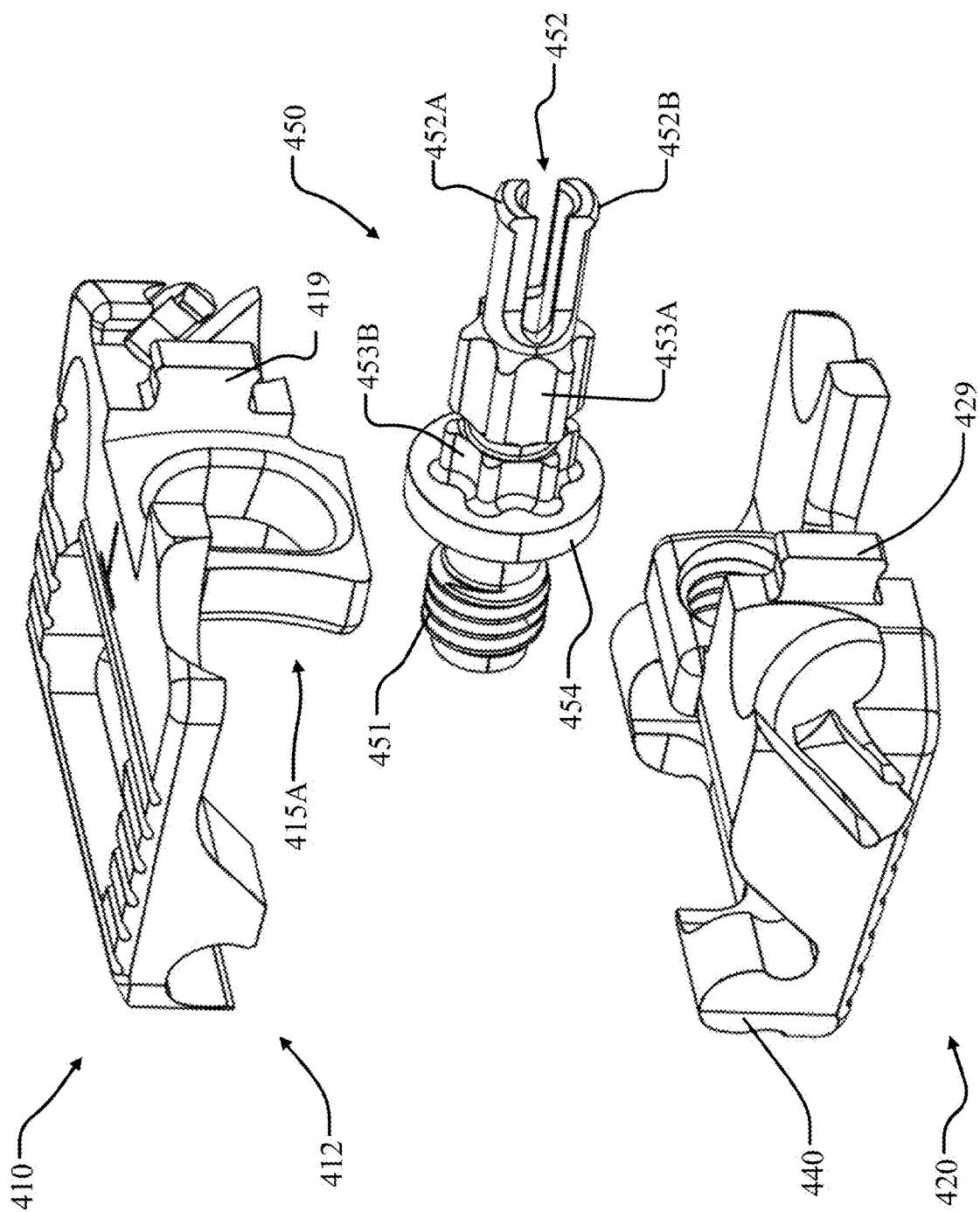
FIG. 33 is a second perspective exploded parts view of the second implant embodiment.
Figure 34:
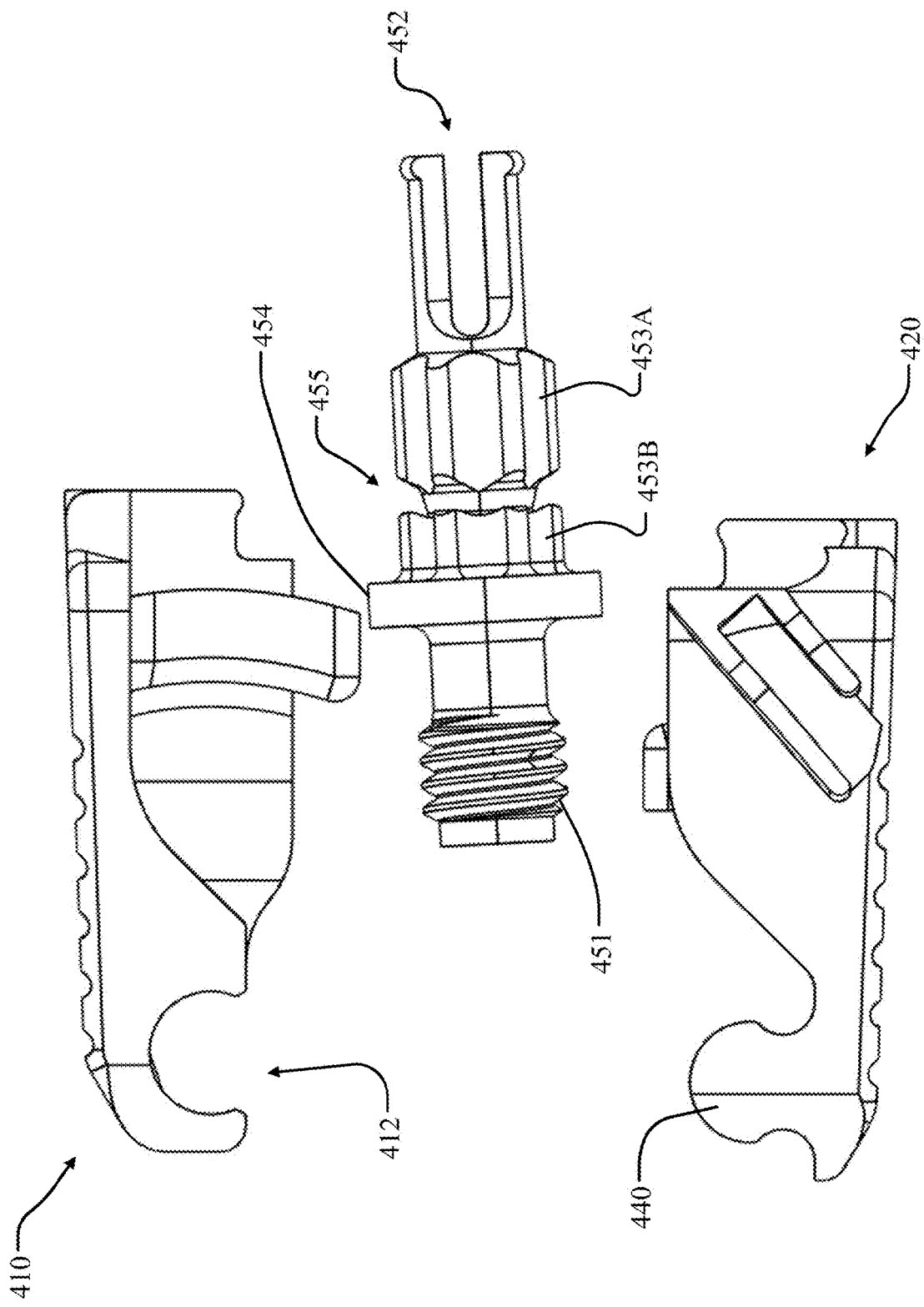
FIG. 34 is a side exploded parts view of the second implant embodiment.

Referring generally to FIGS. 32, 33, and 34 various exploded parts views of implant 400 are illustrated. FIG. 32 is a first perspective exploded parts view of implant 400, FIG. 33 is a second perspective exploded parts view of implant 400, and FIG. 34 is a side exploded parts view of implant 400. In the example embodiment, the superior and inferior endplates 410, 420 of implant 400 may be hingedly coupled together by hinge member 440 and arcuate channel 412 having similar attributes as explained above with respect to hinge member 40 and channel 12 of implant 100, for example. Additionally, superior endplate 410 may also include a core 415 having an aperture 415A and inferior endplate 420 may include a core 425 having a threaded aperture 425A having similar attributes to core 15 and core 25 as explained above with respect to implant 100, for example. In the example embodiment, implant 400 utilizes a breakoff screw 450 for locking of a position of the superior and inferior endplate 410, 420. Breakoff screw 450 may include an external thread pattern 451 on an outside circumferential surface thereof, for example. The external thread pattern 451 of breakoff screw 450 may have a size and shape generally corresponding to the threaded aperture 425a of core 425 of the inferior endplate 420, for example. In various embodiments, an engagement surface 454 may be disposed adjacent and proximal of external thread pattern 451. In the example embodiment, engagement surface 454 is shaped like a washer and is directly connected to breakoff screw 450. However, in other embodiments, engagement surface 454 may be a washer or separated element, for example. In some embodiments, engagement surface 454 may be conically shaped. In the example embodiment, engagement surface 454 may include a relatively planar and/or flat distal surface and/or proximal surface.

In various embodiments, a proximal end of breakoff screw 450 may include a first flexible tang 452A and a second flexible tang 452B defining a discontinuous cylindrical shaped aperture 452 therebetween. Additionally, the first flexible tang 452A and second flexible tang 452B may each include an outdent at a proximal end thereof that is shaped like a segment of an annular ring. In the example embodiment, the first flexible tang 452A may flex inward towards the second flexible tang 452B under loading and vice versa due to the gap between them. At least one advantage of this configuration is that it may facilitate securing breakoff screw 450 to a corresponding drive tool (not illustrated) and the retention of the broken off part. For example, a drive tool may comprise a drive end having a female cavity with a corresponding size and shape to the drive features 453A, 453B. In various embodiments, the cavity may include a pair of indentations corresponding in size and shape to the outdents of flexible tangs 452A and 452B, for example. In use, an end user may align the flexible tangs 452A, 452B with the cavity, push down against the flexible tangs 452A, 452B which may cause them to flex inward towards each other such that they may slide within the cavity until the outdents of flexible tangs 45A and 452B are seated within the corresponding indents of the drive tool. Thereafter, an end user may continue to rotate and or tighten breakoff screw 450. In this way, after a proximal portion of breakoff screw 450 is broken off it may remain retained by the inserter due to the flexible tangs 452A and 452B being seated within the corresponding indents.

In some embodiments, aperture 452 may be understood as a cylindrical protrusion extending in a proximal direction and having a first slit and a second slit extending along the length thereof such that the cyldrical protrusion is compressible. In the example embodiment, a first drive feature 453A and a second drive feature 453B may be disposed adjacent to and distally with respect to a proximal most end of breakoff screw 450. Additionally, first and second drive features 453A, 453B may be disposed proximally with respect to engagement surface 454. In various embodiments, a breakoff location may be positioned between and/or adjacent to drive features 453A, 453B, which will be explained in further detail below. In the example embodiment, drive features 453A, 453B take a hexalobular shape, although various other shapes such as hexaganol, polygonal, torx, etc. are also contemplated. In some embodiments, a surgical drive tool having a corresponding socket may be coupled to drive features 453A and/or 453B to cause rotation of breakoff screw 450. Similarly as explained above with respect to locking screw 50, once breakoff screw 450 has been sufficiently tightened a proximal portion may breakoff and/or shear off while the distal portion may remain coupled to implant 400 locking a relative orientation of superior endplate 410 and inferior endplate 420 in place.

Figure 35:
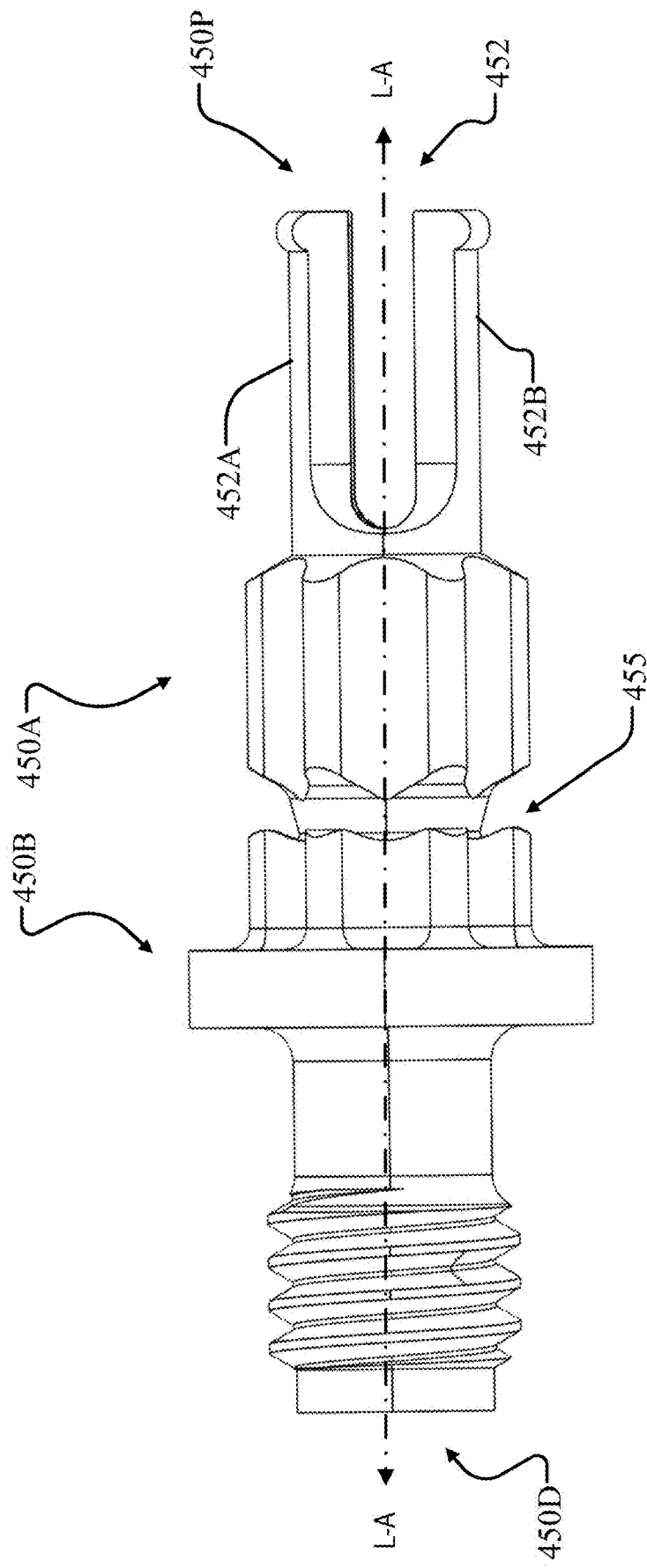
FIG. 35 is a first side view of a breakoff screw having a recessed fracture surface.
Figure 36:
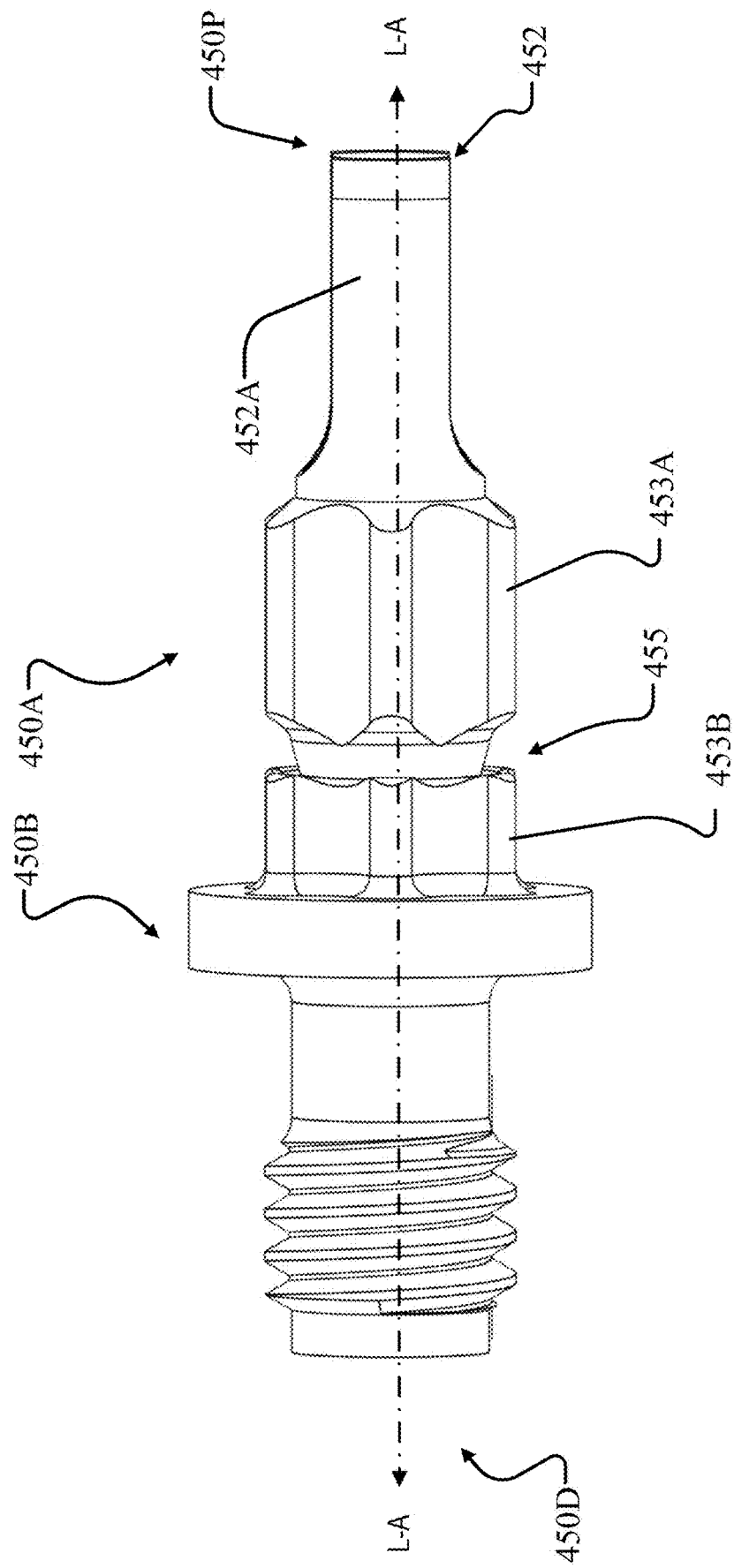
FIG. 36 is a second side view of a breakoff screw having a recessed fracture surface.
Figure 37:
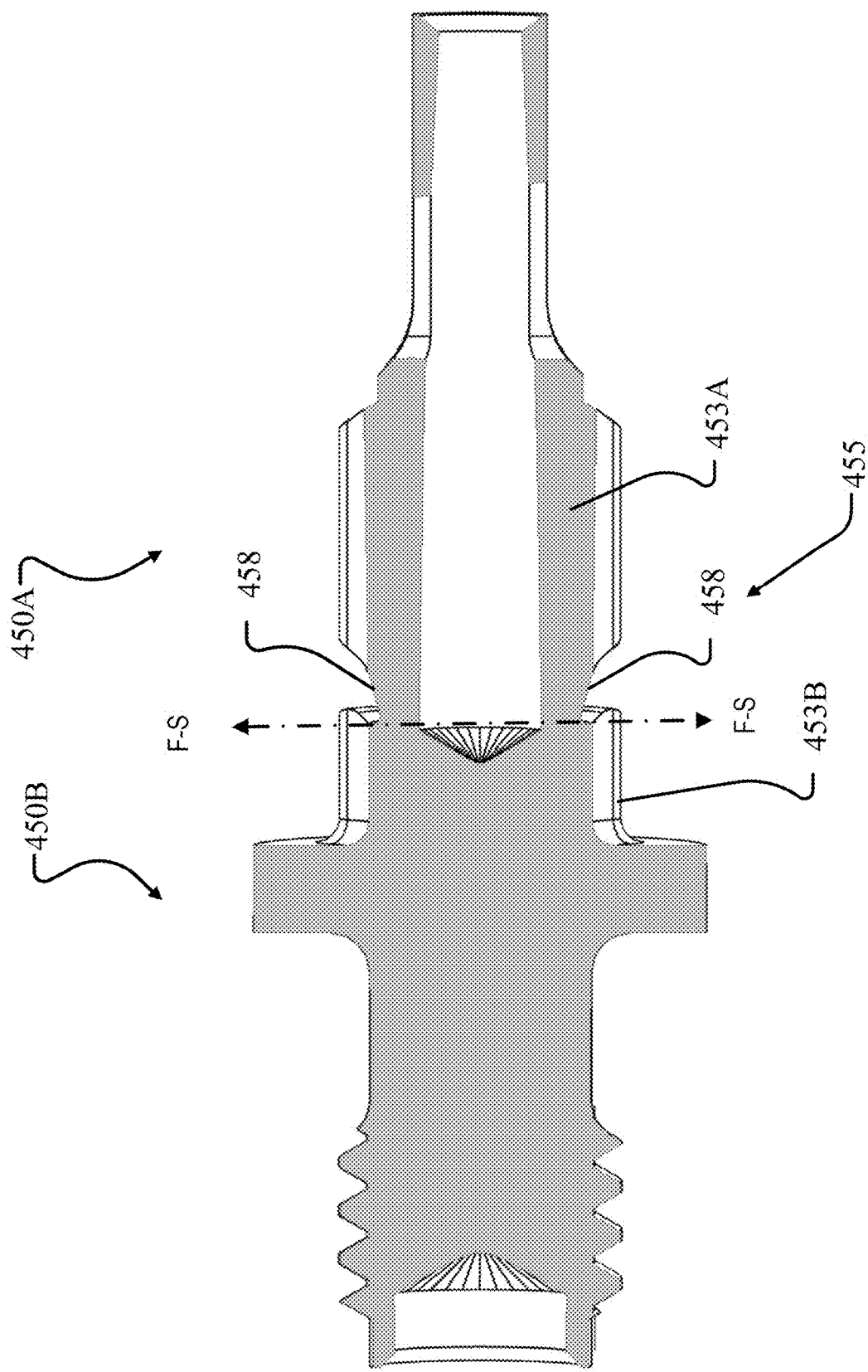
FIG. 37 is a cross section view of a breakoff screw having a recessed fracture surface.

As seen best in FIGS. 35-37, breakoff screw 450 may extend in a longitudinal direction along a longitudinal axis L-A that is coaxially aligned with breakoff screw 450. FIG. 35 is a first side view of breakoff screw 450 in which the superior surface 452A and inferior surface 452B of discontinuous aperture 452 are visible. FIG. 36 is a second side view of a breakoff screw 450 that is rotated about 90 degrees with respect to FIG. 35 in which only the superior surface 452A is visible. With reference to FIG. 37, in various embodiments, breakoff location 455 may comprise a recessed fracture surface F-S that is inset with respect to a leading edge (proximal most edge) of drive feature 453A. At least one advantage of the recessed fracture surface may be that delicate tissue is prevented and/or suppressed from coming into contact with relatively sharp ends of the fracture surface. In the example illustration, a relative location of the recessed fracture surface is represented by dashed lines F-S. In the example embodiment, breakoff location 455 may be considered as the boundary between a proximal portion 450A and a distal portion 450B of breakoff screw 450, for example. In this embodiment, the boundary between drive features 453A and 453B comprises a necked down portion 458 extending from a distal end of drive feature 453A to an inset portion of drive feature 453B that is inset with respect to an outermost and/or proximal most surface of drive feature 453B thereby defining a portion of breakoff set screw 450 having a minimum cross sectional diameter. Accordingly, when breakoff screw 450 is sufficiently tightened within threaded aperture 425A of core 425 such that the breakoff location 455 experiences a sufficient torque the proximal portion 450A may breakoff from the distal portion 450B. For example, when a sufficient rotational force is applied to the proximal end of breakoff screw 450 while a distal end of breakoff screw 450 is stationary, i.e., when breakoff screw 450 is secured in a locked position and a continued rotational force (torque) is applied to the proximal end of breakoff screw 450 the drive feature 453A and cylindrical end having the discontinuous aperture 452 may breakoff. For further explanation in the similar context of implant 100, see FIGS. 10 and 11 and the corresponding discussion thereof.

Figure 38:
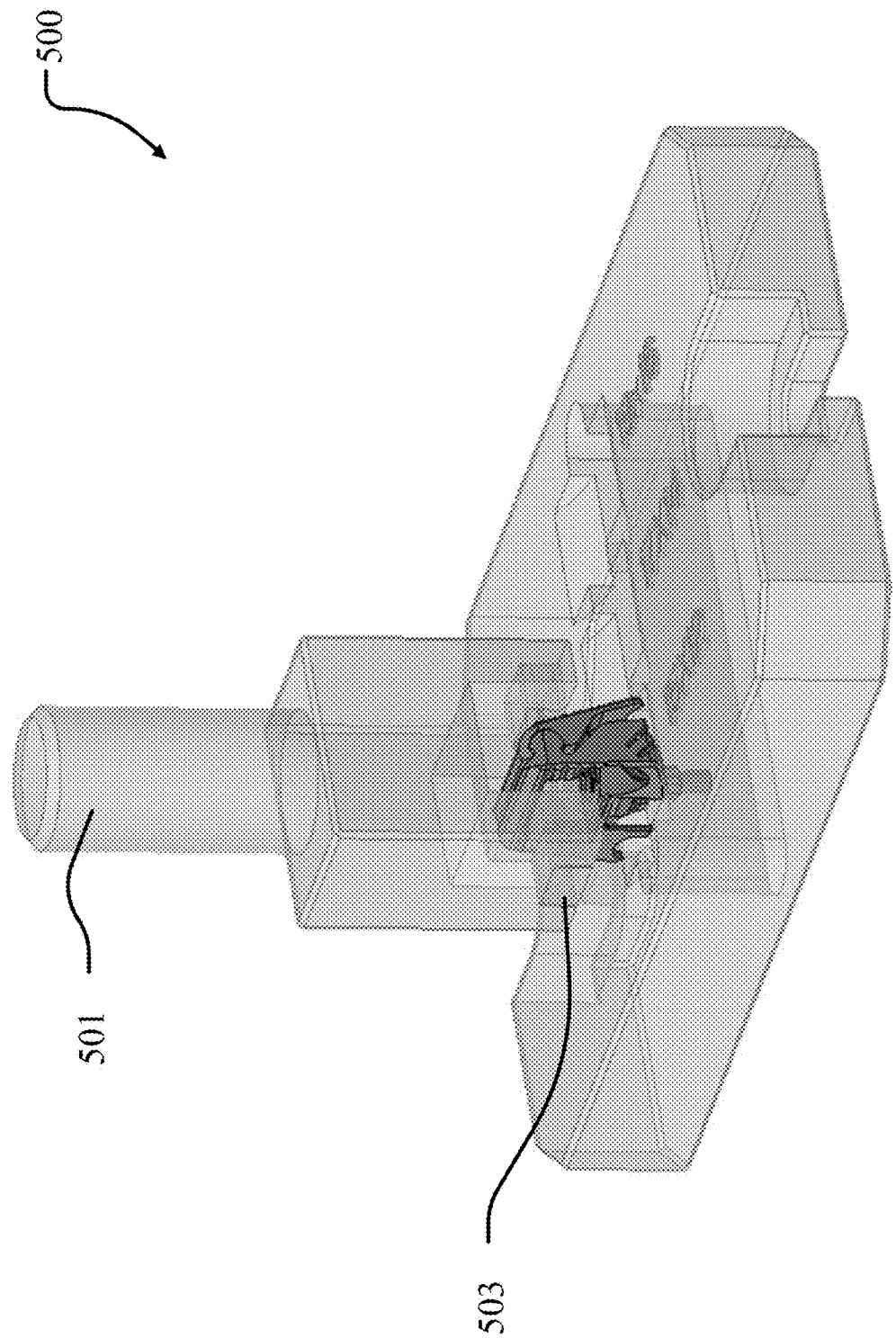
FIG. 38 is a perspective view of a swaging fixture.
Figure 39:
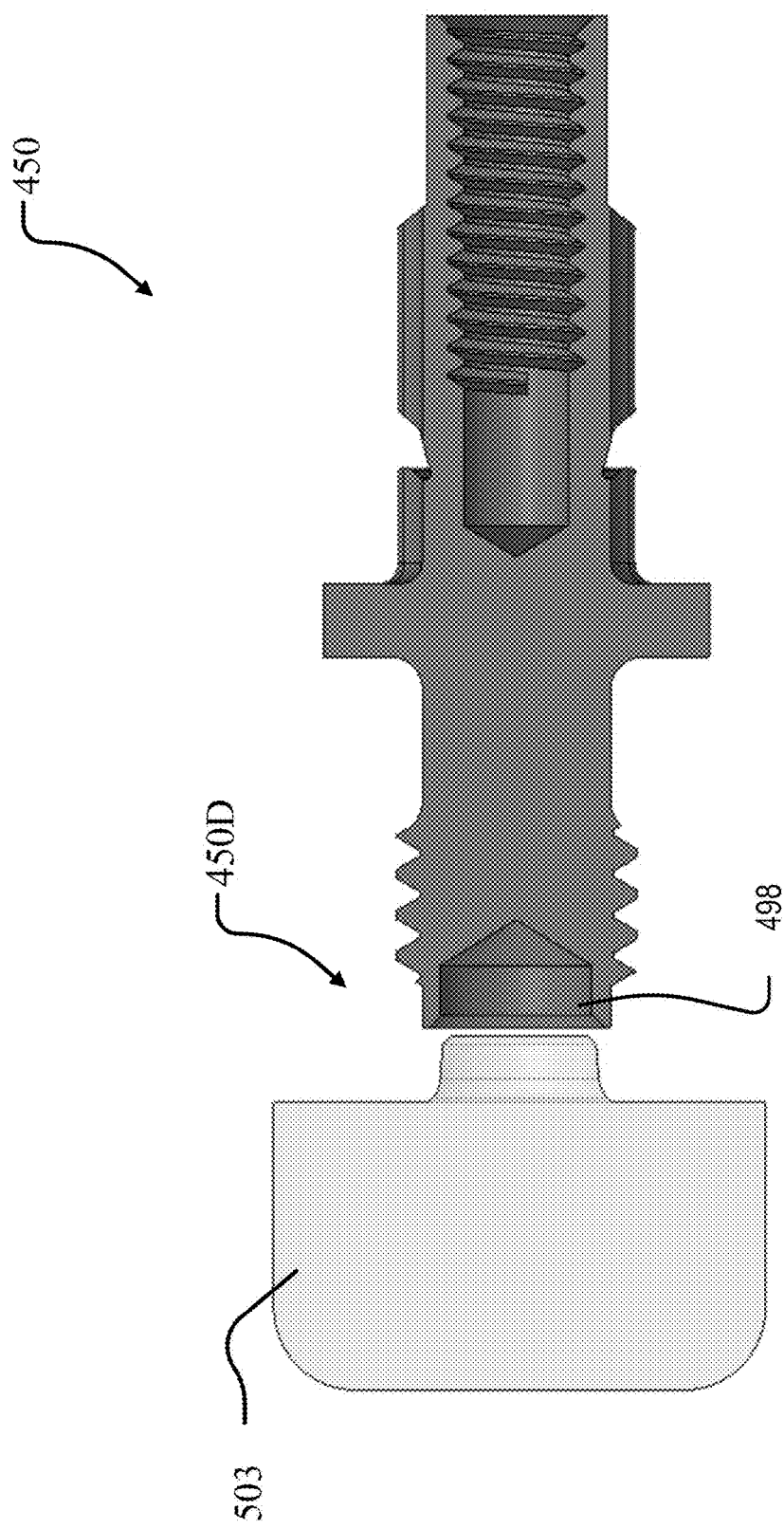
FIG. 39 is a cross section view of a swage mandrel and a distal end of a breakoff screw before the commencement of a swage process.
Figure 40:
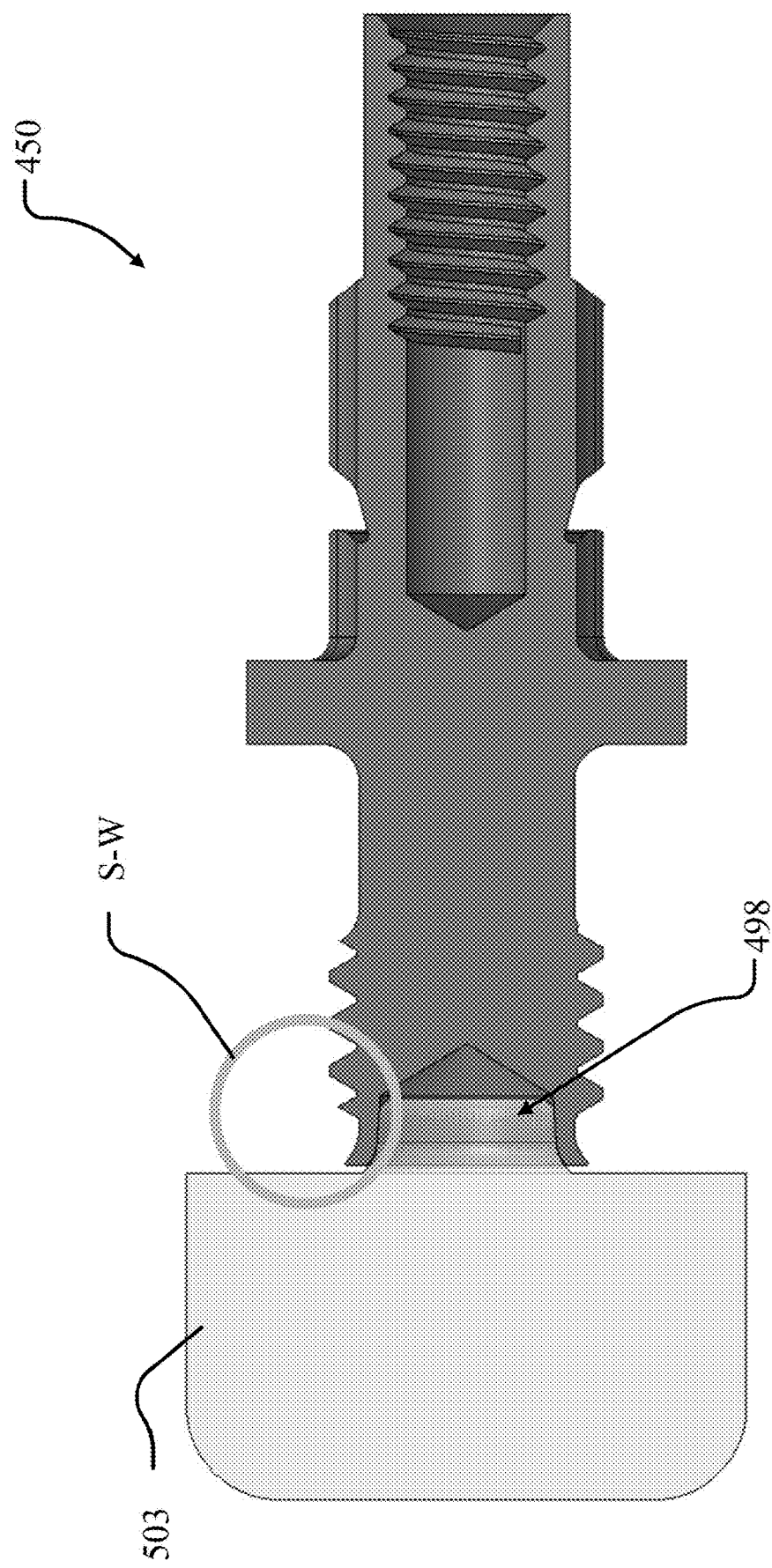
FIG. 40 is a cross section view showing a result of a swage process.

Referring to FIGS. 38-42 an example swaging process is performed to a distal most end of breakoff screw 450. FIG. 38 is a perspective view of a swaging fixture 500, and FIG. 39 is a cross section view of a swage mandrel and a distal end 450D of a breakoff screw 450 before the commencement of a swage process. FIG. 40 is a cross section view showing a result of a swage process, and FIG. 41 is an enlarged view of region S-W of FIG. 40. In the example embodiment, swaging fixture 500 comprises a swaging ram 501 and a swaging mandrel 503 that are supported by the base of the apparatus. The swaging mandrel 503 may include an outdent that corresponds to and is slightly larger than the distal most indent 498 (swage bore) of breakoff screw 450, for example. As seen in region S-W of FIG. 40, when swaging mandrel 503 is advanced into the distal most indent 498 (swage bore) a flared out portion 499 (swaged portion) is formed at a distal most end of breakoff screw 450. An example advantage of a swaged end may be that it facilitates retention of the breakoff screw 450 such that it serves as a stopping structure preventing breakoff screw 450 from backing out of implant 100.

It shall be understood that although breakoff screw 450 is explained concurrently with implant 400 and in the context of an intervertebral implant, the concepts of breakoff screw 450 may be applied to other embodiments used for alternate purposes, for example for use in a pedicle screw to insert in a tulip to tighten down a rod. It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Referring generally to FIGS. 42-51, a third implant 400Z and a surgical tool 600 for use with various implants is disclosed. FIGS. 42A-42B illustrate a third embodiment of an implant 400Z. Implant 400Z may have the same, similar, and/or substantially the same components and functionality as explained above with respect to implant 400, for example. Accordingly, duplicative description will be omitted. A difference may be that breakoff screw 450 does not include the discontinuous cylindrical shaped aperture 452 (see FIG. 34) having tangs 452A, 452B, for example. Rather, breakoff screw 450, to the extent included, may include a continuous cylindrical shaped aperture 452Z without the discontinuity. In some embodiments, a similar screw may be used that is not a breakoff screw but rather may be referred to as a locking screw. Additionally, in this embodiment, implant 400Z may include a first gripping indentation 419Z and a second gripping indentation 429Z (see FIG. 42A) in lieu of the gripping protrusions 419, 429 (as shown in FIG. 33), for example. In various embodiments, first gripping indentation 419Z may be formed as a part of the superior endplate 410 and second gripping indentation 429Z may be formed as a part of the inferior endplate 420, for example.

In various embodiments, gripping indentations 419Z, 429Z may include various types of contouring to facilitate coupling with a corresponding surgical tool 600. In this embodiment, gripping indentations 419Z, 429Z each comprise a slotted indentation extending in a proximal to distal direction with a curved superior surface 419S, 429S and a curved inferior surface 419I, 429I. Additionally, gripping indentations 419Z, 429Z each have an open channel portion 419X, 429X adjacent the breakoff screw 450, to the extent a breakoff screw is included. As will be explained in further detail below, corresponding gripping protrusions of a surgical tool 600 may have a substantially similar size and shape to the gripping indentations 419Z, 429Z, for example.

Figure 42A:
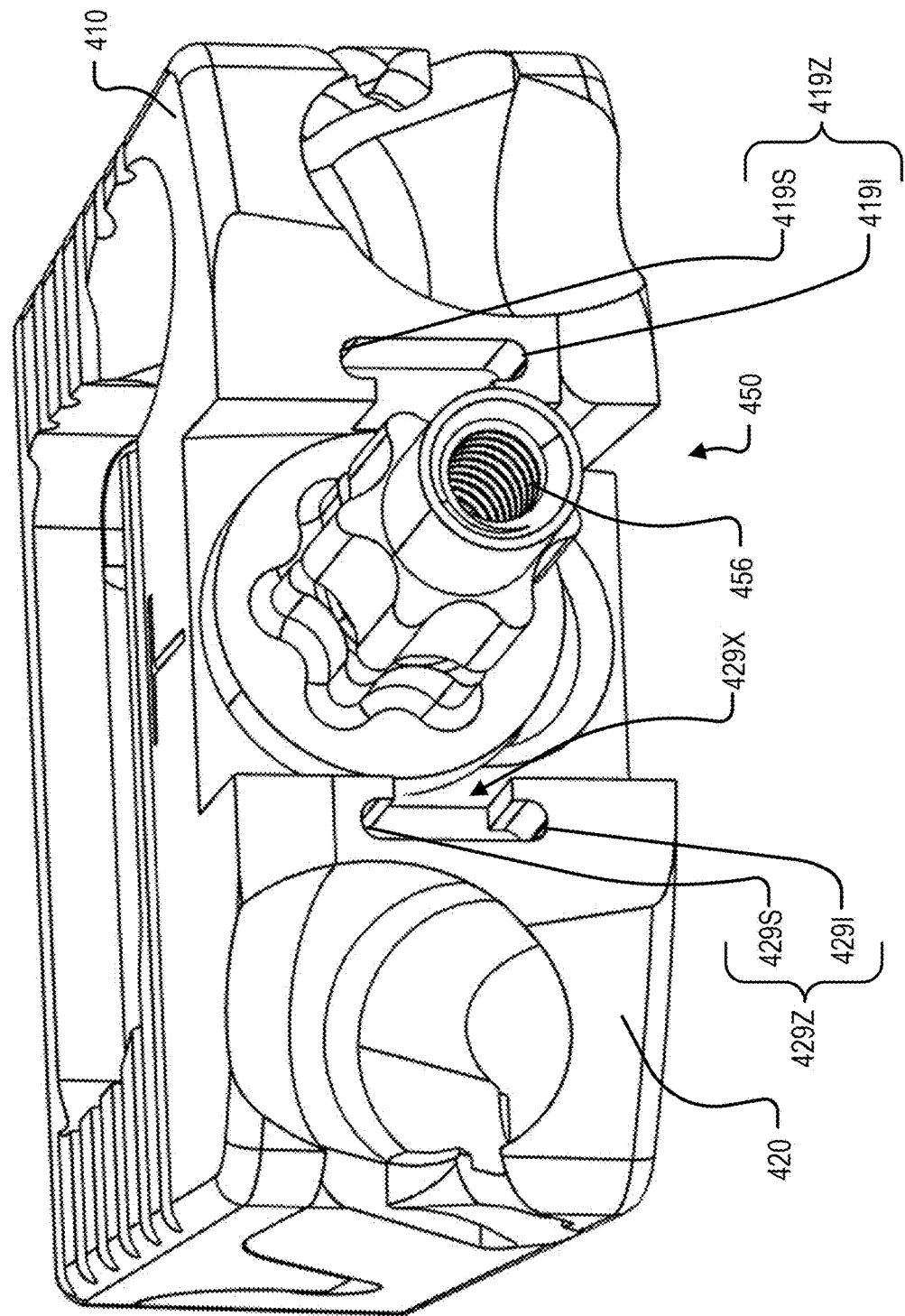
FIG. 42A is a front perspective view of a third implant embodiment.
Figure 42B:
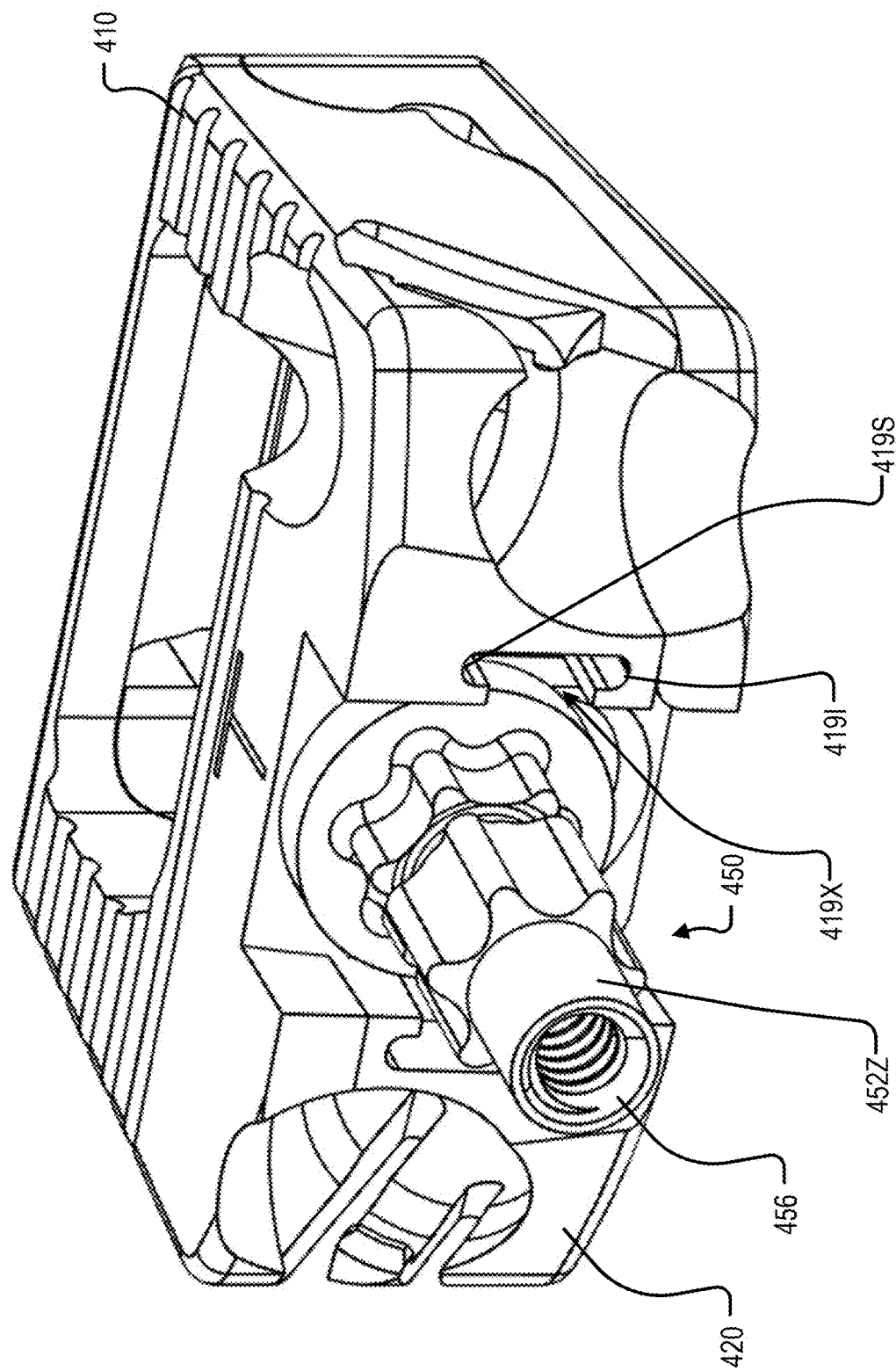
FIG. 42B is an alternate front perspective view of a third implant embodiment.
Figure 43A:
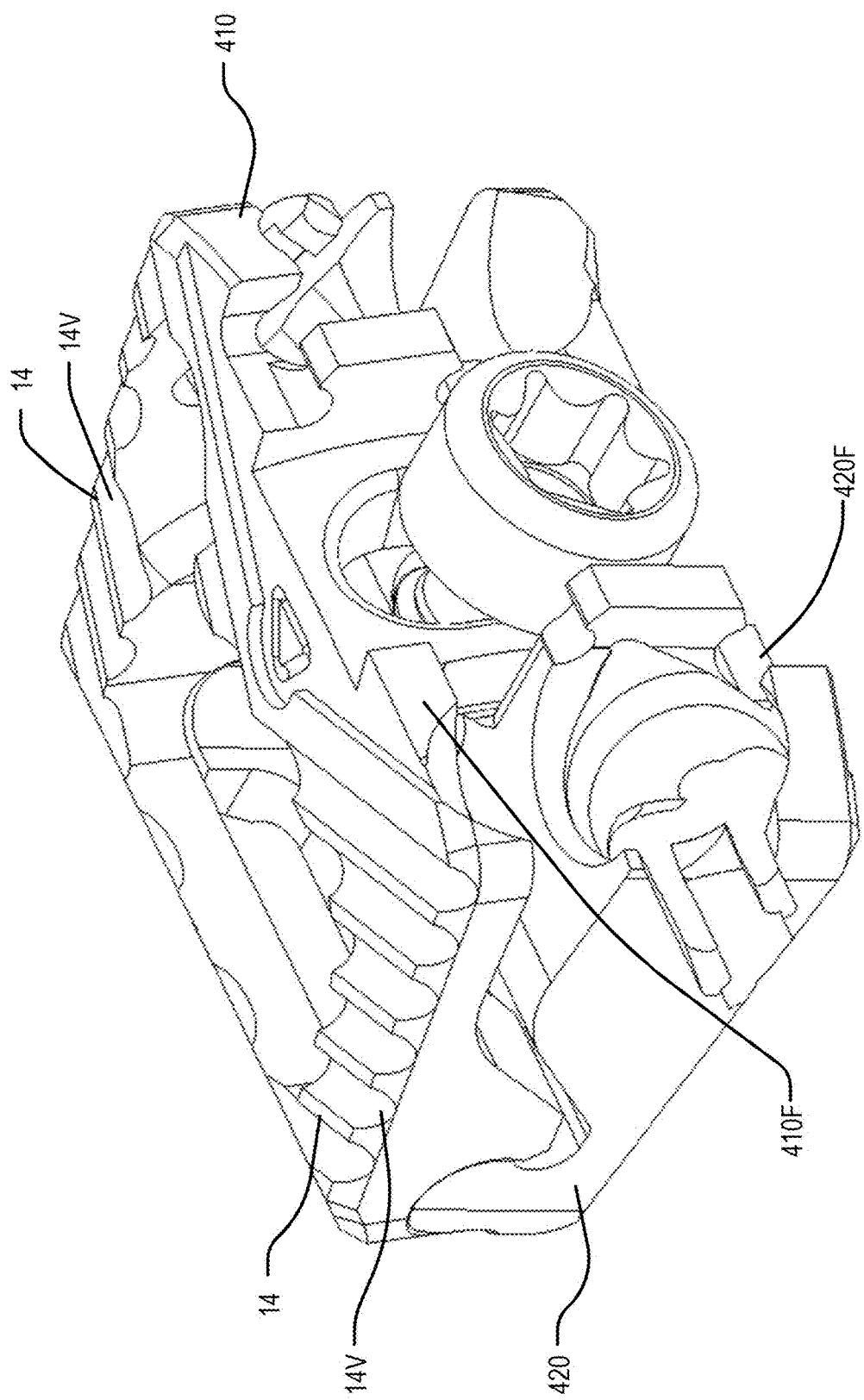
FIG. 43A is a front perspective view of an implant having angled engagement features.

FIGS. 43A-43B illustrate a similar embodiment as FIGS. 42A-42B. As shown, the implant 400Z includes angled engagement features 14. In the example embodiment, engagement features 14 extend diagonally across the exposed uppermost surface of superior endplate 410 and across the exposed lowermost surface of inferior endplate 420. The engagement features 14 comprise flattened top rails that are sequentially spaced apart with rounded bottom valleys 14V therebetween. As seen best in the top down view of FIG. 43B, the engagement features 14 of the superior endplate 410 are oriented at an angle β with respect a proximal face 410F of the superior endplate 410. Similarly, the engagement features 14 of the inferior endplate 420 are oriented at an angle β with respect a proximal face 420F of the inferior endplate 420 (see FIG. 43A). In various embodiments, the angle β may be about 20-40 degrees and in at least one embodiment the angle β may be angled at about 30 degrees. At least one advantage of this orientation may be a relatively greater resistance and/or suppression of expulsion of the implant 400Z relative to embodiments in which engagement features solely extend horizontally across the implant 400Z. In the example embodiment of FIGS. 43A-43B, by orienting the engagement features 14 diagonolly, the implant 400Z may resist expulsion in multiple directions, e.g., forward flexion/extension and lateral bending.

Figure 44:
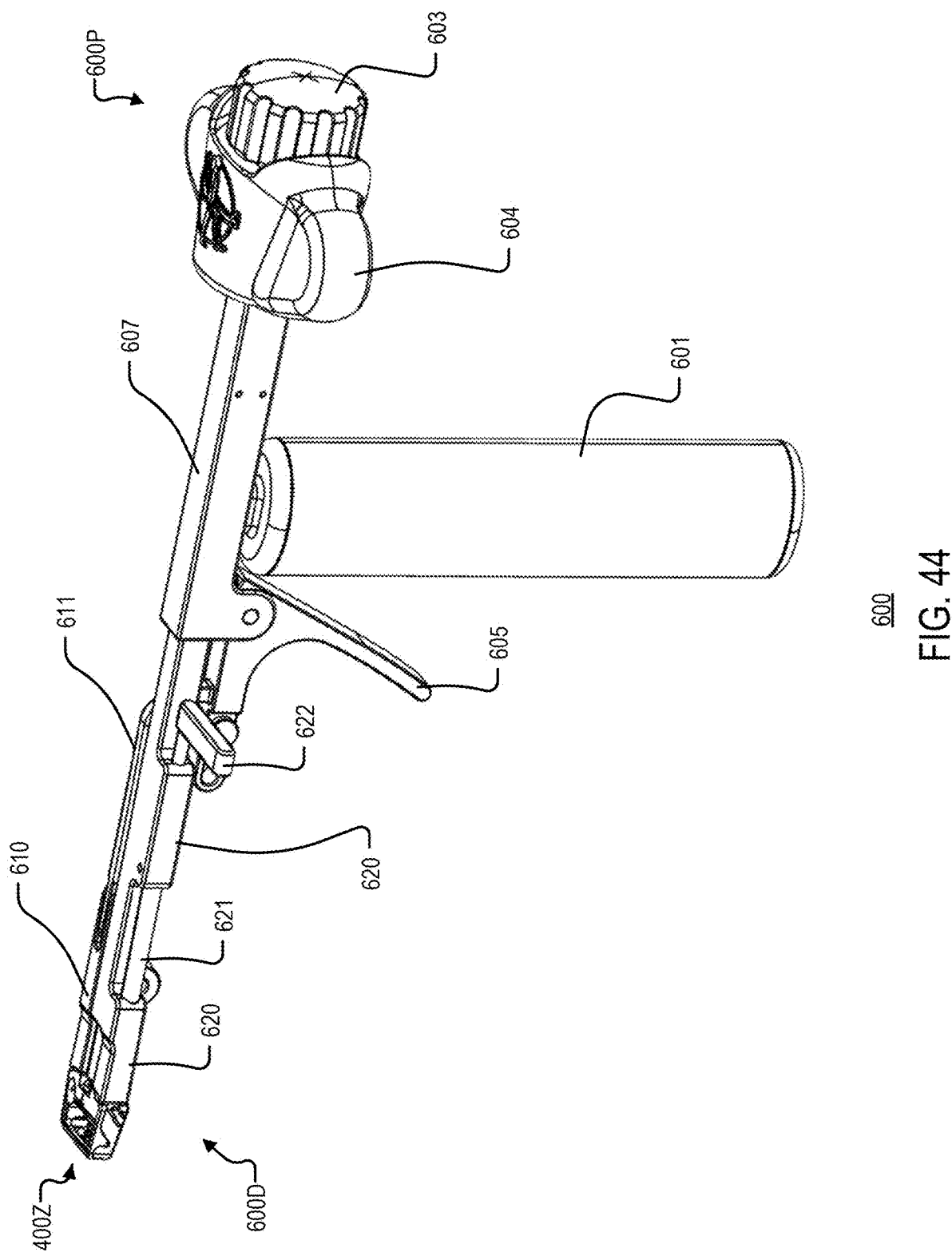
FIG. 44 is a perspective view of a surgical tool for use with disclosed implant embodiments.
Figure 45:
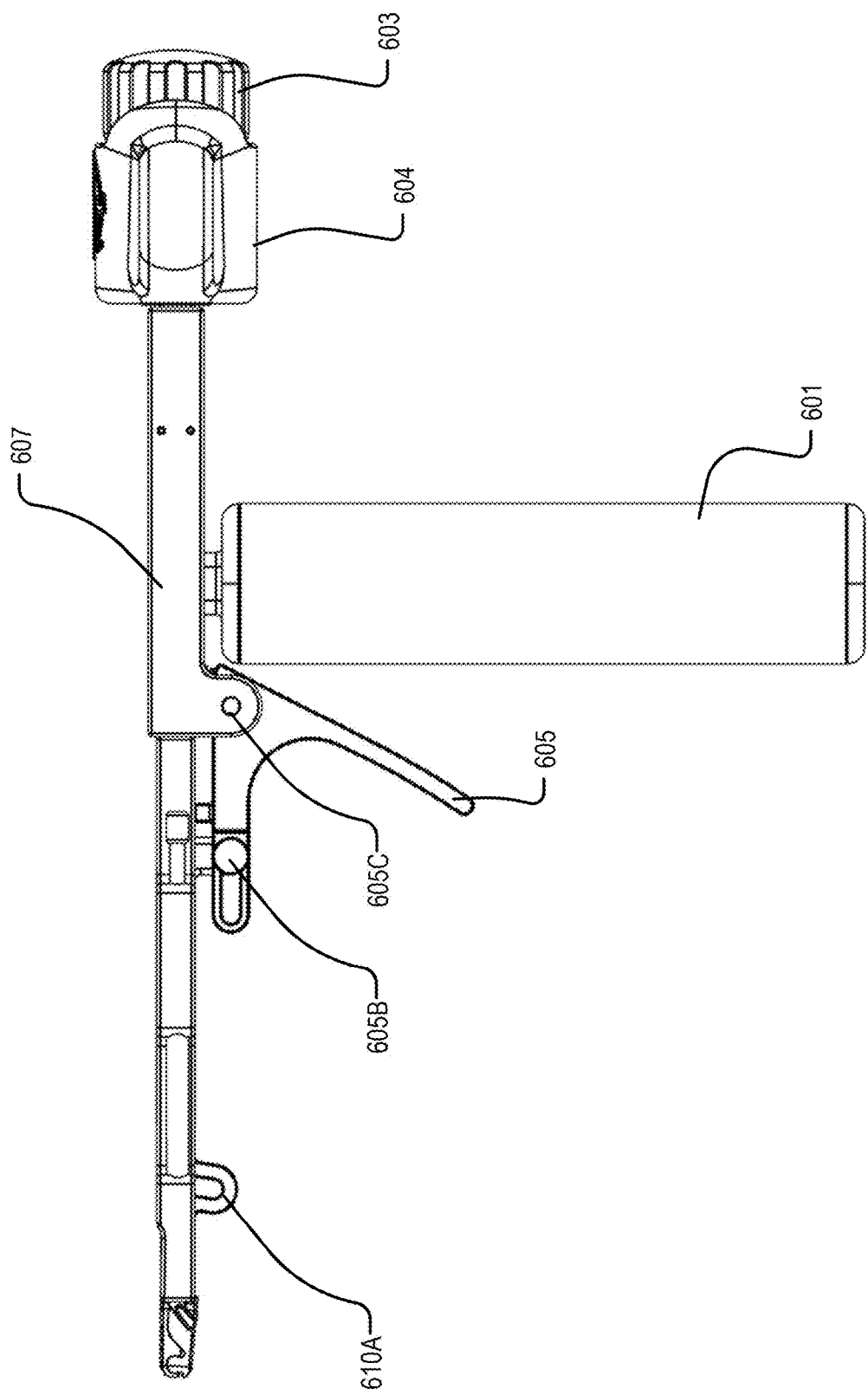
FIG. 45 is a first side view of a surgical tool for use with disclosed implant embodiments.
Figure 46A:
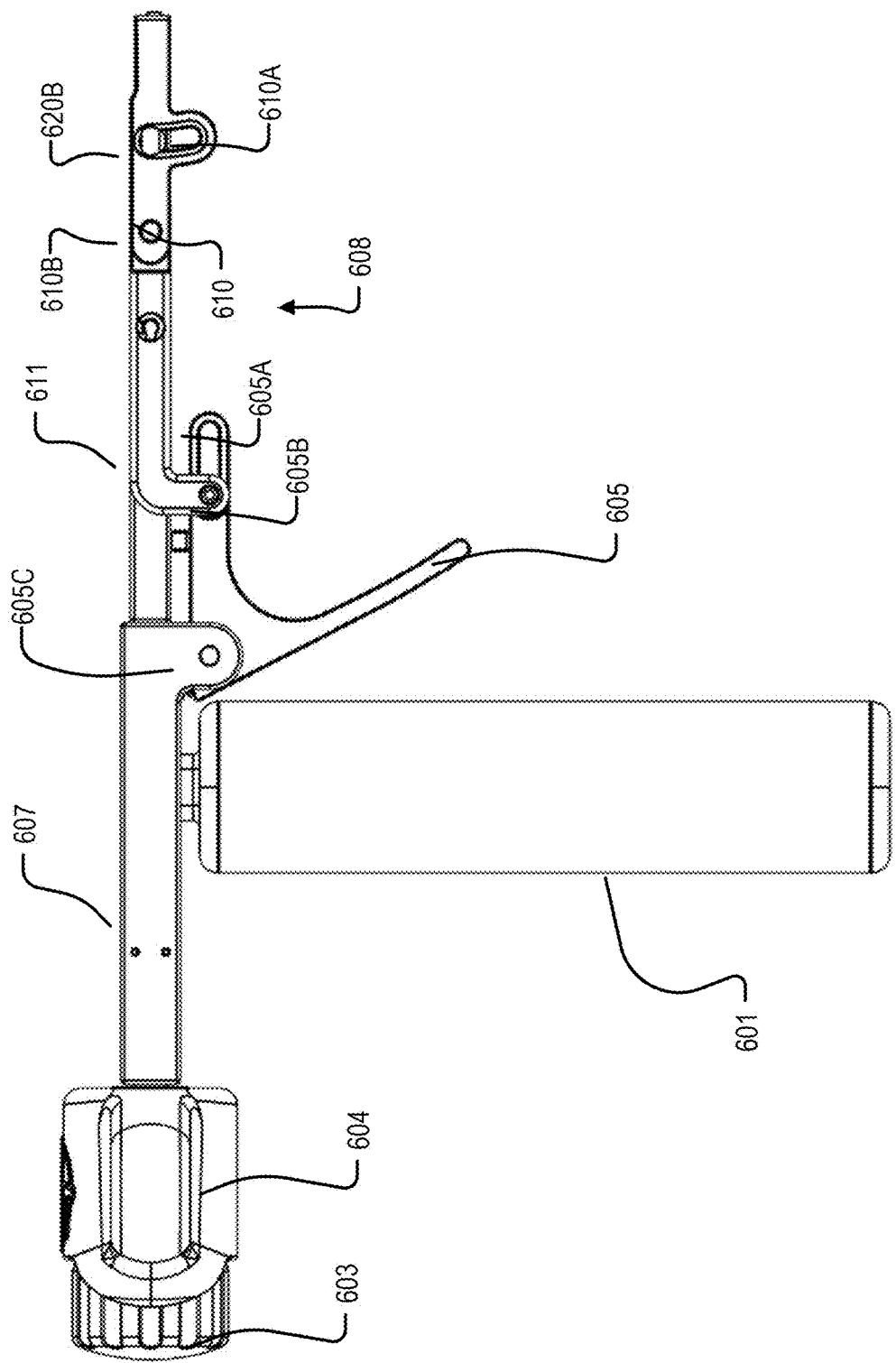
FIG. 46A is a second side view of a surgical tool for use with disclosed implant embodiments.
Figure 46B:
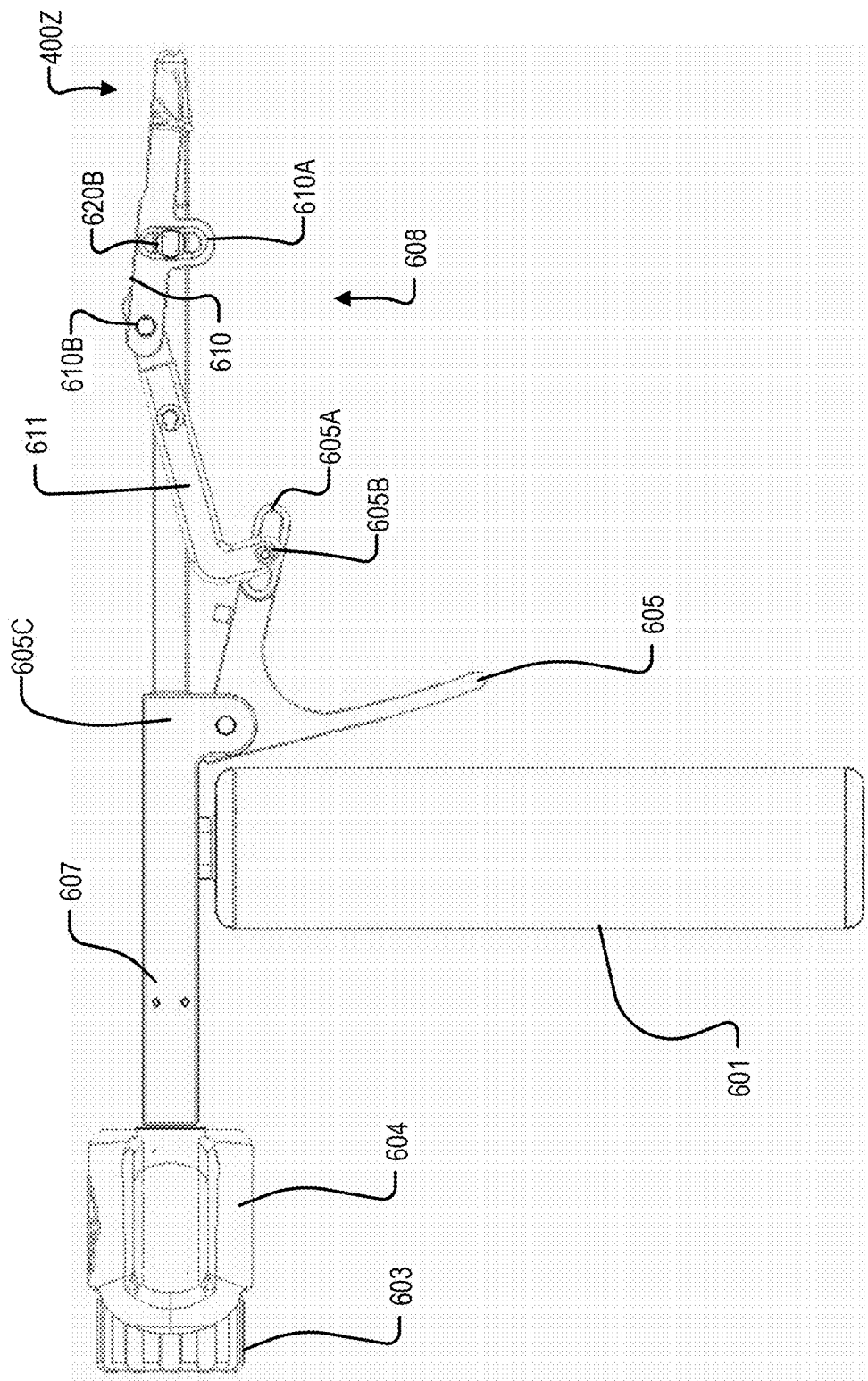
FIG. 46B is a third side view of a surgical tool in an operative position for use with disclosed implant embodiments.
Figure 46C:
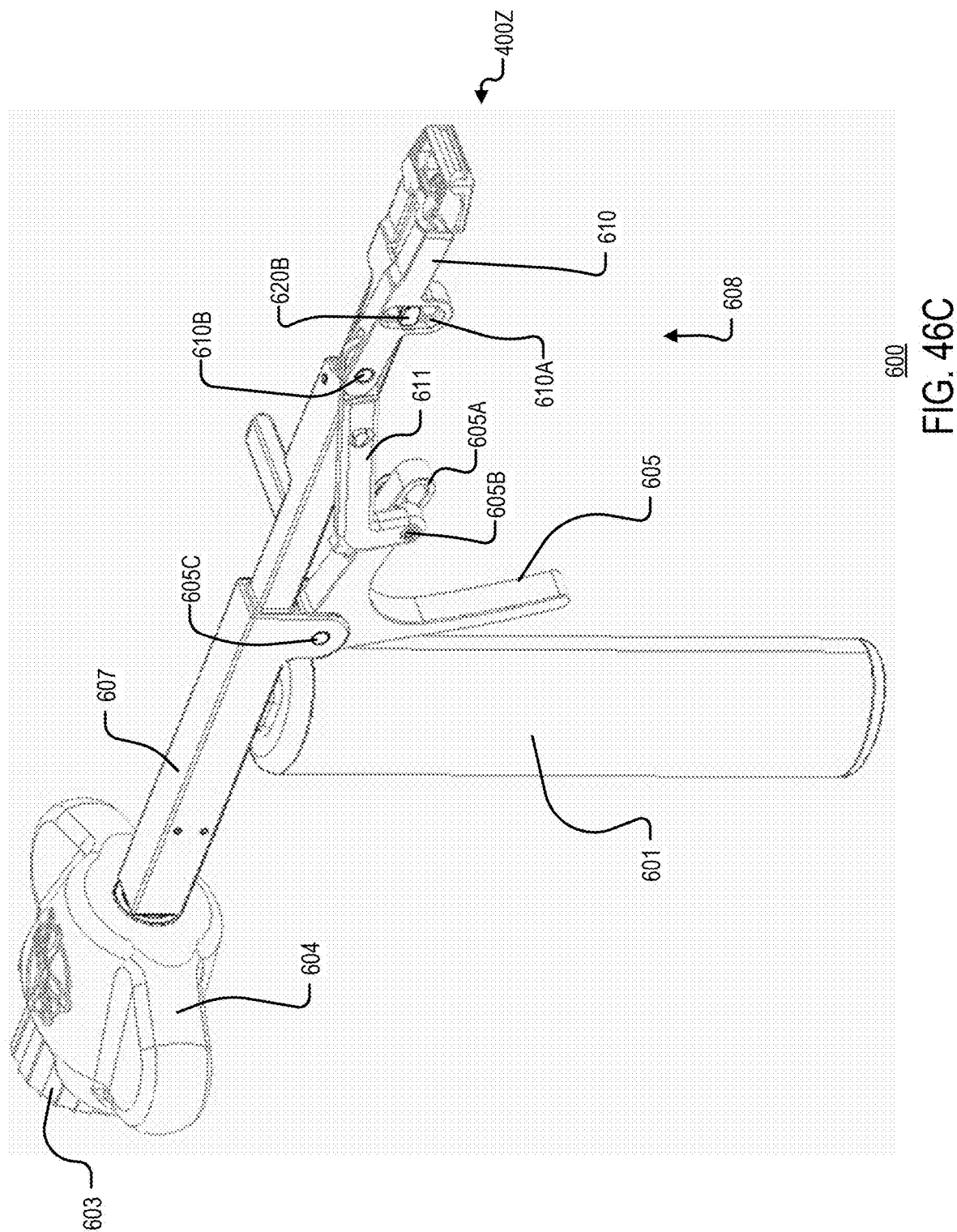
FIG. 46C is a perspective view of a surgical tool in the operative position.
Figure 47A:
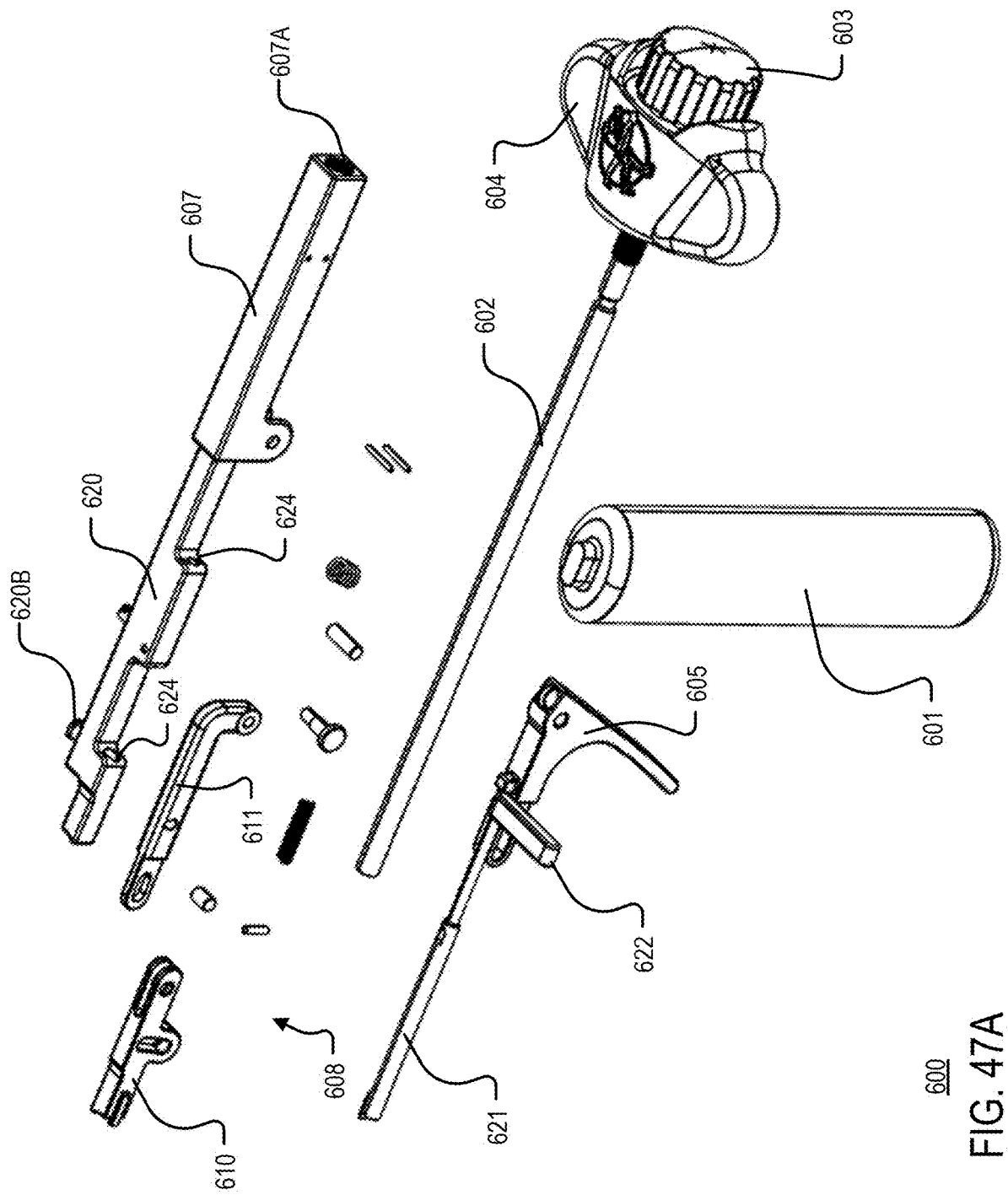
FIG. 47A is first exploded parts view of a surgical tool for use with disclosed implant embodiments.
Figure 47B:
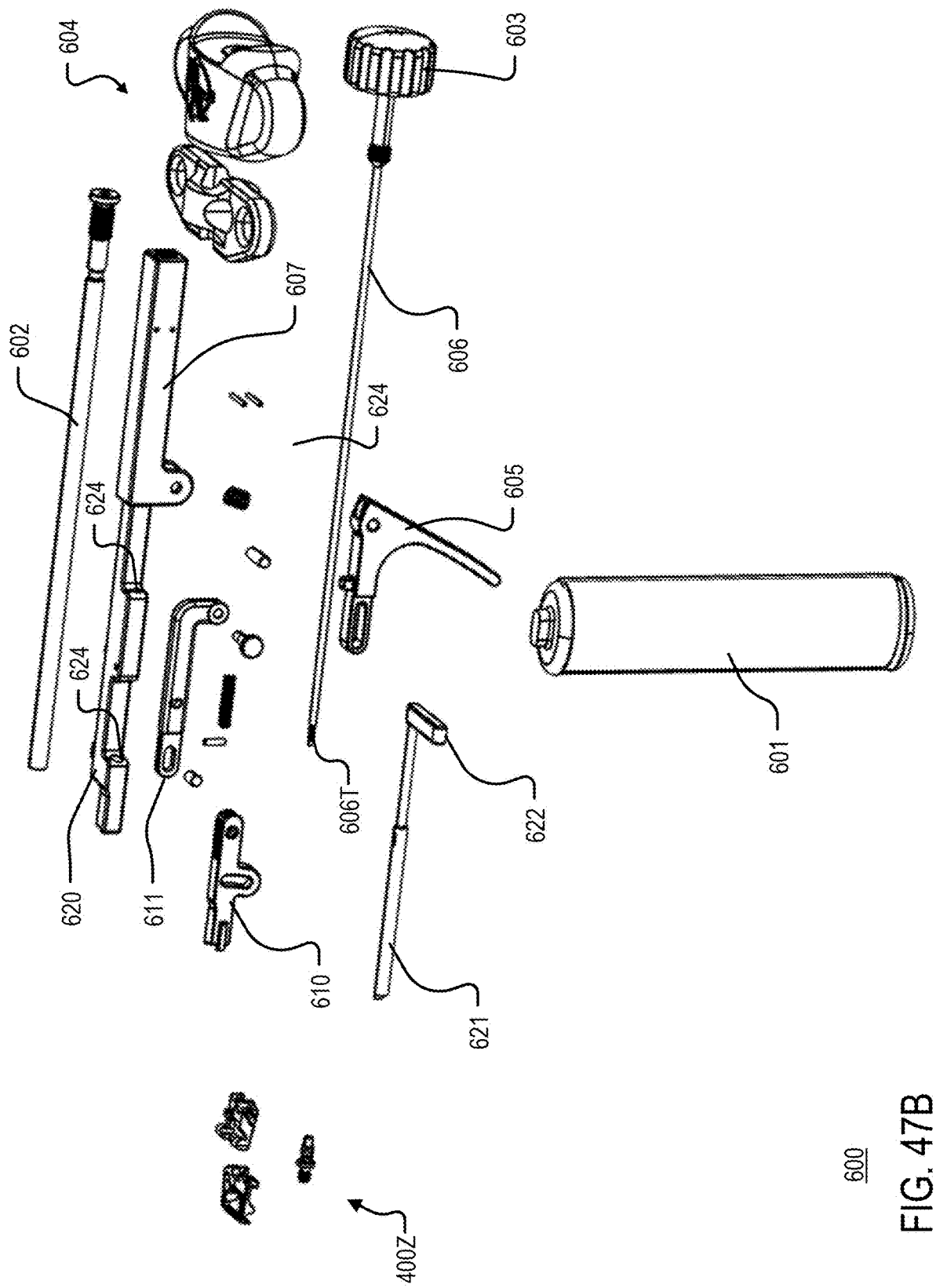
FIG. 47B is second exploded parts view of a surgical tool for use with disclosed implant embodiments.
Figure 48:
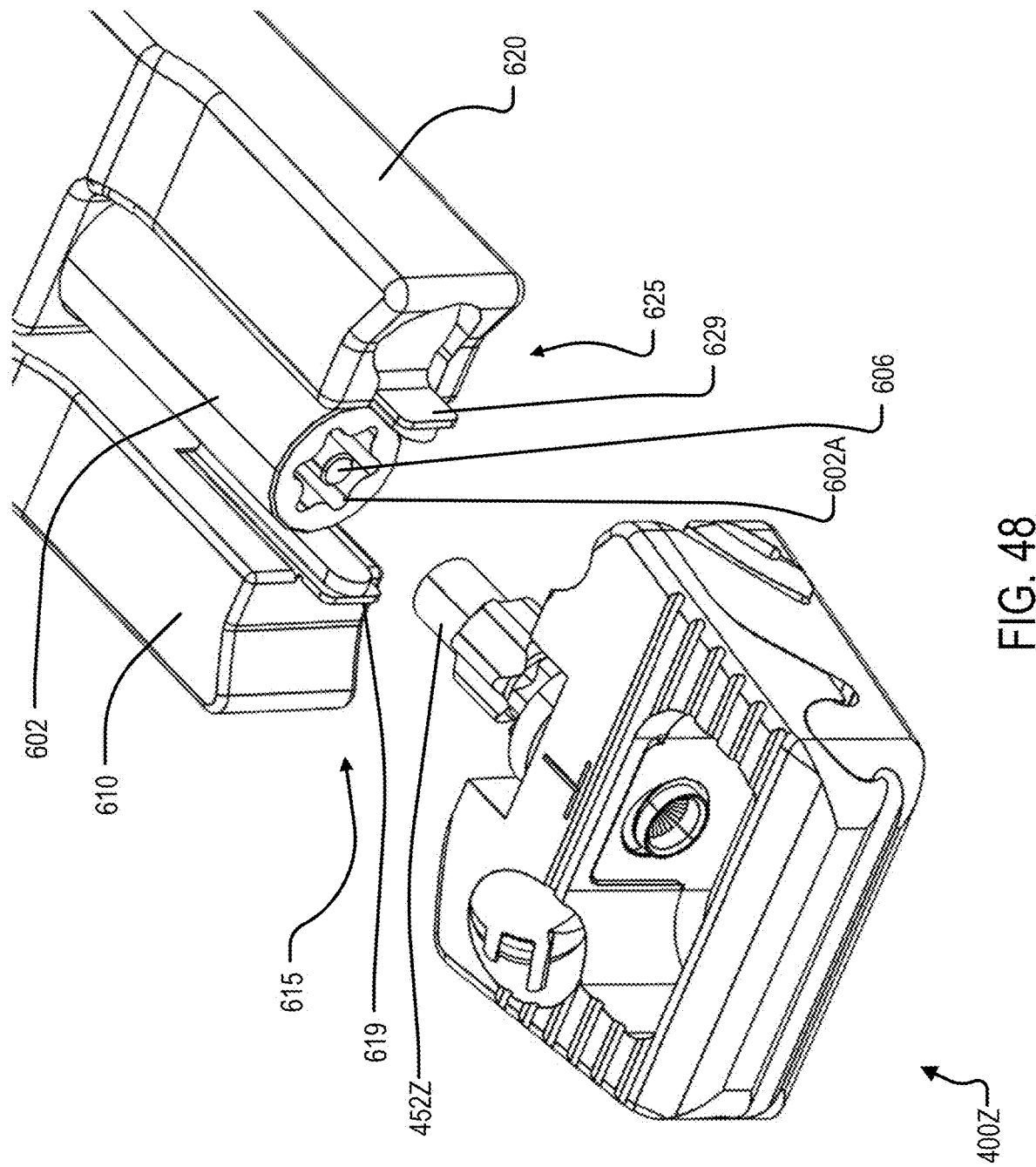
FIG. 48 is a perspective view showing a surgical tool immediately prior to coupling with a surgical implant.

Referring generally to FIGS. 44-48, various views of a surgical tool 600 are disclosed. FIG. 44 illustrates the surgical tool 600 coupled to implant 400Z. FIG. 44 is a perspective view of surgical tool 600; FIG. 45 is a first side view of surgical tool 600; and FIG. 46A is a second side view of surgical tool 600. FIG. 46B is a third side view of surgical tool 600 in an operative position and FIG. 46C is a perspective view of surgical tool 600 in the operative position of FIG. 46B. FIG. 47A is an exploded parts view of surgical tool 600 with select parts removed for ease of understanding and FIG. 47B is an exploded parts view of surgical tool 600 showing additional detail and parts. FIG. 48 illustrates surgical tool 600 immediately prior to coupling with implant 400Z. In the example embodiment, tool 600 may serve several purposes. For example, tool 600 may be used to insert implant 400Z, expand implant 400Z, and in some embodiments may also rotate breakoff screw 450 to cause it to separate into two portions along breakoff location 455 (see FIG. 34).

With reference to the perspective view of FIG. 44 and the exploded parts views of FIGS. 47A and 47B, tool 600 may include a gripping handle 601 that is securely coupled to first body portion 607. First body portion 607 may rotatably support an inner shaft 606 and an outer shaft 602 therein. Shafts 606, 602 may extend through aperture 607A of first body portion 607 in a longitudinal direction from a proximal end to a distal end. The inner shaft 606 may be securely connected to turn knob 603 at a proximal end 600P and the outer shaft 602 may be securely connected to turn handle 604 at the proximal end 600P. The inner shaft 606 may extend through outer shaft 602 and include a thread pattern 606T at a distal end thereof for securely connecting to corresponding threads 456 of breakoff screw 450 (see FIG. 42B for example). The inner shaft 606 may be independently rotatable relative to outer shaft 602 by rotating turn knob 603. Additionally, the outer shaft 602 may be independently rotatable relative to inner shaft 606 by rotating turn handle 604, for example. Generally, both the inner shaft 606 and outer shaft 602 will interact with and/or couple to breakoff screw 450 as will be explained in further detail below.

With reference to FIGS. 45 and 46A-46C, tool 600 may include an actuator 605 in the form of a trigger that is connected to first body portion 607 at pin 605C. Actuator 605 may be actionable to expand implant 400Z by pivoting a linkage assembly 608 including first arm 610 and second arm 611 relative to a third fixed arm 620, for example. Second arm 611 may be coupled to actuator 605 via pin 605B such that pin 605B may be linearly translatable forward and backward in a proximal-to-distal direction within slotted aperture 605A. In turn, second arm 611 may be coupled to first arm 610 via pin 610B such that second arm 611 may pivot up and down. Additionally, first arm 610 may be coupled to third arm 620 and in various embodiments third arm 620 may be fixed relative to first body portion 607. Additionally, third arm 620 may include a protrusion 620B which may be slidably seated within a curved vertical slot, for example slot 610A, and thereby guide motion of arm 610 as it pivots up and down. As seen best in FIGS. 46B and 46C, depressing actuator 605 may cause linkage assembly 608 to pivot by causing second arm 611 to move distally such that first arm 610 pivots relative to third arm 620 and implant 400Z may be expanded.

With reference back to FIG. 44, third arm 620 may include an aperture extending therethrough in a proximal to distal direction for accommodating a linearly translatable shaft 621. Shaft 621 may independently move forward and backward in a proximal to distal direction within the through aperture 624 of third fixed arm 620 (see FIGS. 47A and 47B), for example. Shaft 621 may include a charging handle at a proximal end thereof allowing an end user to manipulate shaft 621 in a forward and backward motion (proximal motion and distal motion in the proximal-to-distal direction). In some embodiments, an end user may translate charging handle 622 rotatably in a clockwise or counter-clockwise motion, for example to lock shaft 621 in a relative position. Additionally, in some embodiments, when shaft 621 is not in a locked position, depressing actuator 605 will not expand implant 400Z for reasons explained in more detail below.

With reference to FIG. 48, first arm 610 may include a gripping outdent 619 having a size and shape generally corresponding to a size and shape of gripping indentation 419Z. Additionally, first arm 610 may include a counter torque surface 615 having a size and shape generally corresponding to a size and shape of the proximal surface of the superior endplate 410, for example. Similarly, shaft 621, extending through fixed arm 620, may include a gripping outdent 629 having a size and shape generally corresponding to a size and shape of gripping indentation 429Z (as shown in FIG. 42A). Additionally, second arm 620 may include a counter torque surface 625 having a size and shape generally corresponding to a size and shape of the proximal surface of the inferior endplate 420, for example. In this way, when shaft 621 is moved distally such that the outdent 629 is seated within indent 429Z and outdent 619 is seated within indentation 419Z (as shown in FIG. 42A) an end user may activate actuator 605 to expand implant 400Z while surfaces 615, 625 resist a twisting motion of implant 100. For example, as shown in FIGS. 46B and 46C an end user may depress actuator 605 by squeezing the trigger which in turn may cause the linkage assembly 608 to pivot the first arm 610 relative to fixed arm 620 such that tool 600 may urge the superior endplate 410 and inferior endplate 420 away from one another.

Figure 49:
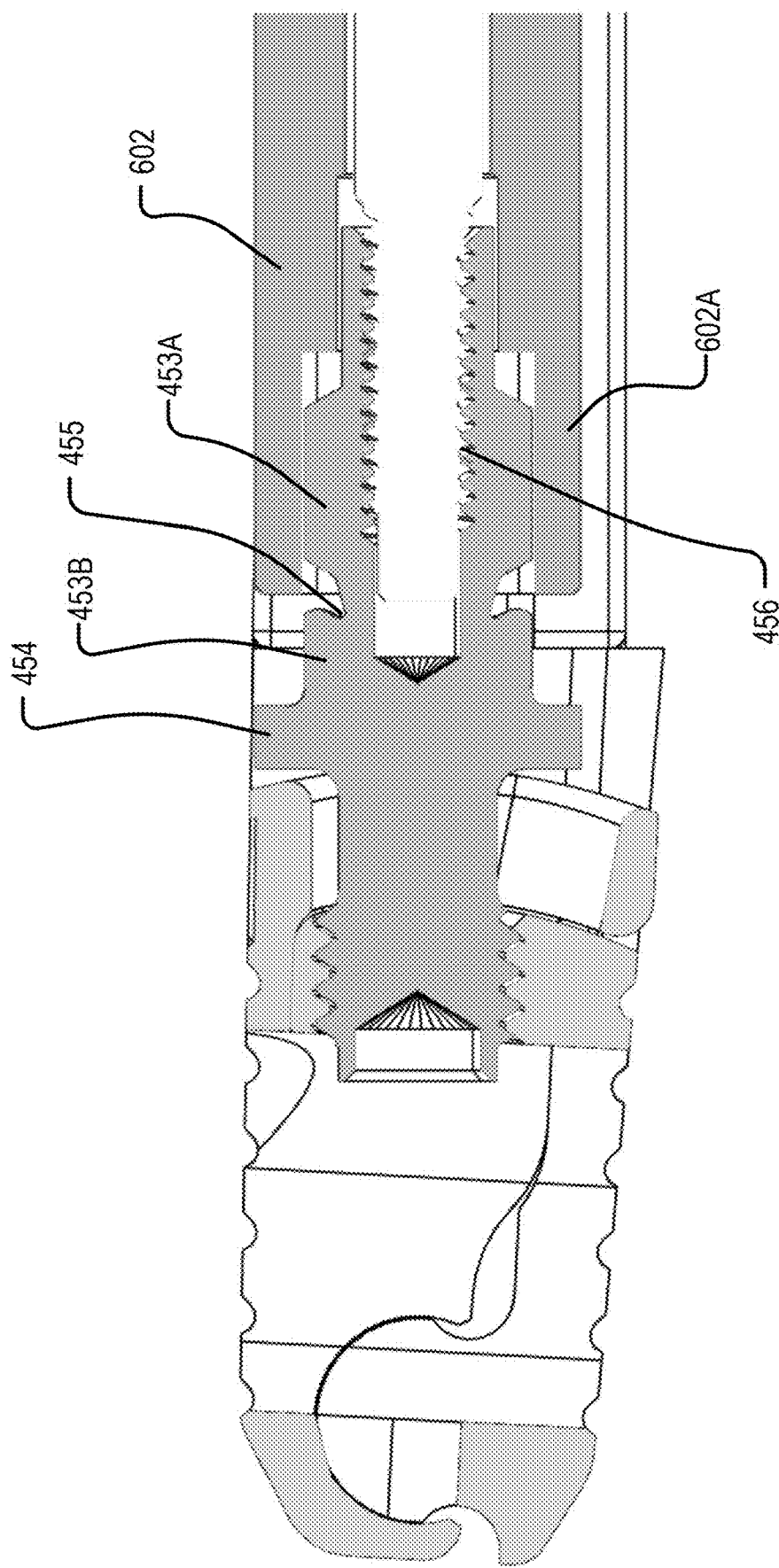
FIG. 49 is a first cross section drawing of the surgical tool and implant in a coupled configuration.
Figure 50:
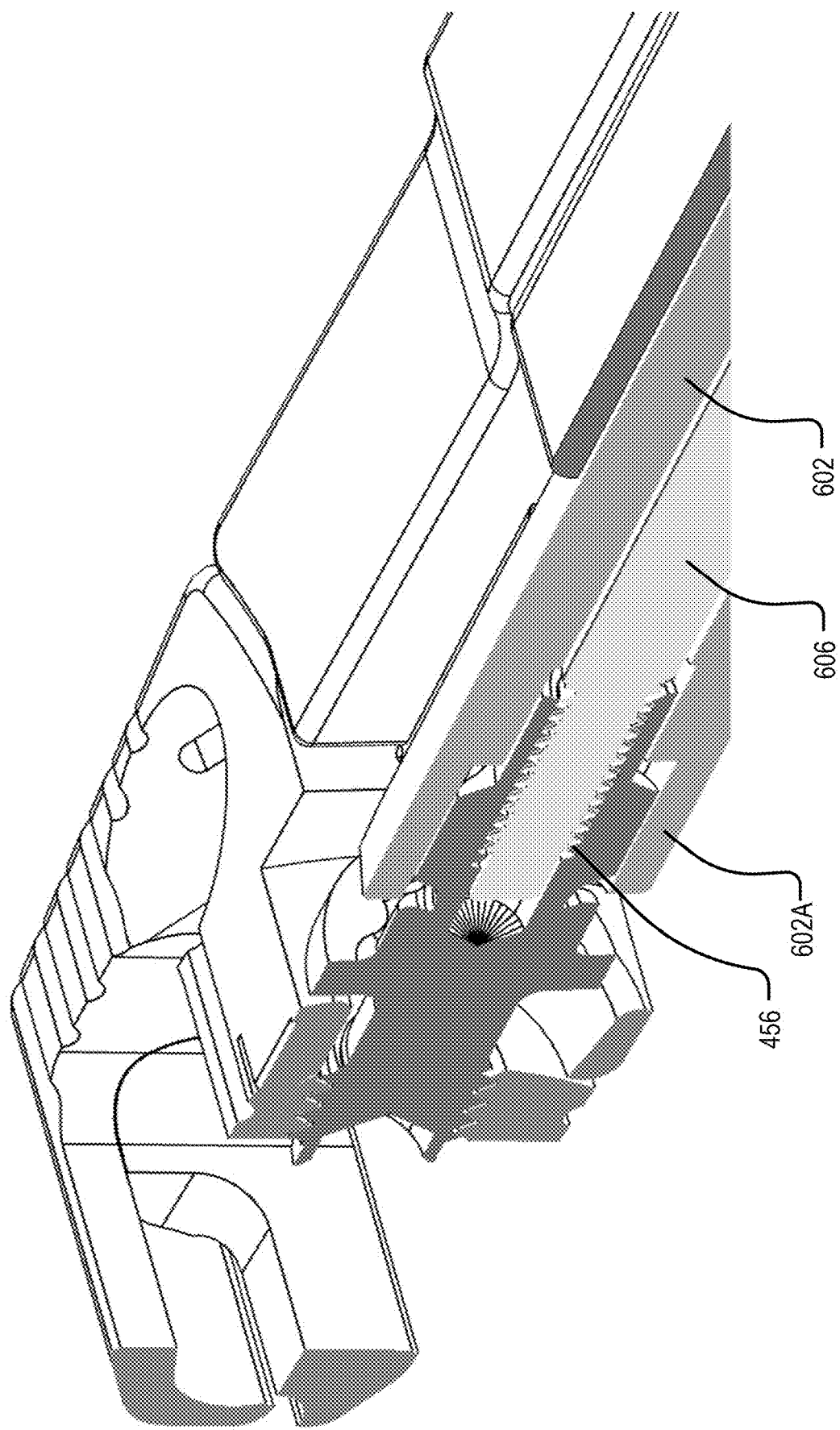
FIG. 50 is a second cross section drawing of the surgical tool and implant in a coupled configuration.
Figure 51:
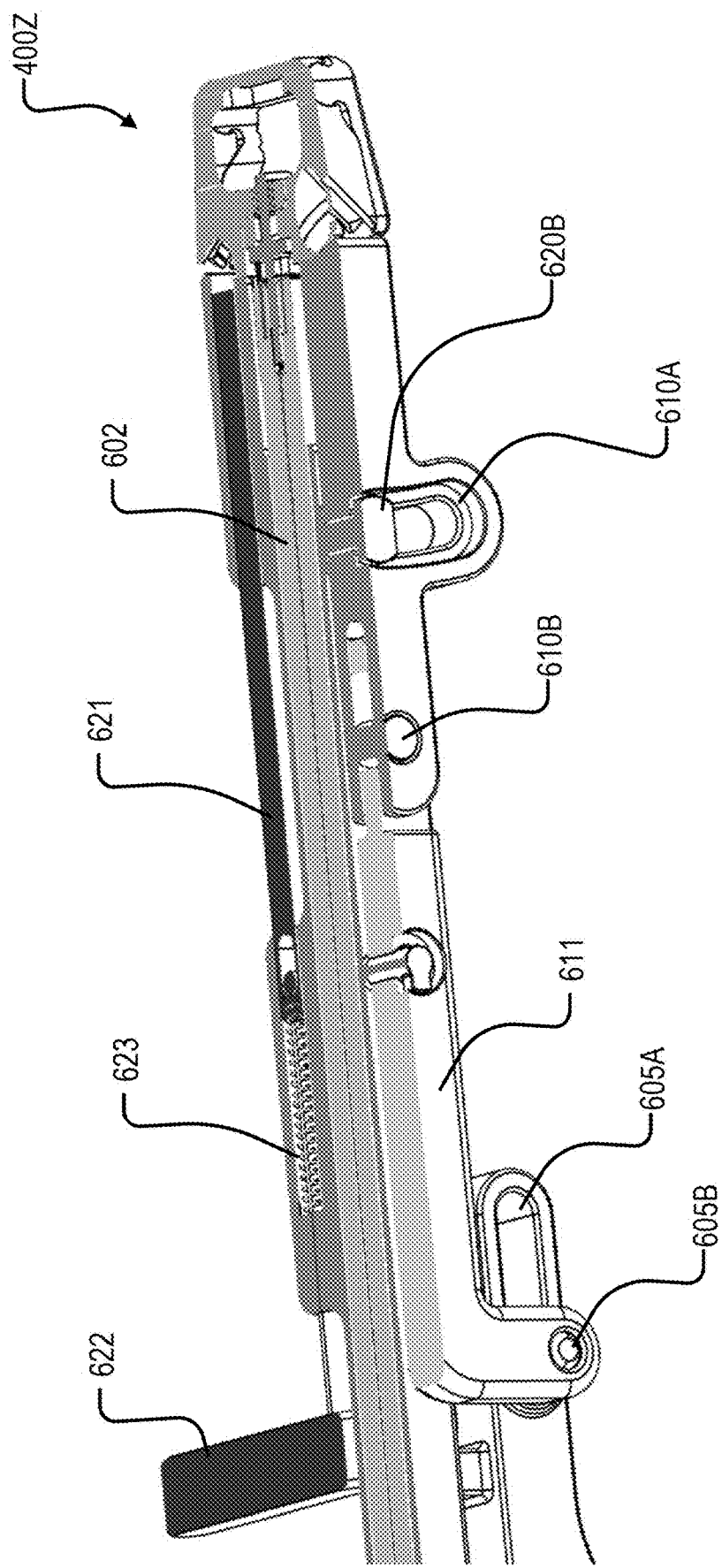
FIG. 51 is a third cross section drawing of the surgical tool and implant in a coupled configuration.

With reference to the cross-section drawings of FIGS. 49, 50, and 51 additional features and functionality of tool 600 will be explained. In FIGS. 49 and 50, it is shown that the threaded end of inner shaft 606 is threadably engaged with the threaded aperture 456 of breakoff screw 450. Additionally, a proximal drive feature 453A is mated within a corresponding female drive feature 602A (see FIG. 48) at the distal most end of outer shaft 602. As explained previously, inner shaft 606 and outer shaft 602 are independently operable. In use, an end user may initially position inner shaft 606 adjacent to/within the front portion of threaded aperture 452 and rotate inner shaft 606 via turn knob 603. As inner shaft 606 is rotated, implant 400Z is pulled towards tool 600. FIGS. 49-51 show implant 400 after inner shaft 606 has been sufficiently rotated such that implant 400Z abuts the counter torque surfaces 615, 625 and the gripping protrusion 619 may be seated within the corresponding gripping indentation 419Z. With reference to FIG. 51, once implant 400Z is pulled sufficiently towards tool 600, an end user may actuate shaft 621 by pushing on charging handle 622 to overcome the biasing force of spring 623 such that gripping protrusion 629 may be seated within the corresponding gripping indentation 429Z, for example. In some embodiments, an end user may rotate charging handle 622 such that biasing force of spring 623 is prevented from urging shaft 621 away from implant 400Z. At this point, the implant 400Z may be in an operatively engaged position with tool 600.

Once implant 400Z is in the operatively engaged position, an end user may insert implant 400Z into a disc space between a superior vertebra and inferior vertebra (cephalad vertebra and caudal vertebra), for example. After the implant 400Z is positioned between the superior and inferior vertebrae, an end user may depress actuator 605 thereby causing the linkage assembly 608 to pivot and spread the superior endplate 410 apart from the inferior endplate 420. Once the end user has expanded implant 400Z to an appropriate position, the end user may rotate turn handle 604 which will rotate breakoff screw 450 via first drive feature 453A. The end user may continue to rotate breakoff screw 450 such that it advances into implant 400Z in a proximal to distal direction and locks implant 400Z in the expanded configuration similarly as explained above. The end user may continue to rotate turn handle 604 until the torque applied to breakoff screw 450 is great enough that the breakoff screw 450 will shear into two pieces similarly as explained above. Notably, the broken off or sheared off portion of breakoff screw 450 may be retained by tool 600 on account of inner shaft 606 being threadably coupled to threaded aperture 452.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof

What is claimed is:

1. An expandable implant movable between a contracted position and an expanded position, comprising:
   an expandable body extending from a proximal end to a distal end in a proximal-to-distal direction and extending from a first lateral side to a second lateral side in a widthwise direction, the expandable body being defined by a superior endplate and an inferior endplate that are hingedly connected;
   the superior endplate comprising a first core having a screw slot and a distal engagement surface;
   the inferior endplate comprising a second core having a proximal engagement surface; and
   a locking screw extending in a longitudinal direction from a proximal end to a distal end, being extendable through the first core and the second core, and being movable between a locked position and an unlocked position,
   wherein, in the locked position, the locking screw urges the distal engagement surface of the first core against the proximal engagement surface of the second core,
   wherein the proximal end of the locking screw is defined by an exposed aperture having an internal threaded surface, and
   wherein the locking screw comprises a proximal portion and a distal portion that are configured to separate along a recessed fracture surface, and, when separated, the recessed fracture surface is recessed relative to a sidewall of the distal portion and the fracture surface is recessed relative to a proximal most edge of the distal portion.

2. The expandable implant of claim 1, wherein:
   the superior endplate comprises a first gripping indentation located at a proximal end thereof; and
   the inferior endplate comprises a second gripping indentation located at a proximal end thereof.

3. The expandable implant of claim 2, wherein:
   the first gripping indentation comprises a slot having a superior curved surface and an inferior curved surface; and
   the second gripping indentation comprises a slot having a superior curved surface and an inferior curved surface.

4. The expandable implant of claim 1, wherein:
   the superior endplate comprises a first plurality of engagement features that are angled 20 degrees to 40 degrees with respect to a proximal surface of the superior endplate; and
   the inferior endplate comprises a second plurality of engagement features that are angled 20 degrees to 40 degrees with respect to a proximal surface of the inferior endplate.

5. The expandable implant of claim 1, wherein:
   the superior endplate further comprises a channel located adjacent the distal end and extending in the widthwise direction; and
   the inferior endplate further comprises a rail located adjacent the distal end and extending in the widthwise direction, the rail having a size and shape generally corresponding to a size and shape of the channel and being located within the channel.

6. The expandable implant of claim 5, wherein:
   the distal engagement surface of the first core comprises a first curved surface;

the proximal engagement surface of the second core comprises a second curved surface; and the first curved surface is defined by a radius of a circle having a center point that is offset from an axis of rotation of the rail.

7. The expandable implant of claim 5, wherein:

the superior endplate comprises at least one hook portion adjacent the channel;

the inferior endplate comprises at least one relief portion adjacent the rail;

the at least one hook portion has a size and shape generally corresponding to a size and shape of the at least one relief portion; and the at least one hook portion is disposed within the at least one relief portion.

8. The expandable implant of claim 7, wherein, in a cross-section view, the channel comprises an arcuate shape and the rail comprises an arcuate shape.

9. The expandable implant of claim 1, wherein:

the locking screw comprises a threaded distal end and a drive feature;

the first core is disposed proximally with respect to the second core; and the locking screw is threadably engaged with at least one of the first core and second core.

10. A system, comprising:

an expandable implant movable between a contracted position and an expanded position, the implant comprising:

an expandable body extending from a proximal end to a distal end in a proximal-to-distal direction and extending from a first lateral side to a second lateral side in a widthwise direction, the expandable body being defined by a superior endplate and an inferior endplate that are hingedly connected;

the superior endplate comprising a first core having screw slot and a distal engagement surface;

the inferior endplate comprising a second core having a proximal engagement surface; and a locking screw movable between a locked position and an unlocked position;

wherein, in the locked position, the locking screw urges the distal engagement surface of the first core against the proximal engagement surface of the second core; and a surgical tool configured to move the implant from the contracted position to the expanded position and to move the locking screw between the locked position and the unlocked position, the surgical tool being capable of moving the locking screw into the locked position while supporting the implant in the expanded position, wherein the surgical tool further comprises:

a body portion having an aperture extending therethrough;

a pivotal linkage assembly including a first arm and a second arm;

a third arm that is fixed relative to the body portion;

an outer shaft extending through the body portion and having a drive feature at a distal end thereof for rotating the locking screw from the unlocked position to the locked position; and an inner shaft extending through the outer shaft and having a first thread pattern at an end thereof for drawing the implant towards the surgical tool.

11. The system of claim 10, wherein:

the superior endplate comprises a first gripping indentation located at a proximal end thereof;

the inferior endplate comprises a second gripping indentation located at a proximal end thereof;

the surgical tool comprises a first gripping protrusion having a size and shape generally corresponding to a size and shape of the first gripping indentation; and the surgical tool comprises a second gripping protrusion having a size and shape generally corresponding to a size and shape of the second gripping indentation.

12. The system of claim 11, wherein:

the first gripping indentation comprises a slot having a superior curved surface and an inferior curved surface; and the second gripping indentation comprises a slot having a superior curved surface and an inferior curved surface.

13. The system of claim 10, wherein the surgical tool comprises a pivotal linkage assembly including a first arm and a second arm.

14. The system of claim 10, wherein:

the surgical tool is configured to separate the locking screw into the proximal portion and distal portion while the implant is in the expanded position and retain the proximal portion of the locking screw via the inner shaft.

15. The system of claim 10, wherein the surgical tool further comprises an actuator for causing the pivotal linkage assembly to pivot relative to the third arm and thereby expand the implant.

16. The system of claim 10, wherein:

the superior endplate further comprises a channel located adjacent the distal end and extending in the widthwise direction; and the inferior endplate further comprises a rail located adjacent the distal end and extending in the widthwise direction, the rail having a size and shape generally corresponding to a size and shape of the channel and being located within the channel.

17. The system of claim 16, wherein:

the distal engagement surface of the first core comprises a first curved surface;

the proximal engagement surface of the second core comprises a second curved surface; and the first curved surface is defined by a radius of a circle having a center point that is offset from an axis of rotation of the rail.

* * * * *